(12) United States Patent
Gilchrist et al.

(10) Patent No.: US 8,530,235 B2
(45) Date of Patent: Sep. 10, 2013

(54) MEDIUM THAT SUPPORTS CULTURE OF AN OOCYTE AND MODULATION OF GRANULOSA CELL APOPTOSIS

(75) Inventors: Robert B. Gilchrist, Croydon (AU); Jeremy Thompson, Grange South (AU); Tamer Hussein, Woodville South (AU)

(73) Assignee: Adelaide Research & Innovation Pty Ltd., Adelaide (AU)

( * ) Notice: Subject to any disclaimer, the term of this patent is extended or adjusted under 35 U.S.C. 154(b) by 263 days.

(21) Appl. No.: 11/988,949

(22) PCT Filed: Jul. 18, 2006

(86) PCT No.: PCT/AU2006/001002
§ 371 (c)(1),
(2), (4) Date: Jul. 9, 2008

(87) PCT Pub. No.: WO2007/009166
PCT Pub. Date: Jan. 25, 2007

(65) Prior Publication Data
US 2008/0274963 A1 Nov. 6, 2008

(30) Foreign Application Priority Data
Jul. 18, 2005 (AU) ................ 2005903782

(51) Int. Cl.
*C12N 5/00* (2006.01)
*A61K 38/22* (2006.01)
(52) U.S. Cl.
USPC ............ 435/384; 435/1.1; 435/387; 514/9.7; 514/9.8; 514/9.9
(58) Field of Classification Search
None
See application file for complete search history.

(56) References Cited

U.S. PATENT DOCUMENTS
6,610,543 B2 * 8/2003 Choay et al. ................ 435/384

FOREIGN PATENT DOCUMENTS
| WO | WO-94/15966 A | 7/1994 |
| WO | WO-99/17797 A | 4/1999 |
| WO | WO-99/50672 A | 10/1999 |
| WO | WO-00/32222 A | 6/2000 |
| WO | WO-01/96393 A2 | 12/2001 |
| WO | WO-2005/097978 A | 10/2005 |
| WO | WO-2006/059913 A | 6/2006 |

OTHER PUBLICATIONS

ATCC, DMEM: F-12 medium description, p. 1, 2009.*
Bowie et al., 1990, Science 247: 1306-1310.*
Wells, 1990, Biochemistry 29:8509-8517.*
Sahin et al., J. Cell. Biol. 164: 769-779, 2004.*
Zheng et al., Mol. Reprod. Dev. 58: 348-355, 2001.*
Su et al., "Synergistic roles of BMP15 and GDF9 in the developement and function of the oocyte-cumulus cell complex in mice:genetic evidence foe an oosyte-granulosa regulatory loop", Developmental Biology; (2004), vol. 276(1): pp. 64-73.
McNatty et al., "Bone morphogenetic protein 15 and growth differentiation factor 9 co-operate to regulate granulosa cell function in ruminants", Reprodunction;(Apr. 2005), vol. 129(4): 481-7.
Yan et al., "Synergistic Roles of Bone Morphogenetic Protein 15 and Growth Differentiation Factor 9 in Ovarian Function", Molecular Endocrinology;(Jun. 2001), vol. 15(6):pp. 854-866.
Senbon et al.,"Interactions between the Oocyte and Surrounding Somatic Cells in Follicular Developement: Lessons from In Vitro Culture", Journal of Reproduction & Development; Aug. 2003, vol. 49(4): pp. 259-269.
Gui et al., "RNA Interference Evidence That Growth Differentiation Factor-9 Mediates Oocyte Regulation of Cumulus Expansion in Mice", Biology of Reproduction; (Jan. 2005), vol. 72(1); pp. 195-199.
Braw-Tal., "The initiation of follicle growth: the oocyte or the somatic cells?", Molecular and Cellular Endocrinology; (2002), vol. 187(2): pp. 11-18.
McNatty et al., "Oocyte-expressed genes affecting ovulation rate", Molecular and Cellular Endocrinology; 2005 vol. 234(1-2): pp. 57-66.
Gilchrist et al.,"Oocyte-somatic cell interactions during follicle development in mammals", Animal Reproduction Science; (2004), vol. 82-83: pp. 431-436.
Hussein et al., "Oocytes prevent cumulus cell apoptosis by maintaining a morphogenic paracrine gradient of bone morphogenetic", Journal of Cell Science; (Nov. 2005), vol. 118(Pt 22): pp. 5257-5268.
Luciano, A.M., et al., "Developmental Capabiilty of Denuded Bovine Oocyte in a Co-Culture System With Intact Cumulus-Oocyte Complexes: Role of Cumulus Cells, Cyclic Adenosine 3',5'-Monophosphate, and Glutathione," Molecular Reproduction and Development, vol. 71, No. 3, pp. 389-397 (2005).
Isobe, N., et al., "Cumulus Cells Suppress Meiotic Progression in Pig Oocytes Cultured In Vitro," Theriogenology, vol. 45, No. 8, pp. 1479-1489 (1996).
Hayashi, M., et al., "Recombinant Growth Differentiation Factor-9 (GDF-9) Enhances Growth and Differentiation of Cultured Early Ovarian Follicles," Endocrinology, vol. 140, No. 3, pp. 1236-1244 (1999).
Hussein, T. S., et al., "Oocyte-secreted factors enhance oocyte developmental competence," Developmental Biology, vol. 296, No. 2, pp. 514-521 (2006).
Li, R., et al., "Oocyte-Secreted Facto(s) Determine Functional Differences Between Bovine Mural Granulosa Cells and Cumulus Cells," Biol. Reprod., vol. 63, pp. 839-845 (2000).
Vanderhyden, B., et al., "Mouse Oocytes Promote Proliferation of Granulosa Cells from Preantral and Antral Follicles In Vitro," Biol. Reprod., vol. 46, pp. 1196-1204 (1992).
Sakakibara, H., et al., "Effect of growth factors in the medium for oocyte maturation and embryo culture on the development of in vitro matured and fertilized bovine oocytes," Japanese Journal of Embroyo[sic] Transfer, vol. 21, No. 2, pp. 66-74 (1999).
Kobayashi, K., et al. "Influence of epidermal growth factor and transforming growth factor-α on in vitro maturation of cumulus cell-enclosed bovine oocytes in a defined medium," J. Reproduction and Fertility, vol. 100, pp. 439-446 (1994).
McNatty, K.P., et al., "Bone morphogenetic protein 15 and growth differentiation factor 9 co-operate to regulate granulosa cell function," Reproduction, vol. 129, pp. 473-480, (2005).

* cited by examiner

*Primary Examiner* — Gyan Chandra
(74) *Attorney, Agent, or Firm* — Birch, Stewart, Kolasch & Birch, LLP.

(57) ABSTRACT

The present invention relates to a method of modulating apoptosis of a granulosa cell. The method includes one or more of the following steps: (i) modulating the concentration and/or activity of BMP-15 and/or BMP-6 that the granulosa cell is exposed to; (ii) modulating activity of a BMP-15 dependent signalling pathway in the granulosa cell; and (iii) modulating activity of a BMP-6 dependent signalling pathway in a granulosa cell.

19 Claims, 27 Drawing Sheets

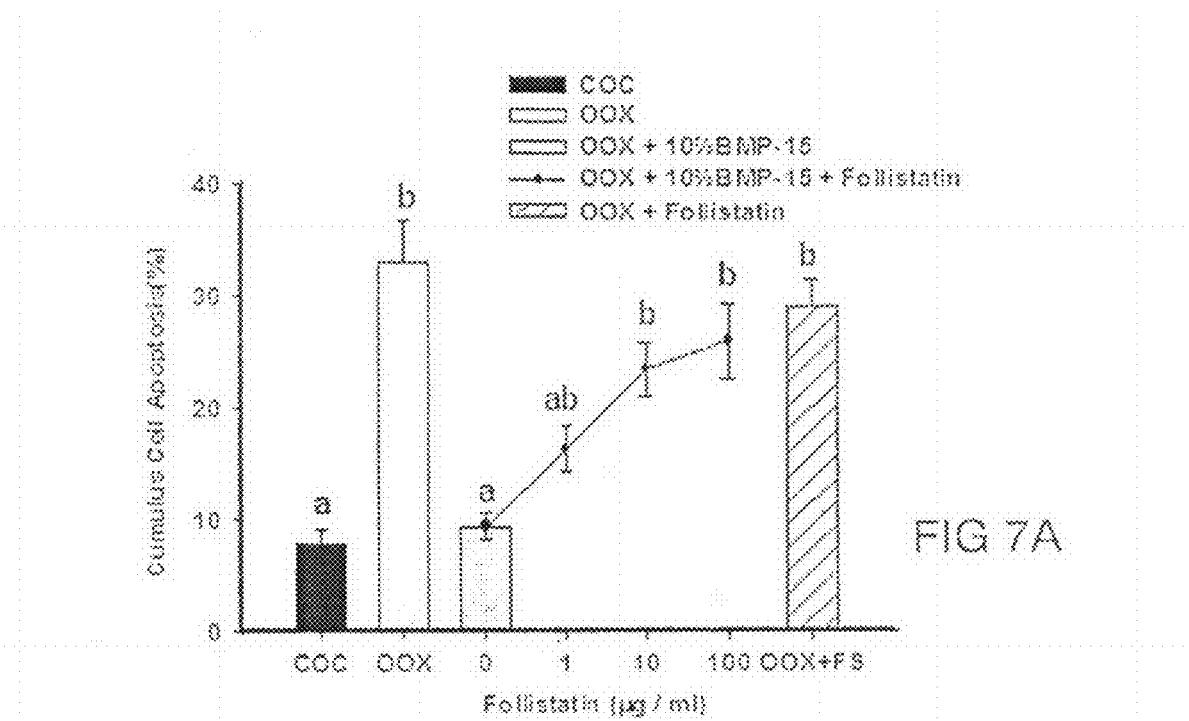
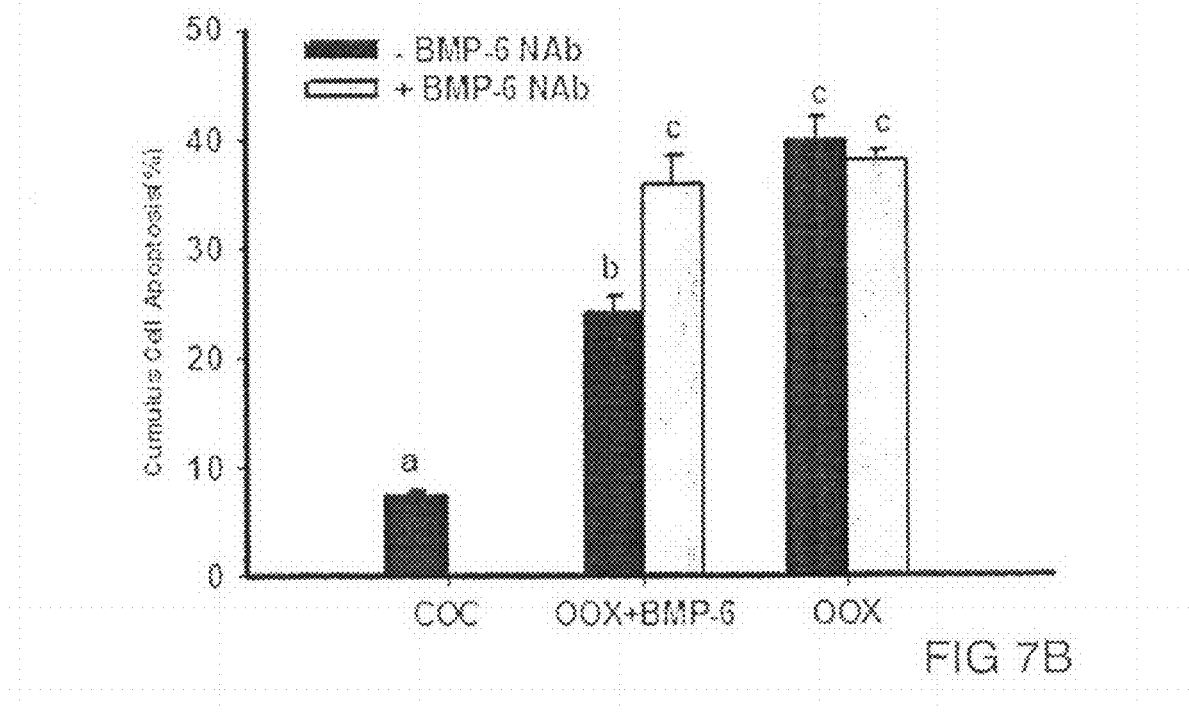

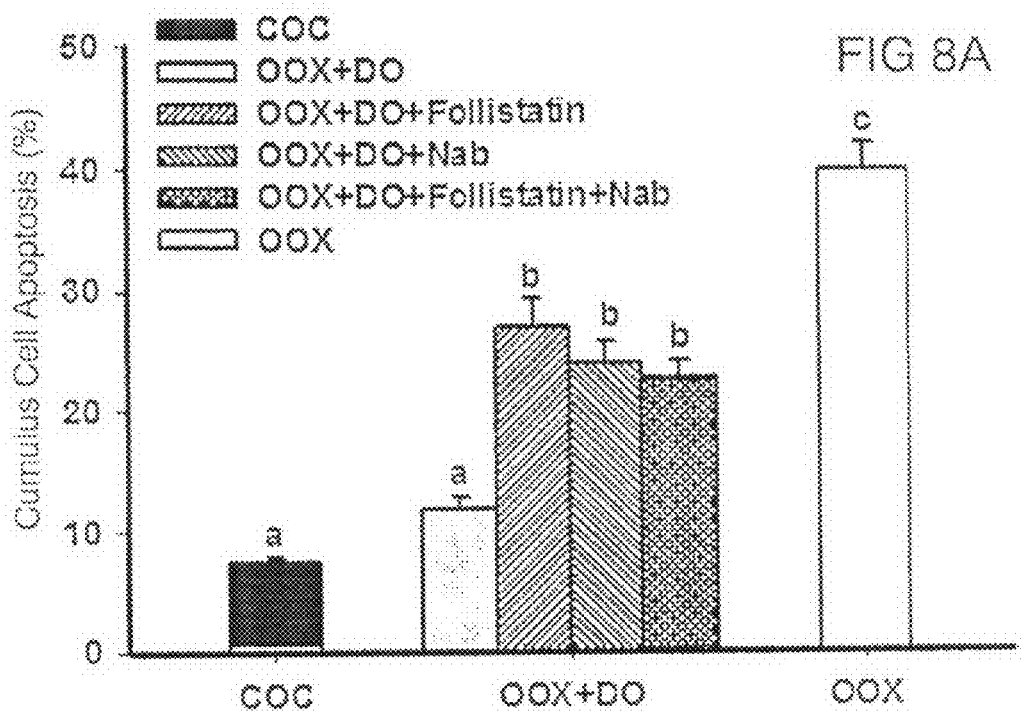
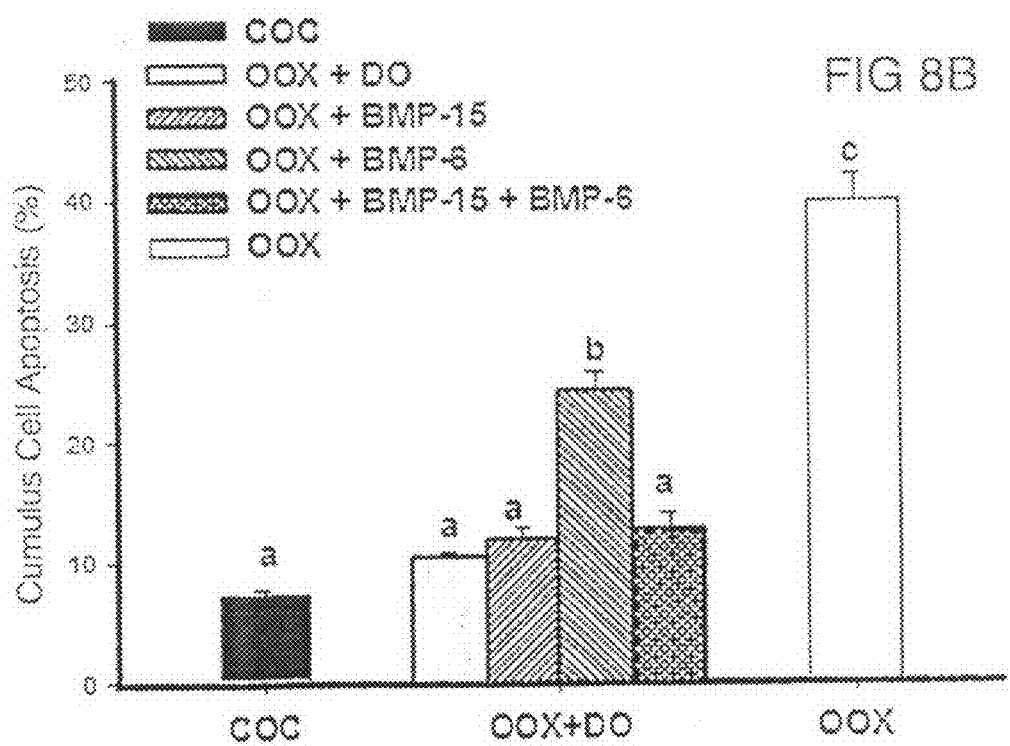

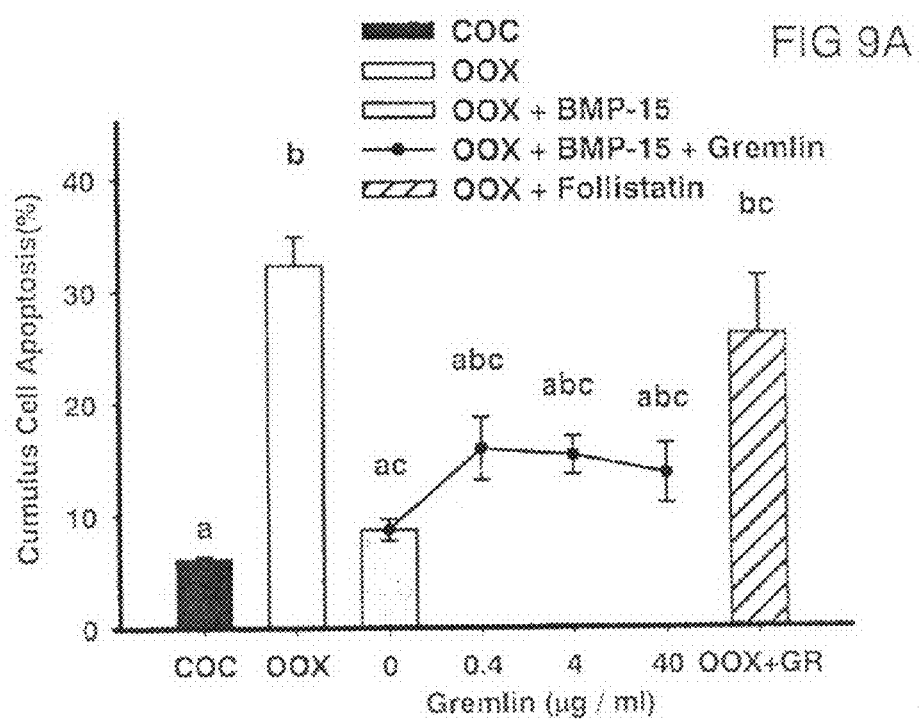
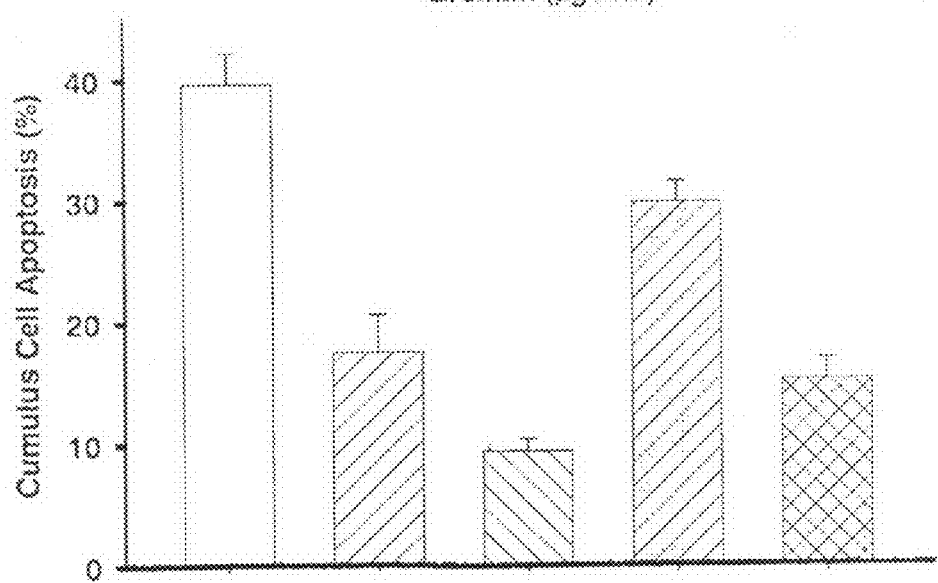
FIG 9B

MEDIUM THAT SUPPORTS CULTURE OF AN OOCYTE AND MODULATION OF GRANULOSA CELL APOPTOSIS

This application claims priority from Australian Provisional Patent Application No. 2005903782 filed on 18 Jul. 2005, the contents of which are to be taken as incorporated herein by this reference.

FIELD OF THE INVENTION

The present invention relates to methods and compositions for modulating the apoptosis of granulosa cells.

The present invention also relates to methods and compositions for modulating oocyte maturation, modulating follicle atresia, development and maturation, modulating ovulation rate and modulating female fertility.

BACKGROUND OF THE INVENTION

Mammalian immature eggs (oocytes) grow and develop in follicles within the ovary. Immature oocytes are metabolically coupled to somatic granulosa cells, which surround the oocyte and nature the development of the oocyte until ovulation. The oocyte depends on its association with its companion somatic granulosa cells not only to support its growth and development, but also to regulate the progression of meiosis.

Follicle development is driven by a complex interaction between proliferation, differentiation and atresia. Atresia of ovarian follicles is an important process, accounting for the loss of over 99% of oocytes. It has been demonstrated from both in vivo and in vitro studies that follicular atresia is through an active process of programmed cell death, referred to as apoptosis. At the cellular level, apoptosis is characterized by cytoplasmic and nuclear fragmentation, chromatin condensation, DNA fragmentation and phagocytosis.

Apoptosis can be initiated in at least four different cell compartments in follicular development (theca cells, granulosa cells, cumulus cells and in the oocyte itself). During early atresia in antral follicles, the cumulus cells and the oocyte remain apparently unaffected by the atretic changes primarily manifested as apoptosis in the mural granulosa cells and, at a later stage, in the theca cells. The mechanism by which oocytes and granulosa/cumulus cells interact to escape apoptosis is poorly understood.

Traditionally it has been thought that the role of the oocyte in follicle development is passive, and that follicle development and therefore oogenesis, is driven by external hormones. However, it now appears that oocytes also secrete factors that promote follicle development. This oocyte control of folliculogenesis appears to be extremely important, as demonstrated by the fact that altered expression of oocyte paracrine factors can have profound effects on oocyte maturation, follicle development and fertility.

As such, the evidence now suggests that oocytes appear to play an active role in regulating follicle growth, and consequently follicle development and fertility, by secreting paracrine factors that regulate fundamental control elements of follicular granulosa cell function.

Despite the critical importance of such oocyte-secreted factors in regulating granulosa cell development, there is currently very little information regarding the identity of the factors secreted by oocytes that are involved in granulosa cell development, and how the expression of such factors can be used to control folliculogenesis, oocyte maturation and fertility.

In addition, the current methods for controlling folliculogenesis, oocyte maturation and fertility both in vitro and in vivo are inadequate for many reasons. Accordingly, there is a need for new methods of controlling granulosa cell development, so as to control follicle development, oocyte maturation and fertility.

The present invention arises from the finding that the apoptosis of granulosa cells is modulated by BMP-15 (also known as bone morphogenetic protein-15; GDF-9B) and/or BMP-6 (bone morphogenetic protein-6). Accordingly, the present invention relates to a method and composition for modulating the apoptosis of granulosa cells, and to methods and compositions for modulating oocyte maturation, follicle development and female fertility.

A reference herein to a patent document or other matter which is given as prior art is not to be taken as an admission that that document or matter was known or that the information it contains was part of the common general knowledge as at the priority date of any of the claims.

SUMMARY OF THE INVENTION

The present invention provides a method of modulating apoptosis of a granulosa cell, the method including one or more of the following steps:
  (i) modulating the concentration and/or activity of BMP-15 and/or BMP-6 that the granulosa cell is exposed to;
  (ii) modulating activity of a BMP-15 dependent signalling pathway in the granulosa cell; and
  (iii) modulating activity of a BMP-6 dependent signalling pathway in a granulosa cell.

The present invention also provides a method of preventing and/or treating a disease or condition associated with oocyte maturation and/or follicle maturation in a female subject, the method including one or more of the following steps:
  (i) modulating apoptosis of granulosa cells in the subject by modulating the concentration and/or activity of BMP-15 and/or BMP-6 that the granulosa cells are exposed to;
  (ii) modulating apoptosis of granulosa cells in the subject by modulating activity of a BMP-15 dependent signalling pathway in the granulosa cells; and
  (iii) modulating apoptosis of granulosa cells in the subject by modulating activity of a BMP-6 dependent signalling pathway in the granulosa cells.

The present invention also provides a method of modulating maturation of an oocyte, the method including one or more of the following steps:
  (i) modulating apoptosis of granulosa cells associated with the oocyte by modulating the concentration and/or activity of BMP-15 and/or BMP-6 that the granulosa cells are exposed to;
  (ii) modulating apoptosis of granulosa cells associated with the oocyte by modulating activity of a BMP-15 dependent signalling pathway in the granulosa cells; and
  (iii) modulating apoptosis of granulosa cells associated with the oocyte by modulating activity of a BMP-6 dependent signalling pathway in the granulosa cells.

The present invention also provides a method of modulating developmental competence of an oocyte, the method including one or more of the following steps:
  (i) modulating apoptosis of granulosa cells associated with the oocyte by modulating the concentration and or activity of BMP-15 and/or BMP-6 that the granulosa cells are exposed to;

(ii) modulating apoptosis of granulosa cells associated with the oocyte by modulating activity of a BMP-15 dependent signalling pathway in the granulosa cells; and (iii) modulating apoptosis of granulosa cells associated with the oocyte by modulating activity of a BMP-6 dependent signalling pathway in the granulosa cells.

The present invention also provides a method of modulating maturation of a follicle, the method including one or more of the following steps:

(i) modulating apoptosis of granulosa cells in the follicle by modulating the concentration and/or activity of BMP-15 and/or BMP-6 that the granulosa cells are exposed to;

(ii) modulating apoptosis of granulosa cells in the follicle by modulating activity of a BMP-15 dependent signalling pathway in the granulosa cells; and (iii) modulating apoptosis of granulosa cells in the follicle by modulating activity of a BMP-6 dependent signalling pathway in the granulosa cells.

The present invention also provides a method of modulating atresia of a follicle, the method including one or more of the following steps:

(i) modulating apoptosis of granulosa cells in the follicle by modulating the concentration and/or activity of BMP-15 and/or BMP-6 that the granulosa cells are exposed to;

(ii) modulating apoptosis of granulosa cells in the follicle by modulating activity of a BMP-15 dependent signalling pathway in the granulosa cells; and (iii) modulating apoptosis of granulosa cells in the follicle by modulating activity of a BMP-6 dependent signalling pathway in the granulosa cells.

The present invention also provides a method of modulating development of a follicle, the method including one or more of the following steps:

(i) modulating apoptosis of granulosa cells in the follicle by modulating the concentration and/or activity of BMP-15 and/or BMP-6 that the granulosa cells are exposed to;

(ii) modulating apoptosis of granulosa cells in the follicle by modulating activity of a BMP-15 dependent signalling pathway in the granulosa cells; and (iii) modulating apoptosis of granulosa cells in the follicle by modulating activity of a BMP-6 dependent signalling pathway in the granulosa cells.

The present invention also provides a method of modulating ovulation rate in a female subject, the method including one or more of the following steps:

(i) modulating apoptosis of granulosa cells in the subject by modulating the concentration and/or activity of BMP-15 and/or BMP-6 that the granulosa cells are exposed to;

(ii) modulating apoptosis of granulosa cells in the subject by modulating activity of a BMP-15 dependent signalling pathway in the granulosa cells; and (iii) modulating apoptosis of granulosa cells in the subject by modulating activity of a BMP-6 dependent signalling pathway in the granulosa cells.

The present invention also provides a method of modulating fertility in a female subject, the method including one or more of the following steps:

(i) modulating apoptosis of granulosa cells in the subject by modulating the concentration and/or activity of BMP-15 and/or BMP-6 that the granulosa cells are exposed to;

(ii) modulating apoptosis of granulosa cells in the subject by modulating activity of a BMP-15 dependent signalling pathway in the granulosa cells; and (iii) modulating apoptosis of granulosa cells in the subject by modulating activity of a BMP-6 dependent signalling pathway in the granulosa cells.

The present invention also provides a method of reducing granulosa cell apoptosis due to freeze-thawing, the method including one or more of the following steps:

(i) modulating the concentration and/or activity of BMP-15 and/or BMP-6 that the granulosa cell is exposed to;

(ii) modulating activity of a BMP-15 dependent signalling pathway in the granulosa cell; and (iii) modulating activity of a BMP-6 dependent signalling pathway in a granulosa cell.

The present invention also provides a method of reducing damage to a cumulus oocyte complex, follicle, ovarian tissue or ovary due to freeze-thawing, the method including exposing the cumulus oocyte complex, follicle, ovarian tissue or ovary to one or more of the following:

(i) an effective of BMP-15 and/or BMP-6;

(ii) an effective amount of an agent that modulates activity of a BMP-15 dependent signalling pathway in a granulosa cell in the cumulus oocyte complex, follicle, ovarian tissue or ovary; and (iii) an effective amount of an agent that modulates activity of a modulating activity of a BMP-6 dependent signalling pathway in a granulosa cell in the cumulus oocyte complex, follicle, ovarian tissue or ovary.

The present invention also provides a composition for modulating apoptosis of a granulosa cell, the composition including one or more of the following:

(i) an effective amount of BMP-15 and/or BMP-6;

(ii) an effective amount of an agent that modulates activity of a BMP-15 dependent signalling pathway in the granulosa cell; and (iii) an effective amount of an agent that modulates activity of a BMP-6 dependent signalling pathway in the granulosa cell.

The present invention also provides a medium for culturing of a cumulus oocyte complex and/or a follicle, the medium including one or more of the following:

(i) an effective amount of BMP-15 and/or BMP-6;

(ii) an effective amount of an agent that increases activity of a BMP-15 dependent signalling pathway in a granulosa cell in the cumulus oocyte complex or in the follicle; and (iii) an effective amount of an agent that increases activity of a BMP-6 dependent signalling pathway in a granulosa cell in the cumulus oocyte complex or in the follicle.

The present invention also provides a combination product including the following components:

an oocyte and/or embryo culture medium;

BMP-15 and/or BMP-6, or a variant or an analogue thereof; and/or an agent that modulates activity of a BMP-15 dependent signalling pathway in a granulosa cell; and/or an agent that modulates activity of a BMP-6 dependent signalling pathway in a granulosa cell;

wherein the components are provided in a form for addition of the components to the culture medium.

The present invention also provides a composition for modulating maturation of an oocyte, the composition including one or more of the following:

(i) an amount of BMP-15 and/or BMP-6 effective to modulate apoptosis of granulosa cells associated with the oocyte;

(ii) an amount of an agent effective to modulate apoptosis of granulosa cells associated with the oocyte by modulating activity of a BMP-15 dependent signalling pathway in the granulosa cells; and (iii) an amount of an agent effective to modulate apoptosis of granulosa cells associated with the oocyte by modulating the activity of a BMP-6 dependent signalling pathway in the granulosa cells.

The present invention also provides an oocyte in vitro maturation medium, the medium including one or more of the following:

(i) an effective amount of BMP-15 and/or BMP-6;

(ii) an effective amount of an agent that increases activity of a BMP-15 dependent signalling pathway in a granulosa cell associated with the oocyte; and (iii) an effective amount of an agent that increases activity of a BMP-6 dependent signalling pathway in a granulosa cell associated with the oocytes.

The present invention also provides a composition for modulating developmental competence of an oocyte, the composition including one or more of the following:

(i) an amount of BMP-15 and/or BMP-6 effective to modulate apoptosis of granulosa cells associated with the oocyte;

(ii) an amount of an agent effective to modulate apoptosis of granulosa cells associated with the oocyte by modulating activity of a BMP-15 dependent signalling pathway in the granulosa cells; and (iii) an amount of an agent effective to modulate apoptosis of granulosa cells associated with the oocyte by modulating the activity of a BMP-6 dependent signalling pathway in the granulosa cells.

The present invention also provides a medium for improving the developmental competence of an oocyte, the medium including one or more of the following:

(i) an effective amount of BMP-15 and/or BMP-6;

(ii) an effective amount of an agent that increases activity of a BMP-15 dependent signalling pathway in a granulosa cell associated with the oocyte; and (iii) an effective amount of an agent that increases activity of a BMP-6 dependent signalling pathway in a granulosa cell associated with the oocytes.

The present invention also provides a composition for preventing and/or treating in a female subject a disease or condition associated with oocyte maturation and/or follicle maturation, the composition including one or more of the following:

(i) an amount of BMP-15 and/or BMP-6 effective to modulate apoptosis of granulosa cells in the subject;

(ii) an amount of an agent effective to modulate apoptosis of granulosa cells in the subject by modulating activity of a BMP-15 dependent signalling pathway in the granulosa cells; and (iii) an amount of an agent effective to modulate apoptosis of granulosa cells in the subject by modulating the activity of a BMP-6 dependent signalling pathway in the granulosa cells.

The present invention also provides a composition for culturing a follicle, the composition including one or more of the following:

(i) an amount of BMP-15 and/or BMP-6 effective to modulate apoptosis of granulosa cells in the follicle;

(ii) an amount of an agent effective to modulate apoptosis of granulosa cells in the follicle by modulating activity of a BMP-15 dependent signalling pathway in the granulosa cells; and (iii) an amount of an agent effective to modulate apoptosis of granulosa cells in the follicle by modulating the activity of a BMP-6 dependent signalling pathway in the granulosa cells.

The present invention also provides a follicle culture medium, the medium including one or more of the following:

(i) an effective amount of BMP-15 and/or BMP-6;

(ii) an effective amount of an agent that increases activity of a BMP-15 dependent signalling pathway in a granulosa cell in the follicle; and (iii) an effective amount of an agent that increases activity of a BMP-6 dependent signalling pathway in a granulosa cell in the follicle.

The present invention also provides a composition for modulating atresia of a follicle, the composition including one or more of the following:

(i) an amount of BMP-15 and/or BMP-6 effective to modulate apoptosis of granulosa cells in the follicle;

(ii) an amount of an agent effective to modulate apoptosis of granulosa cells in the follicle by modulating activity of a BMP-15 dependent signalling pathway in the granulosa cells; and (iii) an amount of an agent effective to modulate apoptosis of granulosa cells in the follicle by modulating the activity of a BMP-6 dependent signalling pathway in the granulosa cells.

The present invention provides a composition for modulating development of a follicle, the composition including one or more of the following:

(i) an amount of BMP-15 and/or BMP-6 effective to modulate apoptosis of granulosa cells in the follicle;

(ii) an amount of an agent effective to modulate apoptosis of granulosa cells in the follicle by modulating activity of a BMP-15 dependent signalling pathway in the granulosa cells; and (iii) an amount of an agent effective to modulate apoptosis of granulosa cells in the follicle by modulating activity of a BMP-6 dependent signalling pathway in the granulosa cells.

The present invention also provides a composition for modulating ovulation rate in a female subject, the composition including one or more of the following:

(i) an amount of BMP-15 and/or BMP-6 effective to modulate apoptosis of (granulosa cells in the subject;

(ii) an amount of an agent effective to modulate apoptosis of granulosa cells in the subject by modulating activity of a BMP-15 dependent signalling pathway in the granulosa cells; and (iii) an amount of an agent effective to modulate apoptosis of granulosa cells in the subject by modulating activity of a BMP-6 dependent signalling pathway in the granulosa cells.

The present invention also provides a composition for modulating the number of follicles that mature each ovarian or menstrual cycle in a female subject the composition including one or more of the following:

(i) an amount of BMP-15 and/or BMP-6 effective to modulate apoptosis of granulosa cells in the subject;

(ii) an amount of an agent effective to modulate apoptosis of granulosa cells in the subject by modulating activity of a BMP-15 dependent signalling pathway in the granulosa cells; and (iii) an amount of an agent effective to modulate apoptosis of granulosa cells in the subject by modulating activity of a BMP-6 dependent signalling pathway in the granulosa cells.

The present invention also provides a composition for modulating fertility in a female subject, the composition including one or more of the following:
(i) an amount of BMP-15 and/or BMP-6 effective to modulate apoptosis of granulosa cells in the subject;
(ii) an amount of an agent effective to modulate apoptosis of granulosa cells in the subject by modulating activity of a BMP-15 dependent signalling pathway in the granulosa cells; and
(iii) an amount of an agent effective to modulate apoptosis of granulosa cells in the subject by modulating activity of a BMP-6 dependent signalling pathway in the granulosa cells.

The present invention also provides an oocyte in vitro maturation medium, the medium including one or more of the following:
(i) BMP-15 and/or BMP-6;
(ii) an agent that inhibits apoptosis of a granulosa cell associated with the oocyte by modulating activity of a BMP-15 dependent signalling pathway in the granulosa cell; and
(iii) an agent that inhibits apoptosis of a granulosa cell associated with the oocyte by modulating the activity of a BMP-6 dependent signalling pathway in the granulosa cell;

The present invention provides a medium for culturing of a cumulus oocyte complex and/or a follicle, the medium including one or more of the following:
(i) an effective amount of BMP-15 and/or BMP-6;
(ii) an effective amount of an agent that increases activity of a BMP-15 dependent signalling pathway in a granulosa cell in the cumulus oocyte complex or in the follicle; and
(iii) an effective amount of an agent that increases activity of a BMP-6 dependent signalling pathway in a granulosa cell in the cumulus oocyte complex or in the follicle;
wherein the medium is substantially free of serum, albumin, follicular fluid, fetuin, follicle stimulating hormone (FSH), and anti-apoptotic growth factors.

The present invention also provides an oocyte it vitro maturation medium, the medium including one or more of the following components
(i) BMP-15 and/or BMP-6;
(ii) an agent that inhibits apoptosis of one or more granulosa cells associated with the oocyte by modulating activity of a BMP-15 dependent signalling pathway in the one or more granulosa cells; and
(iii) an agent that inhibits apoptosis of the one or more granulosa cells associated with the oocyte by modulating the activity of a BMP-6 dependent signalling pathway in the one or more granulosa cells;
wherein the medium is substantially free of serum, albumin, follicular fluid, fetuin, follicle stimulating hormone (FSH), and anti-apoptotic growth factors.

The present invention also provides a follicle culture medium, the medium including one or more of the following components:
(i) BMP-15 and/or BMP-6;
(ii) an agent that inhibits apoptosis of one or more granulosa cells in the follicle by modulating activity of a BMP-15 dependent signalling pathway in the one or more granulosa cells; and
(iii) an agent that inhibits apoptosis of the one or more granulosa cells in the follicle by modulating the activity of a BMP-6 dependent signalling pathway in the one or more granulosa cells;
wherein the composition is substantially free of serum, albumin, follicular fluid, fetuin, follicle stimulating hormone (FSH), and anti-apoptotic growth factors.

The present invention also provides a composition or medium including one or more of the following:
(i) BMP-15 and/or BMP-6;
(ii) an agent that inhibits apoptosis of a granulosa cell by modulating activity of a BMP-15 dependent signalling pathway in the granulosa cell; and
(iii) an agent that inhibits apoptosis of a granulosa cell by modulating the activity of a BMP-6 dependent signalling pathway in the granulosa cell;
the composition further including 40 mM to 400 mM NaCl, 0.1 mM to 20 mM KCl, and 0.1 mM to 40 mM glucose.

The present invention also provides a composition for reducing granuloma cell apoptosis due to freeze-thawing, the composition including one or more of the following:
(i) active BiNAP-15 and/or active BMP-6;
(ii) an agent that increases activity of a BMP-15 dependent signalling pathway in the granulosa cell; and
(iii) an agent that increases activity of a BMP-6 dependent signalling pathway in a granulosa cell.

The present invention provides a composition for reducing damage to a cumulus oocyte complex, follicle, ovarian tissue or ovary due to freezing, the composition including one or more of the following:
(i) an effective amount of active BMP-15 and/or active BMP-6;
(ii) an effective amount of an agent that increases activity of a BMP-15 dependent signalling pathway in a granulosa cell in the cumulus oocyte complex, follicle, ovarian tissue or ovary; and
(iii) an effective amount of an agent that increases activity of a BMP-6 dependent signalling pathway in a granulosa cell in the cumulus oocyte complex, follicle, ovarian tissue or ovary.

The present invention also provides a method of assisted reproduction involving an oocyte, the method including the step of culturing the oocyte in a medium including one or more of the following components:
(i) BMP-15 and/or BMP-6;
(ii) an agent that inhibits apoptosis of one or more granulosa cells associated with the oocyte by modulating activity of a BMP-15 dependent signalling pathway in the one or more granulosa cells; and
(iii) an agent that inhibits apoptosis of one or more granulosa cells associated with the oocyte by modulating the activity of a BMP-6 dependent signalling pathway in the one or more granulosa cells.

The present invention also provides a method of assisted reproduction involving an embryo produced from an oocyte, the method including the step of culturing the oocyte and/or the embryo in a medium including one or more of the following components:
(i) BMP-15 and/or BMP-6;
(ii) an agent that inhibits apoptosis of one or more granulosa cells associated with the oocyte by modulating activity of a BMP-15 dependent signalling pathway in the one or more granulosa cells; and
(iii) an agent that inhibits apoptosis of one or more granulosa cells associated with the oocyte by modulating the activity of a BMP-6 dependent signalling pathway in the one or more granulosa cells.

The present invention also provides a method of in vitro fertilization of an oocyte, the method including the step of culturing the oocyte in a medium including one or more of the following components:

(i) BMP-5 and/or BMP-6;

(ii) an agent that inhibits apoptosis of one or more granulosa cells associated with the oocyte by modulating activity of a BMP-15 dependent signalling pathway in the one or more granulosa cells; and (iii) an agent that inhibits apoptosis of one or more granulosa cells associated with the oocyte by modulating the activity of a BMP-6 dependent signalling pathway in the one or more granulosa cells.

The present invention also provides a method of assessing the developmental competence of an oocyte, the method including the steps of:

(i) determining the extent of apoptosis in granulosa cells associated with the oocyte; and (ii) assessing the developmental competence of the oocyte by the extent of apoptosis found in the granulosa cells associated with the oocyte;

wherein a decreased level of apoptosis is indicative of an oocyte with increased developmental competence, and an increased level of apoptosis is indicative of an oocyte with reduced developmental competence.

The present invention also provides a method of assessing the developmental competence of an oocyte, the method including the steps of:

(i) determining one or more of: the concentration and/or activity of BMP-15 and/, or BMP-6 that a granulosa cell associated with the oocyte is exposed to; determining the level of activity of a BMP-15 dependent signalling pathway in a granulosa cell associated with the oocyte; and determining the level of activity of a BMP-6 dependent signalling pathway in a granulosa cell associated with the oocyte; and (ii) assessing the developmental competence of the oocyte by the results of the above determinations;

wherein an increased concentration and/or activity of the BMP-15 and/or BMP-6, and/or an increased activity of the BMP-15 and/pr BMP-6 dependent signalling pathways is indicative of an oocyte with increased developmental competence, and a decreased concentration and/or activity of the BMP-15 and/or BMP-6, and/or a decreased activity of the BMP-15 and/pr BMP-6 dependent signalling pathways is indicative of an oocyte with reduced developmental competence.

The present invention also provides a method for assessing the developmental competence of an oocyte, the method including the steps of (i) determining the level of expression of BMP-15 and/or BMP-6 in the oocyte and/or determining the concentration of BMP-15 and/or BMP-6 secreted by the oocyte; and (ii) assessing the developmental competence of the oocyte;

wherein an increased expression and/or concentration of BMP-15 and/or BMP-6 is indicative of an oocyte with increased developmental competence, and a decreased expression and/or concentration of BMP-115 and/or BMP-6 is indicative of an oocyte with reduced developmental competence.

The present invention arises out of studies into the effects of oocyte-secreted factors on cumulus cell apoptosis. In particular, it has been found that the presence of the oocyte in the cumulus-oocyte complex (COC) is responsible for the low level of apoptosis in cumulus cells, and that removal of the oocyte from the cumulus-oocyte complex (oocytectomized complex; OOX) leads to a significant increase in apoptosis. Furthermore, the oocyte-secreted factors BMP-15 and BMP-6 can inhibit cumulus cell apoptosis in the ooctectomized complexes.

These findings demonstrate that BMP-15 and/or BMP-6 play a key role it regulating apoptosis in cumulus cells, and that these factors or the signalling pathways under the control of these factors may be used to control in vitro or in vivo apoptosis in granulosa cells and thereby control oocyte maturation, follicle development, ovulation rate, the number of follicles that mature during each ovarian or menstrual cycle, and fertility.

Various terms that will be used throughout the specification have meanings that will be well understood by a skilled addressee. However, for ease of reference, some of these terms will now be defined.

The term "nucleic acid" as used throughout the specification is to be understood to mean to any oligonucleotide or polynucleotide. The nucleic acid may be DNA or RNA and may be single stranded or double stranded. The nucleic acid may be any type of nucleic acid, including a nucleic acid of genomic origin, cDNA origin (ie derived from a mRNA), derived from a virus, or of synthetic origin.

The term "polypeptide" as used throughout the specification is to be understood to mean two or more amino acids joined by peptide bonds. Similarly, the term "amino acid sequence" refers to an oligopeptide, peptide, polypeptide, or protein sequence, and fragments or portions thereof, and to naturally occurring, recombinant, mutated or synthetic polypeptides.

The term "modulating" as used throughout the specification is to be understood to mean any inhibition or augmentation of a process, or any inhibition or augmentation of the activity, function or characteristic of a particular entity.

In this regard, the modulation of granulosa cell apoptosis in the various forms of the present invention is any form of control or change of the initiation or progression of apoptosis in the cell. For example, regulation of apoptosis may involve (i) reducing or promoting the ability of a cell to enter apoptosis; (ii) reducing or promoting the progression of apoptosis in a cell after apoptosis has begun; and/or (iii) reducing or promoting the probability that a particular cell will begin or progress through apoptosis.

The term "follicle development" and variants thereof as used throughout the specification is to be understood to mean the progression of an ovarian follicle through the stages of a primordial follicle to a preovulatory follicle through to the corpus luteum. In this regard, it will be understood that the follicle may be present in an entire female subject, or alternatively may be present in vitro, such as a follicle isolated from a female subject.

The term "oocyte maturation" and variants thereof as used throughout the specification is to be understood to mean the process whereby an oocyte progresses from a meiotically immature state, being incapable of being fertilised, to an oocyte that is meiotically mature, being fertilisable and capable of producing a viable embryo. The term will be understood to also include maturation of oocyte cytoplasm, such that the oocyte is able to support embryo development post-fertilization. In this regard, it will be understood that the oocyte may be present in an entire female subject, or alternatively may be present in vitro, such as an oocyte isolated from a female subject.

The term "associated with" and variants thereof as used throughout the specification in relation to cells of one type associated with cells of another type is to be understood to mean a cell in direct contact with another type of cell, or a cell in the presence of another type of cell, such that the cell may be acted upon by factors secreted from the other type of cell. For example, in the case of a oocyte associated with a granulosa cell, it will be understood that this includes for example an oocyte as part of a cumulus oocyte complex, or a denuded oocyte present in the same medium as a granulosa cell, a cumulus oocyte complex or an oocytectomised complex.

The term "variant" as used throughout the specification in relation to a polypeptide or protein is to be understood to mean an amino acid sequence that is altered by one or more amino acids. The variant may have "conservative" changes, wherein a substituted amino acid has similar structural or chemical properties to the replaced amino acid (e.g., replacement of leucine with isoleucine). A variant may also have "non-conservative" changes (e.g., replacement of a glycine with a tryptophan) or a deletion and/or insertion of one or more amino acids.

A variant may also be a biologically active fragment of the full size protein, being a polypeptide or protein having similar structural, regulatory, or biochemical functions as that of the full size polypeptide or protein. For example, a biologically active fragment may be an amino or carboxy terminal deletion of a protein, an internal deletion of a protein, or any combination of such deletions. A biologically active fragment will also include any such deletions fused to one or more additional amino acids.

The term "antibody" as used throughout the specification is to be understood to mean monoclonal or polyclonal antibodies, and fragments of antibody molecules, such as Fab, $F(ab')_2$, and Fv, which are capable of binding an epitopic determinant.

The term "isolated" as used throughout the specification in reference to a particular cell is to be understood to mean that the cell has been identified and separated and/or recovered from one or more components of its natural environment. For example, an isolated oocyte may be associated with one or more cumulus cells, be present as part of an cumulus-oocyte complex or may be a denuded oocyte.

The term "female subject" as used throughout the specification is to be understood to mean a female human, a female mammal including a primate, a livestock animal (eg. horses, cattle, sheep, pigs, goats), a companion animal (eg. dogs, cats), a laboratory test animals (eg. mice, rats, guinea pigs), or any other female animal in which apoptosis of granulosa cells occurs under the control of BMP-15 and/or BMP-6.

The term "assisted reproduction" as used throughout the specification is to be understood to mean any fertilization technique in humans and animals involving isolated oocytes and/or isolated sperm, including a technique using an oocyte or embryo cultured in vitro (for example in vitro maturation of an oocyte), in vitro fertilization (IVF; aspiration of an oocyte, fertilization in the laboratory and transfer of the embryo into a recipient), gamete intrafallopian transfer (GIFT; placement of oocytes and sperm into the fallopian tube), zygote intrafallopian transfer (ZIFT; placement of fertilized oocytes into the fallopian tube), tubal embryo transfer (TET; the placement of cleaving embryos into the fallopian tube), peritoneal oocyte and sperm transfer (POST; the placement of oocytes and sperm into the pelvic cavity), intracytoplasmic sperm injection (ICSI), testicular sperm extraction (TESE), and microsurgical epididymal sperm aspiration (MESA).

BRIEF DESCRIPTION OF THE FIGURES

FIGS. 7A and 7B show the effect of BMP antagonists on cumulus cell apoptosis. OOX were cultured with 10% v/v BMP-15 in the presence of increasing doses of follistatin (0-100 µg/ml) (A), and OOX were cultured with 10 ng/ml BMP-6 in the absence or presence of a high neutralizing dose of 20 µg/ml of a BMP-6 neutralizing antibody (NAb) (B). Suppression of cumulus cell apoptosis by BMP-15 was antagonized by follistatin. The NAb effectively antagonized the anti-apoptotic effects of BMP-6. Points and bars represent average percentage of apoptotic cumulus cells (mean±SEM). Values from points with different labels $^{a,\ b,\ c}$ differ significantly ($p<0.001$).

FIGS. 8A and 8B show the role of BMP-15 and BMP-6 in the anti-apoptotic actions of oocytes on cumulus cells. OOX co-cultured with denuded oocyte (25 DOs) were treated with 50 μg/ml follistatin, 20 μg/ml BMP-6 NAb, or a combination of the two (A). Both follistatin and the BMP-6 NAb were effective at partially antagonizing the anti-apoptotic effects of oocytes, however neither completely restored apoptosis to OOX levels, either alone or combined. Co-culturing OOX with DO or treatment with BMP-15 alone or BMP-6 alone decreased cumulus cell apoptosis (B). Combined treatment of OOXs with BMP-6 and BMP-15 did not further decrease apoptosis levels beyond that of BMP-15 alone, suggesting no additive effect of these two BMPs. Bars represent average percentage of apoptotic cumulus cells (mean±SEM). Values from bars with different labels [a, b, c] differ significantly ($p<0.001$).

FIGS. 9A and 9B show the effect of BMP-7 and its antagonist gremlin on cumulus cell apoptosis. OOX was cultured with 10% BMP-15 in the presence of increasing doses of gremlin (0-40 μg/ml) (A). OOX were also co-cultured with 100 ng/ml BMP-7 and/or 10% BMP-15 in the presence or absence of 2 μg/ml gremlin (B). Gremlin did not antagonize the suppression effect of BMP-15 on cumulus cell apoptosis, whereas it did that of BMP-7. Bars and points represent average percentage of apoptotic cumulus cells (mean±SEM). Values from bars with different labels [a, b, c] differ significantly ($p<001$).

GENERAl DESCRIPTION OF THE INVENTION

Figure 1A:
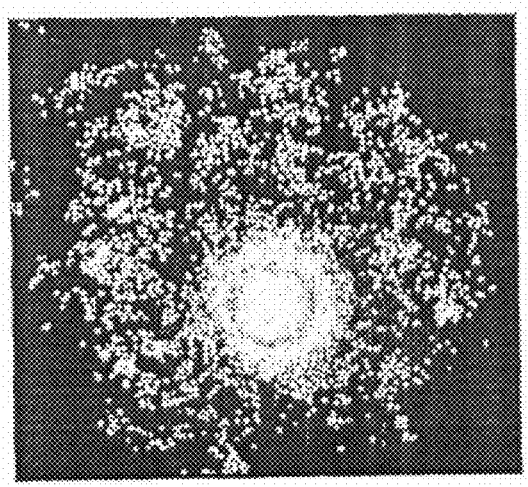
FIGS. 1A to 1D show representative images of confocal laser scanning microscopy of DNA fragmentation in cumulus cells, as detected by TUNEl (green label). All cell nuclei are also stained with propidium iodide (red). Positive control DNAse 1-treated OOX showed very strong apoptotic staining (99%) (A), negative control did not reveal any apoptotic signals (0%) indicating specific labelling (B), COC with low apoptotic labelling (9%) (C), compared to OOX with higher apoptotic labelling (35%) (D).

As mentioned above, in one form the present invention provides a method of modulating apoptosis of a granulosa cell, the method including one or more of the following steps:
(i) modulating the concentration and/or activity of BMP-15 and/or BMP-6 that the granulosa cell is exposed to;
(ii) modulating activity of a BMP-15 dependent signalling pathway in the granulosa cell; and
(iii) modulating activity of a BMP-6 dependent signalling pathway in a granulosa cell.

In this form of the present invention, apoptosis of a granulosa cell may be inhibited or promoted by (i) modulating the concentration and/or activity of BMP-15 and/or BMP-6 that the granulosa cell is exposed to; and/or (ii) modulating the activity of a BMP-15 dependent signalling pathway in the granulosa cell; and/or (iii) modulating the activity of a BMP-6 dependent signalling pathway in the granulosa cell.

For example, the method of this form of the present invention may be used to inhibit the apoptosis of granulosa cells by exposing granulosa cells to an increased concentration of BMP-15 and/or BMP-6. Alternatively, the apoptosis of granulosa cells may be promoted by reducing the concentration of BMP-15 and/or BMP-6 that the granulosa cells are exposed to.

In this regard, BMP-15 and BMP-6 are both members of the transforming growth factor beta (TGF-β) superfamily, which includes large families of growth and differentiation factors. These proteins are synthesized as prepropeptides, cleaved, and then processed into dimeric proteins. BMP-15 binds to the AlK-6 and BMPR-II receptors, while BMP-6 binds to the ActRII and BMPR-II receptors.

In die case of BMP-15, this protein may form both homodimers, and also heterodimers with GDF-9.

The present invention also provides a granulosa cell with altered apoptosis or apoptotic potential produced according to this method. The granulosa cell may be for example an isolated granulosa cell, a granulosa cell present in vivo, a granulosa cell present in a follicle in vivo or in vitro, a granulosa cell as part of a cumulus oocyte complex in vitro or in vivo, a or granulosa cell as part of an oocytectomised complex.

The present invention is also suitable for preventing and/or treating a disease or condition associated with oocyte maturation and/or follicle maturation in a female subject, by modulating the level of apoptosis in granulosa cells. Accordingly, in another form the present invention provides a method of preventing and/or treating a disease or condition associated with oocyte maturation and/or follicle maturation in a female subject, the method including one or more of the following steps:
(i) modulating apoptosis of granulosa cells in the subject by modulating the concentration and/or activity of BMP-15 and/or BMP-6 that the granulosa cells are exposed to;
(ii) modulating apoptosis of granulosa cells in the subject by modulating activity of a BMP-15 dependent signalling pathway in the granulosa cells; and
(iii) modulating apoptosis of granulosa cells in die subject by modulating activity of a BMP-6 dependent signalling pathway in the granulosa cells.

For example, the present invention may used to prevent and/or treat a granulosa cell tumour or polycystic ovary syndrome in a female subject.

The present invention is also suitable for modulating the maturation of an oocyte, by modulating the level of apoptosis in granulosa cells associated with the oocyte.

Accordingly, in another form the present invention provides a method of modulating maturation of an oocyte, the method including one or more of the following steps:
(i) modulating apoptosis of granulosa cells associated with the oocyte by modulating the concentration and/or activity of BMP-15 and/or BMP-6 that the granulosa cells are exposed to;
(ii) modulating apoptosis of granulosa cells associated with the oocyte by modulating activity of a BMP-15 dependent signalling pathway in the granulosa cells; and
(iii) modulating apoptosis of granulosa cells associated with the oocyte by modulating activity of a BMP-6 dependent signalling pathway in the granulosa cells.

The present invention also provides an oocyte with altered maturation produced according to this method. The oocyte may be for example an isolated oocyte, a oocyte present in vivo, an oocyte as part of a cumulus oocyte complex in vitro or in vivo, or an oocyte as part of a follicle in vitro or in vivo. The present invention also contemplates embryos and non-human animals produced from the oocyte.

In this case, it will be appreciated that this method is particularly suitable for modulating maturation of an oocyte in vitro.

The present invention is also suitable for modulating the developmental competence of an oocyte, by modulating the level of apoptosis in granulosa cells associated with the oocyte.

Accordingly, in another form the present invention provides a method of modulating developmental competence of an oocyte, the method including one or more of the following steps:

(i) modulating apoptosis ofl granulosa cells associated with the oocyte by modulating the concentration and/or activity of BMP-15 and/or BMP-6 that the granulosa cells are exposed to;
(ii) modulating apoptosis of granulosa cells associated with the oocyte by modulating activity of a BMP-15 dependent signalling pathway in the granulosa cells; and
(iii) modulating apoptosis of granulosa cells associated with the oocyte by modulating activity of a BMP-6 dependent signalling pathway in the granulosa cells.

The present invention also provides an oocyte with altered developmental competence produced according to this method. The oocyte may be for example an oocyte in vitro or in vivo as part of a cumulus oocyte complex or an oocyte present in a follicle. The present invention also contemplates embryos and non-human animals produced from the oocyte.

In this case, it will be appreciated that this method is particularly suitable for modulating developmental competence of an oocyte in vitro.

The present invention is also suitable for modulating the maturation of a follicle, by modulating the level of apoptosis in granulosa cells in the follicle.

Accordingly, in another form the present invention provides a method of modulating maturation of a follicle, the method including one or more of the following steps:
(i) modulating apoptosis of granulosa cells in the follicle by modulating the concentration and/or activity of BMP-15 and/or BMP-6 that the granulosa cells are exposed to;
(ii) modulating apoptosis of granulosa cells in the follicle by modulating activity of a BMP-15 dependent signalling pathway in the granulosa cells, and
(iii) modulating apoptosis of granulosa cells in the follicle by modulating activity of a BMP-6 dependent signalling pathway in the granulosa cells.

The present invention also provides a follicle with altered maturation produced according to this method. The follicle may be for example an isolated follicle, or a follicle present in vivo. The present invention also contemplates oocytes isolated from the follicle, and embryos and non-human animals produced from the oocyte.

In this case, it will be appreciated that this method is particularly suitable for modulating maturation of a follicle in vitro.

The present invention is also suitable for modulating follicle atresia, by modulating the level of granulosa cell apoptosis.

Accordingly, in another form the present invention provides a method of modulating atresia of a follicle, the method including one or more of the following steps:
(i) modulating apoptosis of granulosa cells in the follicle by modulating the concentration and/or activity of BMP-15 and/or BMP-6 that the granulosa cells are exposed to;
(ii) modulating apoptosis of granulosa cells in the follicle by modulating activity of a BMP-15 dependent signalling pathway in the granulosa cells, and
(iii) modulating apoptosis of granulosa cells in the follicle by modulating activity of a BMP-6 dependent signalling pathway in the granulosa cells.

The present invention also provides a follicle with altered atresia produced according to this method. The follicle may be an isolated follicle, or a follicle present in vivo. The present invention also contemplates oocytes isolated from the follicle, and embryos and non-human animals produced from the oocyte.

In a preferred form, the present invention provides the modulation of follicular atresia in a female subject.

The present invention is also suitable for modulating the development of a follicle by modulating the level of apoptosis of granulosa cells in the follicle.

Accordingly, in another form the present invention provides a method of modulating development of a follicle, the method including one or more of the following steps:
(i) modulating apoptosis of granulosa cells in the follicle by modulating the concentration and/or activity of BMP-15 and/or BMP-6 that the granulosa cells are exposed to;
(ii) modulating apoptosis of granulosa cells in the follicle by modulating activity of a BMP-15 dependent signalling pathway in the granulosa cells; and
(iii) modulating apoptosis of granulosa cells in the follicle by modulating activity of a BMP-6 dependent signalling pathway in the granuloma cells.

The present invention also provides a follicle with altered development or developmental potential produced according to this method. The follicle may be an 4 isolated follicle, or a follicle present in vivo. The present invention also contemplates oocytes isolated from the follicle, and embryos and non-human animals produced from the oocyte.

The present invention is also suitable for modulating ovulation rate in a female subject by modulating the level of apoptosis of granulosa cells in the subject.

Accordingly, in another form the present invention provides a method of modulating ovulation rate in a female subject, the method including one or more of the following steps:
(i) modulating apoptosis of granulosa cells in the subject by modulating the concentration and/or activity of BMP-15 and/or BMP-6 that the granulosa cells are exposed to;
(ii) modulating apoptosis of granulosa cells in the subject by modulating activity of a BMP-15 dependent signalling pathway in the granulosa cells; and
(iii) modulating apoptosis of granulosa cells in the subject by modulating activity of a BMP-6 dependent signalling pathway in the granulosa cells.

Methods are known in the art for determining ovulation rate in a female subject.

The present invention is also suitable for modulating fertility in a female subject by modulating the level of apoptosis of granulosa cells in the subject.

Accordingly, in another form the present invention provides a method of modulating fertility in a female subject, the method including one or more of the following steps:
(i) modulating apoptosis of granulosa cells in the subject by modulating the concentration and/or activity of BMP-15 and/or BMP-6 that the granulosa cells are exposed to;
(ii) modulating apoptosis of granulosa cells in the subject by modulating activity of a BMP-15 dependent signalling pathway in the granulosa cells: and
(iii) modulating apoptosis of granulosa cells in the subject by modulating activity of a BMP-6 dependent signalling pathway in the granulosa cells.

It will be appreciated that the present invention may be used to promote fertility, or alternatively, be used as a contraceptive method.

The granulosa cell in the various forms of the present invention is any granulosa cell present in vitro or in vivo. For example, the granulosa cell may be an isolated granulosa cell in cell culture, a granulosa cell that is associated with one or more other cell types in cell culture, a granulosa cell that is pan of a cumulus-oocyte complex, a granulosa cell that is part of an oocytectomized complex, a granulosa cell present in a follicle in vitro, or a granulosa cell present in vivo that forms part of a follicle in a female mammal.

In the case of a granulosa cell in vitro, preferably the granulosa cell is associated with an oocyte. More preferably, the granulosa cell is a cumulus cell. Most preferably, the granulosa cell is a cumulus cell present in a cumulus-oocyte complex.

The granulosa cell in the various forms of the present invention may also be pre-granulosa cell, a preantral granulosa cell, a mural granulosa cell, a cumulus granulosa cell, a granulosa-lutein cell, or a compact or expanded cumulus granulosa cell.

In the case of a granulosa cell in vivo, the granulosa cell may for example form part of a follicle in a female subject.

It will be appreciated that the modulation of apoptosis in the various forms of the present invention may occur at any time prior to, during and after fertilization of an oocyte in vitro or in vivo associated with the granulosa cell.

Preferably, the modulation of apoptosis occurs prior to fertilization.

Preferably, the granulosa cell is a granulosa cell from a female mammal, or a granulosa cell that forms part of a follicle present in a female mammal, including a human granulosa cell, a non-human primate granulosa cell, an ovine granulosa cell, a bovine granulosa cell, a porcine granulosa cell, an equine granulosa cell, a caprine granulosa cell, a feline granulosa cell, a rodent granulosa cell, a canine granulosa cell or a murine granulosa cell. Preferably, the granulosa cell is a human granulosa cell, a bovine granulosa cell, an ovine granulosa cell or an equine granulosa cell.

For a granulosa cell present in vitro, the granulosa cell may be obtained from a suitable donor in any phase of folliculogenesis or from a suitable donor in a superovulated state, by a suitable method known in the art. A suitable method for obtaining granulosa cells for in vitro purposes is as described in Gilchrist R B et al (2001) *Developmental Biology* 240:289-298 (for mouse cells), and Gilchrist R B et al (2003) *Molecular, Cellular Endocrinology* 201: 87-95 (for ruminant cells). For example, granulosa cells may be isolated from immature or mature ovaries, hormonally stimulated or unstimulated, and the granulosa cells collected by puncturing or aspirating antral follicles or enzymatically digesting ovaries, followed by granulosa cell purification/enrichment by removing debris and centrifugation.

The extent of granulosa cell apoptosis in the various forms of the present invention may be determined by a suitable known in art, including (i) DNA fragmentation assays, for example terminal deoxynucleotidyl transferase-mediated dUTP nick end labeling (TUNEl), which is an in situ method for detecting the 3'-OH ends of DNA exposed during the internucleosomal cleavage that occurs during apoptosis, and which may be performed essentially as described in Hensey C. and Gautier J. (1998). *Dev. Biol.* 203, 36-48; Veenstra, G J, Peterson-Maduro J, Mathu M T, van der Viet P C, Destree O H J. (1998). *Cell Death Differ* 5:774-84; (ii) detection of morphological changes associated with apoptosis, essentially as described in Compton M M (1992) *Cancer Metast Rev* 11:105-119, 1992; Wyllie A H (1992) *Cancer Metast Rev* 11: 95-103; Oltvai Z N, Korsmeyer S J (1994) *Cell* 79:189-192, 1994; or (iii) use of flow cytometry analysis to detect apoptosis, essentially as described in Ormerod M G, Collins M K l, Rodriguez-Tarduchy G. Robertson D (1992) *J Immunol Meth* 153:57-66; Jacobs D P, Pipho C (1983) *J Immunol Meth* 62: 101-10.

For a granulosa cell present in vivo, the extent of apoptosis of a granulosa cell may be determined by a suitable method known in the art. For example, the expression of pro-apoptotic proteins (such as Bax) or anti-apoptotic proteins (such as Bcl-2) may be determined by Western analysis.

As discussed previously, the present invention may also be used to prevent and/or treat a disease or condition associated with associated with oocyte maturation and/or follicle maturation in a female subject. For example, the present invention may be used to prevent and/or treat a granulosa cell tumour by increasing the level of apoptosis in the tumorigenic cells. Alternatively, the present invention may be used to prevent and/or treat polycystic ovary syndrome.

It will be appreciated that administration to the subject of BMP-15 and/or BMP-6, and/or an agent that modulates the activity of a BMP-15 or BMP-6 dependent signalling pathway in granulosa cells may at any one of before, during and after onset of the disease or condition.

In addition some treatments, such as chemotherapy, result in an increased level of follicle atresia. Accordingly, the present invention may be used to ameliorate such conditions by reducing the level of granulosa cell apoptosis in the subject being treated. In this case, reducing the level of apoptosis of granulosa cells in a subject may be used at any one of before, during and/or after treatment to reduce atresia.

Modulating the concentration and/or activity of BMP-15 and/or BMP-6 that a granulosa cell is exposed to may be achieved in a number of different ways. For example, in the case of increasing the concentration of one or both of these proteins, the granulosa cells may be exposed to, or contacted with, the proteins.

In this regard, it will be appreciated that the reference to BMP-15 includes the protein from a suitable species to modulate apoptosis in the target granulosa cell(s) (including the use of the protein from the same species as that of the granulosa cell for which apoptosis is to be modulated), a variant of the protein (such as a form of the protein with one or more amino acid substitutions from that of the wildtype), or a biologically active fragment of the protein. The protein may be an isolated protein, a recombinant protein, purified or semi-purified, or as part of a complex mixture of proteins (such as occurs in conditioned medium from oocytes).

Similarly, the reference to BMP-6 includes the protein from a suitable species to modulate apoptosis in the target granulosa cell(s) (including the use of the protein from the same species as that of the granulosa cell for which apoptosis is to be modulated), a variant of the protein (such as a form of the protein with one or more amino acid substitutions from that of the wildtype), or a biologically active fragment of the protein. The protein may be an isolated protein, a recombinant protein, purified or semi-purified, or as part of a complex mixture of proteins (such as occurs in conditioned medium from oocytes).

As discussed above, the proteins may be delivered as purified, semi-purified proteins, or in the form of oocyte-conditioned medium and/or oocyte-secreted factors. Methods for producing the proteins are known in the art. For example, the proteins may be delivered in the form of an extract containing one or more other components, such by exposing a granulosa cell to a conditioned medium containing BMP-15 and/or BMP-6 secreted from an oocyte.

In the case of decreasing the concentration and/or activity of BMP-15 and/or BMP-6, a decrease in activity may be accomplished for example by exposing the granulosa cell to a media containing a reduced concentration of the proteins, or by use of a neutralizing antibody to either of these proteins.

Other methods of reducing the concentration or activity of the proteins include the use of the ectodomain of the AlK6 and/or BPMPRII receptors. Follistatin may be used to reduce the concentration of BMP-15, by forming an inactive complex with this molecule.

Antisense nucleic acids and siRNA technologies may also be used to modulate expression of BMP-15 and BMP-6 in an oocyte and thereby modulate the level of these proteins secreted by an oocyte. Accordingly, the present invention contemplates in one form the addition of an antisense nucleic acid or siRNA to an oocyte to reduce the expression of BMP-15 and/or BMP-6 in the follicle, thereby increasing the extent of apoptosis in granulosa cells associated with the oocyte. Methods are known in the art for the design and administration of antisense nucleic acids and siRNAs.

It will be appreciated that an agent that promotes or interferes with the gradient of oocyte secreted factors involved in regulating apoptosis in the cumulus oocyte complex may also be used to modulate the level of granulosa cell apoptosis.

It will also be appreciated that other factors may be used to further modulate the level of apoptosis in the granulosa cell. For example, exposure of cells to FSH may be used to decrease the incidence of apoptosis.

Preferably, the modulation of the activity of the BMP-15 or the BNP-6 dependent signalling pathways is modulation of the AlK6 and/or BMPRII receptor signalling pathways.

In this regard, modulation of the AlK6 and/or BMPRII pathways results in a modulation of the SMAD 1/5/8 pathway in the cell.

Modulating the activity and/or concentration of GDF-9/BMP-15 heterodimer may also be used to modulate granulosa cell apoptosis. Thus, the various forms of present invention also include modulating the concentration of GDF-9/BMP-15 heterodimer that a granulosa cell is exposed to, and/or modulating the activity of a GDF-9/BMP-15 heterodimer dependent signalling pathway in a granulosa cell.

For example, in one form the present invention provides a method of modulating apoptosis of a granulosa cell, the method including one or more of the following steps:
  (i) modulating the concentration of GDF-9/BMP-15 heterodimer that the granulosa cell is exposed to; and
  (ii) modulating activity of a GDF-9/BMP-15 heterodimer dependent signalling pathway in the granulosa cell.

It has also been recognised that the present invention is suitable for reducing apoptosis induced by damage due to freeze-thawing.

Accordingly, in another form the present invention provides a method of reducing granulosa cell apoptosis due to freeze-thawing, the method including one or more of the following steps:
  (i) modulating the concentration and/or activity of BMP-15 and/or BMP-6 that the granulosa cell is exposed to;
  (ii) modulating activity of a BMP-15 dependent signalling pathway in the granulosa cell; and
  (iii) modulating activity of a BMP-6 dependent signalling pathway in a granulosa cell.

The modulation of the concentration of active BMP-16 and/or active BMP-6, or modulating activity of a BMP-15 or BMP-6 dependent signalling pathway, may occur before and/or after freezing.

Individual cumulus oocyte complexes, whole follicles, ovarian tissue, or whole ovaries when frozen typically die as a result of freeze/thawing. Thus, the present invention is also suitable for reducing damage to these cells/tissues due to freeze-thawing.

Accordingly, in another form the present invention provides a method of reducing damage to a cumulus oocyte complex, follicle, ovarian tissue or ovary due to freeze-thawing, the method including exposing the cumulus oocyte complex, follicle, ovarian tissue or ovary to one or more of the following:
  (i) an effective of BMP-15 and/or BMP-6;
  (ii) an effective amount of an agent that modulates activity of a BMP-15 dependent signalling pathway in a granulosa cell in the cumulus oocyte complex, follicle, ovarian tissue or ovary; and
  (iii) an effective amount of an agent that modulates activity of a modulating activity of a BMP-6 dependent signalling pathway in a granulosa cell in the cumulus oocyte complex, follicle, ovarian tissue or ovary.

The modulation of the concentration of active BMP-16 and/or active BMP-6, or modulating activity of a BMP-15 or BMP-6 dependent signalling pathway, may occur before freezing and/or after thawing.

Preferably, the agent that modulates activity of a modulating activity of a BMP-15 or BNP-6 dependent signalling pathway in the various forms of the present invention promotes the activity of these pathways, so as to reduce the level of granulosa cell apoptosis.

Modulating the activity of a BMP-15 dependent signalling pathway in the granulosa cell in the various forms of the present invention may be accomplished by a suitable method. For example, the activity of the BMPRII receptor may be modulated by exposing the granulosa cell to one or more of BMP-7, BMP-4 and BMP-2.

Modulating the activity of a BMP-6 dependent signalling pathway in the granulosa cell may also be accomplished by a suitable method.

Preferably, apoptosis is modulated by exposing the granulosa cell to a composition including an effective amount of BMP-15 and/or BMP-6, or by exposing the cell to a composition including an agent that inhibits or promotes BMP-15 and/or BMP-6 signalling pathways in the cell.

Accordingly, in a preferred form the present invention also provides a composition for modulating apoptosis of a granulosa cell, the composition including one or more of the following:
  (i) an effective amount of BMP-5 and/or BMP-6;
  (ii) an effective amount of an agent that modulates activity of a BMP-15 dependent signalling pathway in the granulosa cell; and
  (iii) an effective amount of an agent that modulates activity of a BMP-6 dependent signalling pathway in the granulosa cell.

The granulosa cell may be present in vitro or in vivo. For example, the granulosa cell may be present as part of a cumulus oocyte complex in vitro, or a granulosa cell as part of a follicle in a female subject.

In a particularly preferred form, the composition is a culture medium for reducing apoptosis of granulosa cells in a cumulus oocyte complex and/or in a follicle in vitro.

Accordingly, in another form die present invention provides a medium for culturing of a cumulus oocyte complex and/or a follicle, the medium including one or more of the following:
  (i) an effective amount of BMP-15 and/or BMP-6;
  (ii) an effective amount of an agent that increases activity of a BMP-15 dependent signalling pathway in a granulosa cell in the cumulus oocyte complex or in the follicle; and
  (iii) an effective amount of an agent that increases activity of a BMP-6 dependent signalling pathway in a granulosa cell in the cumulus oocyte complex or in the follicle.

The effective amount is an amount that reduces apoptosis in the granulosa cell(s).

It will be appreciated that BMP-15 anchor BMP-6, and/or the agent that modulates activity of a BMP-15 dependent signalling pathway, and/or the agent that modulates activity of a modulating activity of a BMP-6 dependent signalling, may also be used as a culture medium supplement for an embryos and/or oocyte.

Accordingly, in another form the present invention provides a combination product including the following components:
- an oocyte and/or embryo culture medium;
- BMP-15 and/or BMP-6, or a variant or an analogue thereof; and/or
- an agent that modulates activity of a BMP-15 dependent signalling pathway in a granulosa cell; and/or
- an agent that modulates activity of a BMP-6 dependent signalling pathway in a granulosa cell;

wherein the components are provided in a form for addition of the components to the culture medium.

The combination product may be used for any of the stated applications herein described.

The culture medium and the other various components in the various combination products of the present invention may be packaged separately in suitable containers (preferably sterilized) such as ampoules, bottles, or vials, either in multi-use or in unit forms. The containers may be hermetically sealed after being filled. The proteins components may be in isolated form, or in purified or semi-purified form, and may contain additional additives for the stability and/or use of the proteins. Methods for packaging the various components are known in the art.

The composition may also be used to modulate the maturation of an oocyte, by modulating the level of apoptosis in granulosa cells associated with the oocyte.

Accordingly, in another form the present invention provides a composition for modulating maturation of an oocyte, the composition including one or more of the following:
(i) an amount of BMP-15 and/or BMP-6 effective to modulate apoptosis of granulosa cells associated with the oocyte;
(ii) an amount of an agent effective to modulate apoptosis of granulosa cells associated with the oocyte by modulating activity of a BMP-15 dependent signalling pathway in the granulosa cells; and
(iii) an amount of an agent effective to modulate apoptosis of granulosa cells associated with the oocyte by modulating the activity of a BMP-6 dependent signalling pathway in the granulosa cells.

As discussed previously, the composition is particularly suitable for formulation of a medium for in vitro maturation of an oocyte.

Accordingly, in another form the present invention provides an oocyte in vitro maturation medium, the medium including one or more of the following:
(i) an effective amount of BMP-15 and/or BMP-6;
(ii) an effective amount of an agent that increases activity of a BMP-15 N dependent signalling pathway in a granulosa cell associated with the oocyte; and
(iii) an effective amount of an agent that increases activity of a BMP-6 dependent signalling pathway in a granulosa cell associated with the oocytes.

The effective amount is an amount that reduces apoptosis in the granulosa cell(s).

The composition may also be used to modulate the developmental competence of an oocyte, by modulating the level of apoptosis in granulosa cells associated with the oocyte.

Accordingly, in another form the present invention provides a composition for modulating developmental competence of an oocyte, the composition including one or more of the following:
(i) an amount of BMP-15 and/or BMP-6 effective to modulate apoptosis of granulosa cells associated with the oocyte;
(ii) an amount of an agent effective to modulate apoptosis of granulosa cells associated with the oocyte by modulating activity of a BMP-15 dependent signalling pathway in the granulosa cells; and
(iii) an amount of an agent effective to modulate apoptosis of granulosa cells associated with the oocyte by modulating the activity of a BMP-6 dependent signalling pathway in the granulosa cells.

The composition is particularly suitable for formulation of a medium for improving the developmental competence of an oocyte in vitro.

Accordingly, in another form the present invention provides a medium for improving the developmental competence of an oocyte, the medium including one or more of the following:
(i) an effective amount of BMP-15 and/or BMP-6;
(ii) an effective amount of an agent that increases activity of a BMP-15 dependent signalling pathway in a granulosa cell associated with the oocyte; and
(iii) an effective amount of an agent that increases activity of a BMP-6 dependent signalling pathway in a granulosa cell associated with the oocytes.

The effective amount is an amount that reduces apoptosis in the granulosa cell(s).

Alternatively, the composition may be administered to a female subject to prevent and/or treat a disease or condition associated with oocyte maturation and/or follicle maturation in a female subject. Examples of such diseases or conditions include granulosa cell tumours and polycystic ovary syndrome.

Accordingly, in another form the present invention provides a composition for preventing and/or treating in a female subject a disease or condition associated with oocyte maturation and/or follicle maturation, the composition including one or more of the following:
(i) an amount of BMP-15 and/or BMP-6 effective to modulate apoptosis of granulosa cells in the subject;
(ii) an amount of an agent effective to modulate apoptosis of granulosa cells in the subject by modulating activity of a BMP-15 dependent signalling pathway in the granulosa cells; and
(iii) an amount of an agent effective to modulate apoptosis of granulosa cells in the subject by modulating the activity of a BMP-6 dependent signalling pathway in the granulosa cells.

The composition may also be administered to a subject to prevent and/or treat damage that results to a subject by treatments such as chemotherapy.

The composition may also be used to culture follicles.

Accordingly, in another form the present invention provides a composition for culturing a follicle, the composition including one or more of the following:
(i) an amount of BMP-15 and/or BMP-6 effective to modulate apoptosis of granulosa cells in the follicle;
(ii) an amount of an agent effective to modulate apoptosis of granulosa cells in the follicle by modulating activity of a BMP-15 dependent signalling pathway in the granulosa cells; and (iii) an amount of an agent effective to modulate apoptosis of granulosa cells in the follicle by modulating the activity of a BMP-6 dependent signalling pathway in the granulosa cells.

The composition is particularly suitable for formulation of a medium for in vitro culturing of a follicle.

Accordingly, in another form the present invention provides a follicle culture medium, the medium including one or more of the following:
   (i) an effective amount of BMP-15 and/or BMP-6;
   (ii) an effective amount of an agent that increases activity of a BMP-15 dependent signalling pathway in a granulosa cell in the follicle; and
   (iii) an effective amount of an agent that increases activity of a BMP-6 dependent signalling pathway in a granulosa cell in the follicle.

The effective amount is an amount that reduces apoptosis in the granulosa cell(s).

The composition may also be used to modulate follicle atresia, by modulating the level of apoptosis in granulosa cells in a follicle.

Accordingly, in another form the present invention provides a composition for modulating atresia of a follicle, the composition including one or more of the following:
   (i) an amount of BMP-15 and/or BMP-6 effective to modulate apoptosis of granulosa cells in the follicle;
   (ii) an amount of an agent effective to modulate apoptosis of granulosa cells in the follicle by modulating activity of a BMP-15 dependent signalling pathway in the granulosa cells; and
   (iii) an amount of an agent effective to modulate apoptosis of granulosa cells in the follicle by modulating the activity of a BMP-6 dependent signalling pathway in the granulosa cells.

The composition may be used on follicles in vitro or in vivo. For a follicle in vitro, the composition may be in the form of a medium for modulating atresia.

The composition may also be used to modulate development of a follicle, by modulating the level of apoptosis in granulosa cells in the follicle.

Accordingly, in another form the present invention provides a composition for modulating development of a follicle, the composition including one or more of the following:
   (i) an amount of BMP-15 and/or BMP-6 effective to modulate apoptosis of granulosa cells in the follicle;
   (ii) an amount of an agent effective to modulate apoptosis of granulosa cells in the follicle by modulating activity of a BMP-15 dependent signalling pathway in the granulosa cells; and
   (iii) an amount of an agent effective to modulate apoptosis of granulosa cells in the follicle by modulating activity of a BMP-6 dependent signalling pathway in the granulosa cells.

The composition may be used on follicles in vitro or in vivo. For a follicle in vitro, the composition may be in the form of a medium for modulating development of the follicle.

The composition may also be used to modulate the ovulation rate in a female subject by modulating the level of apoptosis in granulosa cells in the female subject.

Accordingly, in another form the present invention provides a composition for modulating ovulation rate in a female subject, the composition including one or mole of the following:
   (i) an amount of BMP-15 and/or BMP-6 effective to modulate apoptosis of granulosa cells in the subject;
   (ii) an amount of an agent effective to modulate apoptosis of granulosa cells in the subject by modulating activity of a BMP-15 dependent signalling pathway in the granulosa cells; and
   (iii) an amount of an agent effective to modulate apoptosis of granulosa cells in the subject by modulating activity of a BMP-6 dependent signalling pathway in the granulosa cells.

The composition may also be used to modulate the number of follicles that mature each ovarian or menstrual cycle in a female subject by modulating the level of apoptosis in granulosa cells in the subject.

Accordingly, in another form the present invention also provides a composition for modulating the number of follicles that mature each ovarian or menstrual cycle in a female subject, the composition including one or more of the following:
   (i) an amount of BMP-15 and/or BMP-6 effective to modulate apoptosis of granulosa cells in the subject;
   (ii) an amount of an agent effective to modulate apoptosis of granulosa cells in the subject by modulating activity of a BMP-15 dependent signalling, pathway in the granulosa cells cells; and
   (iii) an amount of an agent effective to modulate apoptosis of granulosa cells in the subject by modulating activity of a BMP-6 dependent signalling pathway in the granulosa cells.

The composition may also be used to modulate fertility in a female subject by modulating the level of apoptosis of granulosa cells in the female subject.

Accordingly, in another form the present invention provides a composition for modulating fertility in a female subject, the composition including one or more of the following:
   (i) an amount of BMP-15 and/or BMP-6 effective to modulate apoptosis of granulosa cells in the subject;
   (ii) an amount of an agent effective to modulate apoptosis of granulosa cells in the subject by modulating activity of a BMP-15 dependent signalling pathway in the granulosa cells; and
   (iii) an amount of an agent effective to modulate apoptosis of granulosa cells in the subject by modulating activity of a BMP-6 dependent signalling pathway in the granulosa cells.

The compositions of the present invention may be used to promote fertility, or alternatively, may be used as a contraceptive.

For example, in the case where the agent decreases apoptosis, the composition may be used to increase fertility in a female subject when administered.

Accordingly, in another form the present invention provides a composition for promoting fertility in a female subject, the composition including an amount of an agent effective to decrease apoptosis of granulosa cells in a female subject by increasing activity of a BMP-15 dependent signalling pathway in granulosa cells in the subject, and/or an amount of an agent effective to decrease apoptosis of granulosa cells in a female subject by increasing activity of a BMP-6 dependent signalling pathway in the granulosa cells.

For example, the agent may be BMP-15 or BMP-6.

In the case where the agent promotes apoptosis, the composition may be used as a contraceptive composition when administered to a female subject.

Accordingly, in another form the present invention provides a contraceptive composition, the composition including an amount of an agent effective to increase apoptosis of granulosa cells in a female subject by decreasing activity of a BMP-15 dependent signalling pathway in granulosa cells in the subject, and/or an amount of an agent effective to increase apoptosis of granulosa cells in a female subject by decreasing activity of a BMP-6 dependent signalling pathway in the granulosa cells.

For example, the agent may be a suitable antagonist antibody directed a BMP-15 or BMP-6, or a soluble form of the BMPRII receptor.

In the case where the agent in the various forms of the present invention inhibits the activity of the BMPR-II and/or AlK6 receptors, the agent may interfere with the activity of the receptors by reducing the concentration of one or more oocyte-secreted factors that bind to the receptor, the agent may interfere with the activity of the receptor by binding to the receptor and thereby act as an antagonist, the agent may interfere with the activity of the receptor by causing a conformational change in the structure of the receptor, the agent may interfere with the formation of a heterodimer between the BMPR-II receptor and the AlK6 receptor, the agent may interfere with the phosphorylation of one or more intracellular proteins involved in signal transduction from the receptors, or the agent may modulate the concentration of one or more factors in the cell (including the expression of the receptors), so as to interfere with the signalling activity of the receptor.

In the case where the agent inhibits the activity of the receptors, preferably the agent inhibits the activity by reducing the concentration of one or more oocyte secreted factors that bind to the receptors or by reducing the phosphorylation of Smad1 and/, or Smad 5 and/or Smad8 in the granulosa cell.

In the case where the agent promotes the activity of the receptors, the agent may activate promote the binding of one or more oocyte-secreted factors that bind to the receptors, the agent may act as a receptor agonist, the agent may promote the activity of the receptors by causing a conformational change in the structure of the receptor, the agent may promote the formation of a heterodimer between the BMPR-II receptor and the AlK6 receptor, the agent may promote the phosphorylation of one or more intracellular proteins involved in signal transduction from the receptor, or the agent may modulate the concentration of one or more factors in the cell (including the expression of the receptors), so as to promote the signalling activity of the receptor.

Examples of the types of agents that may modulate the activity of the BMPR-II and/or AlK6 receptors include proteins, antibodies, aptamers, antisense nucleic acids, antisense oligonucleotides, siRNAs, polypeptides, peptides, small molecules, drugs, polysaccharides, glycoproteins, and lipids.

For example, in the case where the agent inhibits the activity of BMPR-II, the agent in the various forms of the present invention may be (i) a soluble form of the BMPR-II receptor that is capable of competitively binding one or more oocyte-secreted factors that bind to the membrane bound receptor and thereby reduce the concentration of one or more of the oocyte-secreted factors available for binding to the receptor; (ii) an antisense oligonucleotide that may reduce the concentration of BMPR-II expressed on the surface of a granulosa cell; (iii) an agent that interferes with the phosphorylation of Smad 1 and/or Smad5 and/or Smad8 by the BMPR-II/type-I heterodimer in a granulosa cell; or (v) an antibody raised against and targeting the extracellular domain of BMPR-II, that is capable of competitively binding the receptor and thereby reducing the binding of one or more oocyte-secreted growth factors.

In the case where the agent inhibits the activity of either or both of the BMPR-II and AlK6 receptors, preferably the agent inhibits the activity by inhibiting BMP-15 dependent stimulation (including stimulation by GDF-9/BNP-15 heterodimer), or inhibiting BMP-6 dependent stimulation.

Determination that an agent modulates BMP-15 and/or BMP-6 signalling in a granulosa cell may be by a suitable method known in the art.

Preferably the agent modulates the activity of a BMP-15 and/or BMP-6 dependent signalling pathway by modulating phosphorylation of Smad1 and/or Smad5 and/or Smad8 in the granulosa cell.

Determination of the ability of an agent to modulate the phosphorylation of Smad 1 and/or Smad 5 and/or Smad 8 may be by a suitable method known in the all.

In the case of an agent that inhibits the activity of BMPR-II or AlK6 being an antisense nucleic acid to BMPR-II, the agent may be a nucleic acid complementary to all or part of the nucleotide sequence of the either of the receptors.

The antisense nucleic acid may be composed of DNA or RNA, or any modification or derivative thereof. The antisense nucleic acid may be an oligonucleotide or a polynucleotide. In a preferred form of the invention, the agent is a DNA antisense oligonucleotide.

In the case of an antisense nucleic acid that is an antisense oligonucleotide, the oligonucleotide may be modified at the base moiety, sugar moiety, or phosphate backbone, and may include other appending groups to facilitate the function of the antisense nucleic acid.

The oligonucleotide may be modified at any position on its structure with constituents generally known in the art. For example, the antisense oligonucleotide may comprise at least one modified base moiety which is selected from the group including 5-fluorouracil, 5-bromouracil, 5-chlorouracil, 5-iodouracil, hypoxantihine, xanthine, 4-acetylcytosine, 5-(carboxyliydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguaninie, 2-methyladenine, 2-methylguailine, 3-methylcytosine, 5-methylcytosine, N6-adenine, 7-methylguanine, 5-methylaminomethyluracil, 5-methoxyaminomethyl-2-thiouracil, beta D-manniosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The oligonucleotide may also include at least one modified sugar moiety selected from the group including, but not limited to, arabinose, 2-fluoroarabinose, xylulose, and hexose. In addition, the oligonucleotide may include at least one modified phosphate backbone, such as a phosphorothioate, a phosphorodithioate, a phosphoramidothioate, a phosphoramidate, a phosphordiamidate, a methylphosphonate, an alkyl phosphotriester, and a formacetal or any analogue thereof.

Antisense oligonucleotides according to the various forms of the present invention may be synthesized by standard methods known in the alt. For example, phosphorothioate oligonucleotides may be synthesized by the method as described in Stein et al. (1988) *Nucl. Acids Res.* 16: 3209.

Alternatively, the antisense nucleic acid according to the various forms of the present invention may be produced intracellularly by transcription from an exogenous sequence. For example, a vector can be introduced into a granulosa cell and an antisense RNA nucleic acid may then be produced by transcription. As will be appreciated, the vector in this case will contain a sequence encoding the antisense nucleic acid and a suitable constitutive or inducible promoter for driving expression of the antisense nucleic acid in the granulosa cell known in the art.

Such a vector can remain episomal or become chromosomally integrated, as long as it can be transcribed to produce the desired antisense RNA. Vectors can be constructed by recombinant DNA technology methods standard in the an, for example as generally described in Sambrook, J, Fritsch, E. F. and Maniatis, T. Molecular Cloning: A laboratory Manual 2nd. ed. Cold Spring Harbor laboratory Press, New York. (1989). Vectors can be plasmid, viral, or other vectors known in the art, used for the replication and expression in eukaryotic cells.

In the case of the agent in the various forms of the present invention being an antibody, the antibody may be generated using methods that are known in the art. Such antibodies include, polyclonal, monoclonal, chimeric, single chain, Fab fragments, and fragments produced by a Fab expression library.

For the production of antibodies, various hosts including goats, rabbits, rats, mice, humans, and others, may be immunized by injection with the polypeptide or any fragment or oligopeptide thereof that has immunogenic properties. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol.

Monoclonal antibodies may be prepared using any technique which provides for the production of antibody molecules by continuous cell lines in culture. These include, but are not limited to, the hybridoma technique, the human B-cell hybridoma technique, and the EBV-hybridoma technique, for example as described in Kohler, G. et al. (1975) *Nature* 256: 495-497; Kozbor, D. et al. (1985) *J. Immunol. Methods* 81:31-42; Cote, R. J. et al. (1983) *Proc. Natl. Acad. Sci.* 80:2026-2030; or Cole, S. P. et al. (1984) *Mol. Cell Biol.* 62:109-120.

For example, to generate a monoclonal antibody to a protein that modulates bone morpliogenic receptor type II, a peptide sequence of the protein may be synthesized and coupled to a purified protein derivative of tuberculin as described in Groome and lawrence M (1991) Hybridoma 10:309-316. Outbred Tyler's Original (T/O) mice (Southend on Sea, Essex, UK) may then undergo an immunization regime over a 4 month period. The animals are then sacrificed and the spleens removed for fusion to Sp2/0 murine myeloma cells, as described in Coding (1986) Monoclonal Antibodies: Principle and Practice. New York: Academic Press.

Hybridoma supernatants may be initially screened by EllSA, against the peptide coated to Nune immunoplates as described in Groome N. P. et al (1990) Hybridoma 9:31-42. Reactive clones may then be expanded and recloned by limiting dilution. These may then be rescreened against the target protein and the best reacting clones selected, prior to expansion and isotyping. IgG antibodies may be on a protein A column using a high salt protocol before assessment, as described in Harlow, E. and lane D. (1988) Antibodies: A laboratory Manual. Cold Spring Habor Press., Plainview, N.Y.

In addition, techniques developed for the production of "chimeric antibodies", the splicing of mouse antibody genes to human antibody genes to obtain a molecule with appropriate antigen specificity and biological activity can be used, for example as described in Morrison, S. l. et al. (1984) *Proc. Nalt. Acad. Sci.* 81:6851-6855; Neuberger, M. S. et al. (1984) *Nature* 312:604-608; or Takeda, S. et al. (1985) *Nature* 314: 452-454.

Antibody fragments which contain specific binding sites may also be generated. For example, such fragments include F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity, for example as described in Huse, V. D. et al. (1989) *Science* 254:1275-1281.

Various immunoassays may be used for screening to identify antibodies having the desired specificity. Numerous protocols for competitive binding or immunoradiometric assays using either polyclonal or monoclonal antibodies with established specificities are known in the art.

The effective amount of the agent to be exposed to the granulosa cell is not particularly limited, so long as it is within such an amount and in such a form that it exhibits the effect of modulating the apoptosis of a granulosa cell.

In this regard, an effective amount of the agent may be appropriately chosen, depending upon the extent of granulosa cell apoptosis to be modulated, and if the agent is to be administered in vivo, the age and body weight of the subject, the frequency of administration, and the presence of other active agents may need to be taken into consideration.

In the case of the agent being administered to a granulosa cell in vitro, the administration may occur by direct exposure of the granulosa cell to the agent.

As discussed previously, in this case the present invention is particularly suitable for the formulation of an oocyte in vitro maturation medium.

Accordingly, the present invention provides an oocyte in vitro maturation medium, the medium including one or more of the following:

(i) BMP-15 and/or BMP-6;
(ii) an agent that inhibits apoptosis of a granulosa cell associated with the oocyte by modulating activity of a BMP-15 dependent signalling pathway in the granulosa cell; and
(iii) an agent that inhibits apoptosis of a granulosa cell associated with the oocyte by modulating the activity of a BMP-6 dependent signalling pathway in the granulosa cell;

Preferably, the concentration of BMP-15 effective to inhibit apoptosis in granulosa cells is 1 to 1500 ng/ml.

Preferably, the concentration of BMP-6 effective to inhibit apoptosis in granulosa cells is 1 to 200 ng/ml.

In this regard, it has been further determined that the addition of an agent that inhibits apoptosis of granulosa cells by modulating the activity of a BMP-15 and/or BMP-6 dependent signalling pathway may be used to allow the formulation of compositions or media that do not contain additives that are normally present to reduce apoptosis of granulosa cells. Such additives include serum, albumin, follicular fluid, fetuin, follicle stimulating hormone (FSH), and anti-apoptotic growth factors such as IGFs (eg IGF-1) and EGFs (including amphiregulin and epiregulin).

Thus, in its various relevant forms the present invention provides compositions and media substantially free of the above additives and including an agent that inhibits apoptosis of granulosa cells by modulating the activity of a BMP-15 and/or BMP-6 dependent signalling pathway.

For example, the medium may be a culture medium for a cumulus oocyte complex and/or a follicle.

Accordingly, in another form the present invention provides a medium for culturing of a cumulus oocyte complex and/or a follicle, the medium including one or more of the following:

(i) an effective amount of BMP-15 and/or BMP-6;
(ii) an effective amount of an agent that increases activity of a BMP-15 dependent signalling pathway in a granulosa cell in the cumulus oocyte complex or in the follicle; and
(iii) an effective amount of an agent that increases activity of a BMP-6 dependent signalling pathway in a granulosa cell in the cumulus oocyte complex or in the follicle;

wherein the medium is substantially free of serum, albumin, follicular fluid, fetuin, follicle stimulating hormone (FSH), and anti-apoptotic growth factors.

For example, the medium may be used for the in vitro maturation of an oocyte in a cumulus oocyte complex.

Accordingly, in another form the present invention provides an oocyte in vitro maturation medium, the medium including one or more of the following components:

(i) BMP-15 and/or BMP-6;
(ii) an agent that inhibits apoptosis of one or more granulosa cells associated with the oocyte by modulating activity of a BMP-15 dependent signalling pathway in the one or more granulosa cells; and
(iii) an agent that inhibits apoptosis of the one or more granulosa cells associated with the oocyte by modulating the activity of a BMP-6 dependent signalling pathway in the one or more granulosa cells;

wherein the medium is substantially free of serum, albumin, follicular fluid, fetuin, follicle stimulating hormone (FSH), and anti-apoptotic growth factors.

The present invention is also suitable for the formulation of a medium for culturing a follicle, and in particular, to improve follicle development or reduce follicle atresia.

Accordingly, in another form the present invention provides a follicle culture medium, the medium including one or more of the following components:

(i) BMP-15 and/or BMP-6;
(ii) an agent that inhibits apoptosis of one or more granulosa cells in the follicle by modulating activity of a BMP-15 dependent signalling pathway in the one or more granulosa cells; and
(iii) an agent that inhibits apoptosis of the one or more granulosa cells in the follicle by modulating the activity of a BMP-6 dependent signalling pathway in the one or more granulosa cells;

wherein the composition is substantially free of serum, albumin, follicular fluid, fetuin, follicle stimulating hormone (FSH), and anti-apoptotic growth factors.

The present invention in its various forms also provides a composition or medium including an agent that inhibits apoptosis of a granulosa cell and other additive for the formulation of medium for the culturing of oocytes and/or follicles.

Preferably, the composition or medium includes NaCl. More preferably, the composition or medium includes 40 mM to 400 mM NaCl.

Preferably, the composition or medium includes KCl. More preferably, the composition or medium includes 0.1 mM to 20 mM KCl.

Preferably, the composition or medium includes glucose. More preferably, the composition or medium includes 0.1 mM to 40 mM glucose.

Accordingly, in another form the present invention provides a composition or medium including one or more of the following:

(i) BMP-15 and/or BMP-6;
(ii) an agent that inhibits apoptosis of a granulosa cell by modulating activity of a BMP-15 dependent signalling pathway in the granulosa cell; and
(iii) an agent that inhibits apoptosis of a granulosa cell by modulating the activity of a BMP-6 dependent signalling pathway in the granulosa cell;

the composition further including 40 mM to 400 mM NaCl, 0.1 mM to 20 mM KCl, and 0.1 mM to 40 mM glucose.

The composition or medium may be used for the in vitro maturation of oocytes, or for the culturing of follicles Methods for the use of such compositions or media for these purposes are known on the art.

Preferably, the concentration of BMP-15 effective to inhibit apoptosis in granulosa cells is 1 to 1500 ng/ml.

Preferably, the concentration of BMP-6 effective to inhibit apoptosis in granulosa cells is 1 to 200 ng/ml.

Preferably, the concentration of NaCl in the composition is 100 mM to 180 mM. Most preferably, the concentration of NaCl is 140 mM.

Preferably, the concentration of KCl in the composition is 1 mM to 8 mM. Most preferably, the concentration of KCl is 4 mM.

Preferably, the concentration of glucose in the composition is 1 mM to 25 mM. Most preferably, the concentration of glucose is 5.6 mM.

The composition will generally also include a suitable inorganic buffer, such as a zwitterionin or phosphate buffer, or a sodium bicarbonate buffer with a concentration in the range from 10 mM to 60 mM. Preferably, the concentration of sodium bicarbonate is 20 mM to 40 mM. Most preferably, the concentration of sodium bicarbonate is 25 mM.

For example, a suitable medium (g/l) using BMP-15 is as follows:

| | |
|---|---|
| BMP-15 | 0.0005 |
| CaCl$_2$•2H$_2$0 | 0.265 |
| MgSO$_4$•6H$_2$0 | 0.09767 |
| KCl | 0.4 |
| NaCl | 6.8 |
| NaH$_2$PO4 | 0.122 |
| L-Arginine•HCl | 0.126 |
| L-Cysteine•HCL•monohydrate | 0.0313 |
| L-Glutamine | 0.292 |
| L-Histidine•HCL•monohydrate | 0.042 |
| L-Isoleucine | 0.052 |
| L-Leucine | 0.052 |
| L-Lysine•HCl | 0.0725 |
| L-Methionine | 0.015 |
| L-Phenylalanine | 0.032 |
| L-Threonine | 0.048 |
| L-Tryptophan | 0.01 |
| L-Tyrosine•2Na•dihydrate | 0.0519 |
| L-Valine | 0.046 |
| Choline chloride | 0.001 |
| Folic acid | 0.001 |
| myo-inositol | 0.002 |
| Niacinamide | 0.001 |
| D-Pantothenic acid•1/2Ca | 0.001 |
| Pyridoxal•HCl | 0.001 |
| Riboflavin | 0.0001 |
| Thiamine•HCl | 0.001 |
| Glucose | 1 |
| Phenol red.Na | 0.011 |
| NaHCO$_3$ | 2.2 |

A suitable medium (g/l) using BMP-6 is as follows:

| | |
|---|---|
| BMP-6 | 0.0001 |
| CaCl$_2$•2H$_2$0 | 0.265 |
| MgSO$_4$•6H$_2$0 | 0.09767 |
| KCl | 0.4 |
| NaCl | 6.8 |
| NaH$_2$PO4 | 0.122 |
| L-Arginine•HCl | 0.126 |
| L-Cysteine•HCL•monohydrate | 0.0313 |
| L-Glutamine | 0.292 |
| L-Histidine•HCL•monohydrate | 0.042 |
| L-Isoleucine | 0.052 |
| L-Leucine | 0.052 |
| L-Lysine•HCl | 0.0725 |
| L-Methionine | 0.015 |
| L-Phenylalanine | 0.032 |
| L-Threonine | 0.048 |
| L-Tryptophan | 0.01 |
| L-Tyrosine•2Na•dihydrate | 0.0519 |
| L-Valine | 0.046 |
| Choline chloride | 0.001 |
| Folic acid | 0.001 |
| myo-inositol | 0.002 |
| Niacinamide | 0.001 |
| D-Pantothenic acid•1/2Ca | 0.001 |
| Pyridoxal•HCl | 0.001 |
| Riboflavin | 0.0001 |
| Thiamine•HCl | 0.001 |
| Glucose | 1 |
| Phenol red•Na | 0.011 |
| NaHCO$_3$ | 2.2 |

As discussed previously, it has also been recognised that the present invention is also suitable for reducing apoptosis induced by freeze-thawing damage.

Accordingly, in another form the present invention provides a composition for reducing granulosa cell apoptosis due to freeze-thawing, the composition including one or more of the following:
 (i) active BMP-15 and/or active BMP-6;
 (ii) an agent that increases activity of a BMP-15 dependent signalling pathway in the granulosa cell; and
 (iii) an agent that increases activity of a BMP-6 dependent signalling pathway in a granulosa cell.

The composition may be used before freezing and/or after thawing.

For example, individual cumulus oocyte complexes, whole follicles, ovarian tissue, or whole ovaries when frozen typically die as a result of freeze/thawing, and the composition may be used to improve the viability of cells and tissue following freeze-thawing.

Accordingly, in another form the present invention provides a composition for reducing damage to a cumulus oocyte complex, follicle, ovarian tissue or ovary due to freezing, the composition including one or more of the following:
 (i) an effective amount of active BMP-15 and/or active BMP-6;
 (ii) an effective amount of an agent that increases activity of a BMP-15 dependent signalling pathway in a granulosa cell in the cumulus oocyte complex, follicle, ovarian tissue or ovary; and
 (iii) an effective amount of an agent that increases activity of a BMP-6 dependent signalling pathway in a granulosa cell in the cumulus oocyte complex, follicle, ovarian tissue or ovary.

In a preferred from, the composition is a culture medium.

The composition and/or medium of the present invention is particularly suitable for culturing oocytes that are used for assisted reproduction technologies. Methods for performing assisted reproduction are known in the art.

In this regard, the term "assisted reproduction" as used throughout the specification is to be understood to mean any fertilization technique in humans and animals involving isolated oocytes and/or isolated sperm, including a technique using an oocyte or embryo cultured in vitro (for example in vitro maturation of an oocyte), in vitro fertilization (IVF; aspiration of an oocyte, fertilization in the laboratory and transfer of the embryo into a recipient), gamete intrafallopian transfer (GIFT; placement of oocytes and sperm into the fallopian tube), zygote intrafallopian transfer (ZIFT; placement of fertilized oocytes into the fallopian tube), tubal embryo transfer (TET; the placement of cleaving embryos into the fallopian tube), peritoneal oocyte and sperm transfer (POST; the placement of oocytes and sperm into the pelvic cavity), intracytoplasmic sperm injection (ICSI), testicular sperm extraction (TESE), and microsurgical epididymal sperm aspiration (MESA).

Accordingly, in another form the present invention provides a method of assisted reproduction involving an oocyte, the method including the step of culturing the oocyte in a medium including one or more of the following components:
 (i) BMP-15 and/or BMP-6;
 (ii) an agent that inhibits apoptosis of one or more granulosa cells associated with the oocyte by modulating activity of a BMP-15 dependent signalling pathway in the one or more granulosa cells; and
 (iii) an agent that inhibits apoptosis of one or more granulosa cells associated with the oocyte by modulating the activity of a BMP-6 dependent signalling pathway in the one or more granulosa cells.

For example, the present invention may be used in an in vitro fertilization technique.

Accordingly, in another form the present invention provides a method of in vitro fertilization of an oocyte, the method including the step of culturing the oocyte in a medium including one or more of the following components:
 (i) BMP-15 and/or BMP-6;
 (ii) an agent that inhibits apoptosis of one or more granulosa cells associated with the oocyte by modulating activity of a BMP-15 dependent signalling pathway in the one or more granulosa cells; and
 (iii) an agent that inhibits apoptosis of one or more granulosa cells associated with the oocyte by modulating the activity of a BMP-6 dependent signalling pathway in the one or more granulosa cells.

The present invention also provides a composition for use in assisted reproduction involving an oocyte.

The present invention is suitable for modulating the developmental competence of all embryo, by modulating apoptosis of granulosa cells associated with an oocyte that is fertilized to form an embryo.

Accordingly, in another form the present invention provides a composition for modulating developmental competence of an embryo produced from an oocyte, the composition including one or more of the following:
 (i) an amount of BMP-15 and/or BMP-6 effective to modulate apoptosis of granulosa cells associated with the oocyte;
 (ii) an amount of an agent effective to modulate apoptosis of granulosa cells associated with the oocyte by modulating activity of a BMP-15 dependent signalling pathway in the granulosa cells; and
 (iii) an amount of an agent effective to modulate apoptosis of granulosa cells associated with the oocyte by modulating the activity of a BMP-6 dependent signalling pathway in the granulosa cells.

In another form, the present invention provides a method of modulating developmental competence of an embryo produced from an oocyte, the method including one or more of the following steps:
(i) modulating apoptosis of granulosa cells associated with the oocyte by modulating the concentration and/or activity of BMP-15 and/or BMP-6 that the granulosa cells are exposed to;
(ii) modulating apoptosis of granulosa cells associated with the oocyte by modulating activity of a BMP-15 dependent signalling pathway in the granulosa cells; and
(iii) modulating apoptosis of granulosa cells associated with the oocyte by modulating activity of a BMP-6 dependent signalling pathway in the granulosa cells.

In another form, the present invention also provides a method of assisted reproduction involving an embryo produced from an oocyte, the method including the step of culturing the oocyte and/or the embryo in a medium including one or more of the following components:
(i) BMP-15 and/or BMP-6;
(ii) an agent that inhibits apoptosis of one or more granulosa cells associated with the oocyte by modulating activity of a BMP-15 dependent signalling pathway in the one or more granulosa cells; and
(iii) an agent that inhibits apoptosis of one or more granulosa cells associated with the oocyte by modulating the activity of a BMP-6 dependent signalling pathway in the one or more granulosa cells.

The present invention also provides a composition for use in assisted reproduction involving an embryo produced from an oocyte.

In the case of the various agents of the present invention being administered in vivo, the agent may be delivered in a form and at a concentration suitable to allow the agent to reach the desired site of action and have the effect of inhibiting granulosa cell apoptosis.

The administration of the agent may be within any time suitable to produce the desired effect of modulating the apoptosis of granulosa cells. In this regard, the administration of die agent to the granulosa cell in the various relevant forms of the present invention may occur at any time prior to, during and after fertilization of an oocyte in vitro or in vivo associated with the granulosa cell.

In a human or animal subject, the agent may be administered orally, parenterally, topically or by any other suitable means, and therefore transit time of the agent must be taken into account.

The in vitro administration of the agent in the various forms of the present invention may also include the use of one or more pharmaceutically acceptable additives, including pharmaceutically acceptable salts, amino acids, polypeptides, polymers, solvents, buffers, excipients and bulking agents, taking into consideration the particular physical and chemical characteristics of the agent to be administered.

For example, the agent can be prepared into a variety of pharmaceutical preparations in the form of, e.g., an aqueous solution, an oily preparation, a fatty emulsion, an emulsion, a gel, etc., and these preparations can be administered as intramuscular or subcutaneous injection or as injection to the ovary, or as an embedded preparation or as a transmucosal preparation through nasal cavity, rectum, uterus, vagina, lung, etc. The preparation may be administered in the form of oral preparations (for example solid preparations such as tablets, capsules, granules or powders; liquid preparations such as syrup, emulsions or suspensions). Compositions containing the agent may also contain a preservative, stabiliser, dispersing agent, pH controller or isotonic agent. Examples of suitable preservatives are glycerin, propylene glycol, phenol or benzyl alcohol. Examples of suitable stabilisers are dextran, gelatin, α-tocopherol acetate or alpha-thioglycerin. Examples of suitable dispersing agents include polyoxyethylene (20), sorbitan mono-oleate (Tween 80), sorbitan sesquioleate (Span 30), polyoxyethylene (160) polyoxypropylene (30) glycol (Pluronic F68) or polyoxyethylene hydrogenated castor oil 60. Examples of suitable pH controllers include hydrochloric acid, sodium hydroxide and the like. Examples of suitable isotonic agents are glucose, D-sorbitol or D-mannitol.

The in vivo administration of the agent in the various forms of the present invention may also be in the form of a composition containing a pharmaceutically acceptable carrier, diluent, excipient, suspending agent, lubricating agent, adjuvant, vehicle, delivery system, emulsifier, disintegrant, absorbent, preservative, surfactant, colorant, flavorant or sweetener, taking into account the physical and chemical properties of the particular agent to be administered.

For these purposes, the composition may be administered orally, parenterally, by inhalation spray, adsorption, absorption, topically, rectally, nasally, bucally, vaginally, intraventricularly, via an implanted reservoir in dosage formulations containing conventional non-toxic pharmaceutically-acceptable carriers, or by any other convenient dosage form. The term parenteral as used herein includes subcutaneous, intravenous, intramuscular, intraperitoneal, intrathecal, intraventricular, intrasternal, and intracranial injection or infusion techniques.

When administered parenterally, the composition will normally be in a unit dosage, sterile injectable form (solution, suspension or emulsion) which is preferably isotonic with the blood of the recipient with a pharmaceutically acceptable carrier. Examples of such sterile injectable forms are sterile injectable aqueous or oleaginous suspensions. These suspensions may be formulated according to techniques known in the art using suitable dispersing or wetting agents and suspending agents. The sterile injectable forms may also be sterile injectable solutions or suspensions in non-toxic parenterally-acceptable diluents or solvents, for example, as solutions in 1,3-butanediol. Among the acceptable vehicles and solvents that may be employed are water, saline. Ringer's solution, dextrose solution, isotonic sodium chloride solution, and Hanks' solution. In addition, sterile, fixed oils are conventionally employed as solvents or suspending mediums. For this purpose, any bland fixed oil may be employed including synthetic mono- or di-glycerides, corn, cottonseed, peanut, and sesame oil. Fatty acids such as ethyl oleate, isopropyl myristate, and oleic acid and its glyceride derivatives, including olive oil and castor oil, especially in their polyoxyethylated versions, are useful in the preparation of injectables. These oil solutions or suspensions may also contain long-chain alcohol diluents or dispersants.

The cancer may contain minor amounts of additives, such as substances that enhance solubility, isotonicity, and chemical stability, for example anti-oxidants, buffers and preservatives.

When administered orally, the composition will usually be formulated into unit dosage forms such as tablets, cachets, powder, granules, beads, chewable lozenges, capsules, liquids, aqueous suspensions or solutions, or similar dosage forms, using conventional equipment and techniques known in the art. Such formulations typically include a solid, semi-solid, or liquid carrier. Exemplary carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propyl hydroxybenzoate, talc, magnesium stearate, and the like.

A tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Moulded tablets may be made by molding in a suitable machine, a mixture of the powdered active ingredient and a suitable carrier moistened with an inert liquid diluent.

The administration of the agent in the various forms of the present invention may also utilize controlled release technology. The agent may also be administered as a sustained-release pharmaceutical. To further increase the sustained release effect, the composition may be formulated with additional components such as vegetable oil (for example soybean oil, sesame oil, camellia oil, castor oil, peanut oil, rape seed oil); middle fatty acid triglycerides; fatty acid esters such as ethyl oleate; polysiloxane derivatives; alternatively, water-soluble high molecular weight compounds such as hyaluronic acid or salts thereof (weight average molecular weight: ca. 80,000 to 2,000,000), carboxymethylcellulose sodium (weight average molecular weight: ca. 20,000 to 400,000), hydroxypropylcellulose (viscosity in 2% aqueous solution: 3 to 4.000 cps), atherocollagen (weight average molecular weight: ca. 300,000), polyethylene glycol (weight average molecular weight: ca. 400 to 20,000), polyethylene oxide (weight average molecular weight: ca. 100,000 to 9,000,000), hydroxypropylmethylcellulose (viscosity in 1% aqueous solution: 4 to 100,000 cSt), methylcellulose (viscosity in 2% aqueous solution: 15 to 8,000 cSt), polyvinyl alcohol (viscosity: 2 to 100 cSt), polyvinylpyrrolidone (weight average molecular weight: 25,000 to 1,200,000).

Alternatively, the agent may be incorporated into a hydrophobic polymer matrix for controlled release over a period of days. The composition of the invention may then be molded into a solid implant, or externally applied patch, suitable for providing efficacious concentrations of the agent over a prolonged period of time without the need for frequent re-dosing. Such controlled release films are well known to the art. Other examples of polymers commonly employed for this purpose that may be used include nondegradable ethylene-vinyl acetate copolymer a degradable lactic acid-glycolic acid copolymers which may be used externally or internally. Certain hydrogels such is poly(hydroxyelhylmethacrylate) or poly(vinylalcohol) also may be useful, but for shorter release cycles than the other polymer release systems, such as those mentioned above.

The carrier may also be a solid biodegradable polymer or mixture of biodegradable polymers with appropriate time release characteristics and release kinetics. The composition may then be molded into a solid implant suitable for providing efficacious concentrations of the agent over a prolonged period of time without the need for frequent re-dosing. The agent can be incorporated into the biodegradable polymer or polymer mixture in any suitable manner known to one of ordinary skill in the art and may form a homogeneous matrix with the biodegradable polymer, or may be encapsulated in some way within the polymer, or may be molded into a solid implant.

The present invention also provides a method of assessing the developmental competence of an oocyte, by determination of the extent of apoptosis of granulosa cells cells associated with the oocyte.

Accordingly, in another form the present invention provides a method of assessing the developmental competence of an oocyte, the method including the steps of:
  (i) determining the extent of apoptosis in granulosa cells associated with the oocyte; and
  (ii) assessing the developmental competence of the oocyte by the extent of apoptosis found in the granulosa cells associated with the oocyte;
wherein a decreased level of apoptosis is indicative of an oocyte with increased developmental competence, and an increased level of apoptosis is indicative of an oocyte with reduced developmental competence.

In this regard, the term "developmentally competence" is to be understood to mean the capacity of the oocyte to develop into an embryo capable of implanting.

It will be appreciated that improved developmental competence will be associated with lower levels of apoptosis in the granulosa cells, while decreased developmental competence will be associated with increased levels of apoptosis in the granulosa cells.

The assessment of the developmental competence may be performed on an oocyte in vitro, or an oocyte in vivo.

Methods for assessing the extent of apoptosis in cells in vitro and in vivo are as previously discussed.

Thus the present invention contemplates for example assessing the developmental competence of an in vitro oocyte as part of a cumulus oocyte complex or as pan of a follicle, or the assessment of developmental competence of an oocyte in vivo.

The present invention is also suitable assessing the developmental competence of an oocyte, by determination of one or more of:
  (i) the concentration and/or activity of BMP-15 and/or BMP-6 that a granulosa cell associated with the oocyte is exposed to;
  (ii) the level of activity of a BMP-15 dependent signalling pathway in a granulosa cell associated with the oocyte; and
  (iii) the level of activity of a BMP-6 dependent signalling pathway in a granulosa cell associated with the oocyte.

In this case, improved developmental competence will be associated with a higher concentration and/or activity of BMP-15 and/or BMP-6 that a granulosa cell is exposed to, or a higher activity of a BMP-15 or BMP-6 signalling pathway in the granulosa cell, while decreased developmental competence will be associated with a lower concentration and/or activity of BMP-15 and/or BMP-6 that a granulosa cell is exposed to, or a lower activity of a BMP-15 or BMP-6 signalling pathway in the granulosa cell increased levels of apoptosis in the granulosa cells.

Accordingly, in another form the present invention provides a method of assessing the developmental competence of an oocyte, the method including the steps of:
  (i) determining one or more of: the concentration and/or activity of BMP-15 and/or BMP-6 that a granulosa cell associated with the oocyte is exposed to; determining the level of activity of a BMP-15 dependent signalling pathway in a granulosa cell associated with the oocyte; and determining the level of activity of a BMP-6 dependent signalling pathway in a granulosa cell associated with the oocyte; and
  (ii) assessing the developmental competence of the oocyte by the results of the above determinations;

wherein an increased concentration and/or activity of the BMP-15 and/or BMP-6, and/or an increased activity of the BMP-15 and/pr BMP-6 dependent signalling pathways is indicative of an oocyte with increased developmental competence, and a decreased concentration and/or activity of the BMP-15 and/or BMP-6, and/or a decreased activity of the BMP-15 and/pr BMP-6 dependent signalling pathways is indicative of an oocyte with reduced developmental competence Methods for determining the concentration or activity of BMP-15 and BMP-6, and methods for determining the activity of the appropriate signalling pathway, are known in the art.

The present invention also provides a method of assessing the developmental competence of an oocyte by determination of one or more of the expression, production and secretion of BMP-15 and BMP-6 by the oocyte.

For example, during human IVF the oocytes used are usually denuded and the developmental competence of the oocyte may be assessed by determining the BMP-15 and/or BMP-6 levels in the medium containing the oocyte prior to fertilization. A suitable method for determining the level of BMP-15 and/or BMP-6 is by ElISA.

Accordingly, in another form the present invention provides a method for assessing the developmental competence of an oocyte, the method including the steps of:
  (i) determining the level of expression of BMP-15 and/or BMP-6 in the oocyte and, or determining the concentration of BMP-15 and/or BMP-6 secreted by the oocyte; and
  (ii) assessing the developmental competence of the oocyte; wherein an increased expression and/or concentration of BMP-15 and/or BMP-6 is indicative of an oocyte with increased developmental competency, and a decreased expression and/or concentration of BMP-15 and/or BMP-6 is indicative of an oocyte with reduced developmental competence.

It has also been found in the current studies (see Study II in the Description of the Preferred Embodiments) that co-culturing of cumulus oocyte complexes during in vitro maturation with other denuded oocytes results in a dramatic improvement in the rates of blastocyst formation upon fertilization of the cumulus oocyte complex. This result demonstrates that oocyte secreted factors have a profound effect on oocyte developmental competence.

In addition, it has been further found that at least some of the oocyte secreted factors responsible for the improvement in oocyte developmental competence are GDF-9 and/or BMP-15. Thus, GDF-9 homodimers, BMP-15 homodimers and GDF-9/BMP-15 hiomodimers are likely to be involved.

It is also anticipated that BMP-6 will be one of the oocyte secreted factors that will lead to an improvement in oocyte developmental competence.

Accordingly, there is also provided a method of modulating developmental competence of an oocyte, the method including one or more of the following steps:
  (i) modulating the concentration and/or activity of oocyte secreted factors that the oocyte and/or a cumulus cell associated with the oocyte is exposed to.
  (ii) modulating the concentration and/or activity of GDF-9 and/or BMP-15 and/or BMP-6 that the oocyte and/or a cumulus cell associated with the oocyte is exposed to;
  (iii) modulating activity of a GDF-9 dependent signalling pathway in the oocyte and/or in a cumulus cell associated with the oocyte;
  (iv) modulating activity of a BMP-15 dependent signalling pathway in the oocyte and/or in a cumulus cell associated with the oocyte; and
  (v) modulating activity of a BMP-6 dependent signalling pathway in the oocyte and/or in a cumulus cell associated with the oocyte.

In this regard, it is becoming increasingly apparent that there is a need to develop new techniques for modulating and diagnosing the development and developmental competence of oocytes and embryos.

There are also well-documented difficulties associated with assisted reproduction techniques in both humans and animals. In particular there is a need to improve in vitro maturation of oocytes from females of all ages, and a need to improve the developmental competence of fertilized oocytes, especially for IVF programmes involving women over 40 years of age, as these women have approximately ¼ of the success in becoming pregnant by IVF as compared to women less than 35 years of age.

In this regard, "assisted reproduction" is to be understood to mean any fertilization technique in a human or animal involving isolated oocytes, isolated embryos and/or isolated sperm, including a technique using an oocyte or embryo cultured in vitro (for example in vitro maturation), in vitro fertilization (IVF: aspiration of an oocyte, fertilization in the laboratory and transfer of the embryo into a recipient), gamete intrafallopian transfer (GIFT; placement of oocytes and sperm into the fallopian tube), zygote intrafallopian transfer (ZIFT; placement of fertilized oocytes into the fallopian tube), tubal embryo transfer (TET; the placement of cleaving embryos into the fallopian tube), peritoneal oocyte and sperm transfer (POST; the placement of oocytes and sperm into the pelvic cavity), intracytoplasmic sperm injection (ICSI), testicular sperm extraction (TESE), and microsurgical epididymal sperm aspiration (MESA); or any other in vitro technique for producing embryos in humans and/or animals, such as nuclear transfer, parthenogenic activation and the use of totipotent cells.

The term "isolated" as used in relation to oocytes and embryos is to be understood to mean that the oocyte or embryo has at some time been removed or purified (at least partially) from its natural environment. An example of an isolated embryo is an embryo produced in vitro using an assisted reproduction technology or an embryo isolated from a subject. An example of an isolated oocyte is an oocyte isolated from a subject as part of a follicle, a cumulus oocyte complex, or a denuded oocyte.

The term "developmentally competent" is to be understood to mean an embryo or oocyte that is capable of forming an embryo that is capable of implantation.

The term "developmental competence" is to be understood to mean the ability of an oocyte or embryo to develop into an embryo capable of implantation. An oocyte or embryo with improved developmental competence will have an increased probability that it will develop into a live animal or human after successful implantation.

This method may also be used to alter the ability of an oocyte to proceed through development after fertilization.

By way of example, by increasing one or more of (i) the concentration and/or activity of oocyte secreted factors that the oocyte and/or a cumulus cell associated with the oocyte is exposed to; (ii) the concentration and/or activity of GDF-9 and/or BMP-15 and/or BMP-6 that the oocyte and/or a cumulus cell associated with the oocyte is exposed to; (iii) the activity of a GDF-9 and/or BMP-15 and/or BMP-6 dependent signalling pathway in the oocyte and/or in a cumulus cell associated with the oocyte, a fertilized oocyte in a cumulus cell complex is more likely to develop to the blastocyst or morula stage.

A suitable source of one or more oocyte secreted factors includes exposing the oocyte to one or more additional denuded oocytes. Alternatively, the oocyte may be exposed to a conditioned medium from one or more oocytes.

Preferably, modulation of the developmental competence of the oocyte is by way of modulating the concentration of GDF-9 and/or BMP-15 and/or BMP-6 that the oocyte, or a cumulus cell associated with die oocyte, is exposed to.

In this regard, the developmental competence of the oocyte may be improved by increasing the concentration of GDF-9 and/or BMP-15 and/or BMP-6 that the oocyte, or a cumulus cell associated with the oocyte, is exposed to.

Accordingly, in a preferred form there is provided a method of modulating developmental competence of an oocyte, the method including the step of modulating the concentration of GDF-9 and/or BMP-15 and/or BMP-6 that the oocyte and/or a cumulus cell associated with the oocyte is exposed to.

It will be appreciated that the modulation of the one or more steps described above may occur before fertilization of the oocyte, concurrently with fertilization of the oocyte, or post fertilization of the oocyte.

Preferably, the modulation of the one or more steps occurs before fertilization the oocyte. For example, the method may be used to improve the developmental competence of an oocyte before fertilization of the oocyte has occurred.

It will also be appreciated that the method may be used to modulate the developmental competence of an oocyte either in vitro or in vivo.

For example, the method may be used to modulate the developmental competence of an oocyte in vitro. In this regard, the oocyte may be, for example, an oocyte present in a follicle, an oocyte present in a cumulus-oocyte complex, an oocyte denuded of its cumulus cells, or a fertilized oocyte that is present in a cumulus oocyte complex or that is denuded. Preferably, the oocyte is pail of a cumulus-oocyte complex.

Methods are known in the art for collecting oocytes and cumulus-oocyte complexes from suitable recipient females and fertilizing the oocytes in vitro.

In this regard, there also provided an isolated oocyte with altered developmental competence produced by the present method (such as denuded oocyte in vitro, or an oocyte that is part of a cumulus-oocyte complex present in vitro), and an embryo or non-human animal produced from the oocyte.

The oocyte with altered developmental competence produced in vitro may be used in an assisted reproduction technique, including being transferred to a suitable recipient female subject, or may be cultured in vitro while retaining viability for use in embryo transfer, IVF and/or genetic manipulation, or may be stored or frozen prior to embryo transfer or other manipulation. In addition, embryos produced from the fertilized oocyte may be used as a source of embryonic cells for nuclear transfer or for embryonic stem cell production.

Accordingly, in another form there is also provided a method of assisted reproduction involving an oocyte, the method including one or more of the following steps:
  (i) modulating the concentration and/or activity of oocyte secreted factors that the oocyte or a cumulus cell associated with the oocyte is exposed to;
  (ii) modulating the concentration and/or activity of GDF-9 and/or BMP-15 and, or BMP-6 that the oocyte and/or a cumulus cell associated with the oocyte is exposed to;
  (iii) modulating activity of a GDF-9 dependent signalling pathway in the oocyte and/or in a cumulus cell associated with the oocyte;
  (iv) modulating activity of a BMP-15 dependent signalling pathway in the oocyte and/or in a cumulus cell associated with the oocyte; and
  (v) modulating activity of a BMP-6 dependent signalling pathway in the oocyte and/or in a cumulus cell associated with the oocyte.

For example, the method of assisted reproduction may be in vitro fertilization of an oocyte.

Accordingly, in another form there is also provided a method of in vitro fertilization of an oocyte, the method including one or more of the following steps:
  (i) modulating the concentration and/or activity of oocyte secreted factors that the oocyte or a cumulus cell associated with the oocyte is exposed to;
  (ii) modulating the concentration and/or activity of GDF-9 and/or BMP-15 and/or BMP-6 that the oocyte and/or a cumulus cell associated with the oocyte is exposed to;
  (iii) modulating activity of a GDF-9 dependent signalling pathway in the oocyte and/or in a cumulus cell associated with the oocyte;
  (iv) modulating activity of a BMP-15 dependent signalling pathway in the oocyte and/or in a cumulus cell associated with the oocyte; and
  (v) modulating activity of a BMP-6 dependent signalling pathway in the oocyte and/or in a cumulus cell associated with the oocyte.

The present invention also provides a composition for use in assisted reproduction involving an oocyte.

In another form there is also provided a method of assisted reproduction involving an embryo produced from an oocyte, the method including one or more of the following steps:
  (i) modulating the concentration and/or activity of oocyte secreted factors that the oocyte or a cumulus cell associated with the oocyte is exposed to;
  (ii) modulating the concentration and/or activity of GDF-9 and/or BMP-15 and/or BMP-6 that the oocyte and/or a cumulus cell associated with the oocyte is exposed to;
  (iii) modulating activity of a GDF-9 dependent signalling pathway in the oocyte and/or in a cumulus cell associated with the oocyte;
  (iv) modulating activity of a BMP-15 dependent signalling pathway II the oocyte and/or in a cumulus cell associated with the oocyte; and
  (v) modulating activity of a BMP-6 dependent signalling pathway in the oocyte and/or in a cumulus cell associated with the oocyte.

The present invention also provides a composition for use in assisted reproduction involving an embryo produced from an oocyte.

In a preferred form, there is also provided a composition for improving developmental competence of an oocyte, the composition including one or more of the following:
  (i) one or more additional denuded oocytes;
  (ii) one or more oocyte secreted factors;
  (iii) GDF-9 and/or BMP-15 and/or BMP-6, or variants or analogues thereof.
  (iv) an agent that increases the activity of a GDF-9 dependent signalling pathway in the oocyte and/or in a cumulus cell associated with the oocyte;
  (v) an agent that increases the activity of a BMP-15 dependent signalling pathway in the oocyte and/or in a cumulus cell associated with the oocyte; and
  (vi) an agent that increases the activity of a BMP-6 dependent signalling pathway in the oocyte and/or in a cumulus cell associated with the oocyte.

In preferred form, the composition is a culture medium for an oocyte.

Accordingly, there is also provided an oocyte culture medium, the composition including one or more of the following:
(i) one or more additional denuded oocytes;
(ii) one or more oocyte secreted factors;
(iii) GDF-9 and/or BMP-15 and/or BMP-6, or variants or analogues thereof;
(iv) an agent that increases the activity of a GDF-9 dependent signalling pathway in the oocyte and/or in a cumulus cell associated with the oocyte;
(v) an agent that increases the activity of a BMP-15 dependent signalling pathway in the oocyte and/or in a cumulus cell associated with the oocyte; and
(vi) an agent that increases the activity of a BMP-6 dependent signalling pathway in the oocyte and/or in a cumulus cell associated with the oocyte.

Preferably, the composition or medium is used to improve the developmental competence of an oocyte.

In another form, there is provided a method of assisted reproduction involving an oocyte, the method including the step of culturing the oocyte in a medium including one or more of the following:
(i) one or more denuded oocytes;
(ii) one or more oocyte secreted factors;
(iii) GDF-9 and/or BMP-15 and/or BMP-6, or variants or analogues thereof;
(iv) an agent that increases the activity of a GDF-9 dependent signalling pathway in the embryo;
(v) an agent that increases the activity of a BMP-15 dependent signalling pathway in the embryo; and
(vi) an agent that increases the activity of a BMP-6 dependent signalling pathway in the embryo.

The medium may be substantially free of one or more of serum, albumin, follicular fluid, fetuin, follicle stimulating hormone (FSH), and growth factors such as IGFs (eg IGF-1) and EGFs (including amphiregulin and epiregulin).

Accordingly, in another form the present invention provides a medium for improving developmental competence of an oocyte, the medium including one or more of the following components:
(i) one or more additional denuded oocytes;
(ii) one or more oocyte secreted factors;
(iii) GDF-9 and/or BMP-15 and/or BMP-6, or variants or analogues thereof;
(iv) an agent that increases the activity of a GDF-9 dependent signalling pathway in the oocyte and/or in a cumulus cell associated with the oocyte;
(v) an agent that increases the activity of a BMP-15 dependent signalling pathway in the oocyte and/or in a cumulus cell associated with the oocyte; and
(vi) an agent that increases the activity of a BMP-6 dependent signalling pathway in the oocyte and/or in a cumulus cell associated with the oocyte;
wherein the composition is substantially free of one or more of serum, albumin, follicular fluid, fetuin, follicle stimulating hormone (FSH), and growth factors.

The medium includes other suitable additives for the formulation of the medium. Preferably, the medium includes NaCl. More preferably, the medium includes 40 mM to 400 mM NaCl.

Preferably, the medium includes KCl. More preferably, the medium includes 0.1 mM to 20 mM KCl.

Preferably, the medium includes glucose. More preferably, the medium includes 0.1 mM to 40 mM glucose.

The present invention also provides a composition for use in assisted reproduction involving an oocyte.

An effective amount of one or more denuded oocytes, or the concentration of oocyte secreted factors that the oocyte and/or a cumulus cell associated with the oocyte is exposed to, may be chosen depending upon the degree of improved development required. Similarly, an effective amount of GDF-9 and/or BMP-15 and/or BMP-6 that the oocyte and/or a cumulus cell associated with the oocyte is exposed to may be chosen, as may an effective amount of an agent that increases the activity of a GDF-9 and/or BMP-15 and/or BMP-6 dependent signalling pathway in the oocyte and/or in a cumulus cell associated with the oocyte.

Examples of agents include drugs, small molecules, nucleic acids, oligonucleotides, polypeptides, peptides, proteins, enzymes, polysaccharides, glycoproteins, hormones, receptors, ligands for receptors, co-factors, antisense oligonucleotides, ribozymes, small interfering RNAs, lipids, antibodies or a part thereof, aptamers, or viruses.

In a preferred form, there is provided a composition for improving developmental competence of an oocyte, the composition including GDF-9 and/or BMP-15 and/or BMP-6, or variants or analogues thereof.

In a particularly preferred form, the composition is a medium.

In this regard, the term "variant" is to be understood to mean an amino acid sequence that is altered by one or more amino acids. The variant may have "conservative" changes, wherein a substituted amino acid has similar structural or chemical properties to the replaced amino acid (e.g., replacement of leucine with isoleucine). A variant may also have "non-conservative" changes (e.g., replacement of a glycine with a tryptophan) or a deletion and/or insertion of one or more amino acids.

Preferably, the variant has greater than 75% homology at the amino acid level with the native protein. More preferably, the variant has greater than 90% homology with the native protein. Most preferably, the variant has greater than 95% homology with the native protein.

The term "analogue" is to be understood to mean a molecule having similar structural, regulatory, or biochemical functions as that of the reference molecule, and includes a biologically active fragment of the reference molecule.

Preferably, the concentration of GDF-9 that the oocyte is exposed to is 1 to 1000 ng/ml. Preferably, the concentration of BMP-15 that the oocyte is exposed to is 1 to 1500 ng/ml.

Preferably, the concentration of BMP-6 that the oocyte is exposed to is 1 to 200 ng/ml. The method and composition are also suitable for in vitro maturation of an oocyte, and to improve oocyte quality.

Accordingly, there is also provided a method of modulating maturation of an oocyte and/or modulating quality of an oocyte, the method including one or more of the following steps:
(i) modulating the concentration and/or activity of oocyte secreted factors that the oocyte and/or a cumulus cell associated with the oocyte is exposed to;
(ii) modulating the concentration and/or activity of GDF-9 and/or BMP-15 and/or BMP-6 that the oocyte and/or a cumulus cell associated with the oocyte is exposed to;
(iii) modulating activity of a GDF-9 dependent signalling pathway in the oocyte and/or in a cumulus cell associated with the oocyte;
(iv) modulating activity of a BMP-15 dependent signalling pathway in the oocyte and/or in a cumulus cell associated with the oocyte; and
(v) modulating activity of a BMP-6 dependent signalling pathway in the oocyte and/or in a cumulus cell associated with the oocyte.

In this regard, there also provided an isolated oocyte with altered maturation and/or quality produced by the present method, and an embryo and a non-human animal produced from the oocyte.

In another form, there is also provided a composition for in vitro maturation of an oocyte and/or for improving quality of an oocyte, the composition including one or more of the following:
(i) one or more additional denuded oocytes;
(ii) one or more oocyte secreted factors;
(iii) GDF-9 and/or BMP-15 and/or BMP-6, or variants or analogues thereof,
(iv) an agent that increases the activity of a GDF-9 dependent signalling pathway in the oocyte and/or in a cumulus cell associated with the oocyte;
(v) an agent that increases the activity of a BMP-15 dependent signalling pathway in the oocyte and/or in a cumulus cell associated with the oocyte; and
(vi) an agent that increases the activity of a BMP-6 dependent signalling pathway in the oocyte and/or in a cumulus cell associated with the oocyte.

Preferably, the composition is a medium for the culturing of the oocyte.

The medium may be substantially free of one or more of serum, albumin, follicular fluid, fetuin, follicle stimulating hormone (FSH), and growth factors such as IGFs (eg IGF-1) and EGFs (including amphiregulin and epiregulin). Preferably, the medium is a serum-free medium.

In a preferred form, the medium includes GDF-9 and/or BMP-15 and/or BMP-6. Accordingly, there is also provided an oocyte culture medium, the medium including GDF-9 and/or BMP-15 and/or BMP-6.

In a preferred form, there is also provided an in vitro maturation medium for an oocyte, the medium including GDF-9 and/or BMP-15 and/or BMP-6.

This medium is also suitable to improve oocyte quality, and to improve oocyte developmental competence. Accordingly, there is also provided a medium for improving oocyte quality and/or improving oocyte development competence, the medium including GDF-9 and/or BMP-15 and/or BMP-6.

An example of a suitable media is Bovine Vitro Fert Medium or Bovine Vitro Blast Medium from Cook Australia supplemented with 10% v/v BMP-15 and/or 175 ng/ml GDF-9 and/or 10 ng/ml BMP-6.

The composition and/or medium is also particularly suitable for culturing oocytes that are used for assisted reproduction technologies.

Accordingly, in another form the present invention provides a method of assisted reproduction involving an oocyte, the method including the step of culturing the oocyte in a medium including one or more of the following:
(i) one or more denuded oocytes;
(ii) one or more oocyte secreted factors;
(iii) GDF-9 and/or BMP-15 and/or BMP-6, or variants or analogues thereof;
(iv) an agent that increases the activity of a GDF-9 dependent signalling pathway in the oocyte and/or in a cumulus cell associated with the oocyte;
(v) an agent that increases the activity of a BMP-15 dependent signalling pathway in the oocyte and/or in a cumulus cell associated with the oocyte; and
(vi) an agent that increases the activity of a BMP-6 dependent signalling pathway in the oocyte and/or in a cumulus cell associated with the oocyte.

For example, the present invention may be used in an in vitro fertilization technique.

Accordingly, in another form the present invention provides a method of in vitro fertilization of an oocyte, the method including the step of culturing the oocyte in a medium including one or more of the following:
(i) one or more denuded oocytes;
(ii) one or more oocyte secreted factors;
(iii) GDF-9 and/or BMP-15 and/or BMP-6, or variants or analogues thereof;
(iv) an agent that increases the activity of a GDF-9 dependent signalling pathway in the oocyte and/or in a cumulus cell associated with the oocyte;
(v) an agent that increases the activity of a BMP-15 dependent signalling pathway in the oocyte and/or in a cumulus cell associated with the oocyte; and
(vi) an agent that increases the activity of a BMP-6 dependent signalling pathway in the oocyte and/or in a cumulus cell associated with the oocyte.

The present invention also provides a composition for use in assisted reproduction involving an oocyte.

The method and composition is also suitable for modulating the development or developmental competence of an embryo produced by fertilization of the oocyte. II this regard, the oocyte may be treated at any time prior to, during and after fertilization.

Accordingly, there is also provided a method of improving development or developmental competence of an embryo produced from an oocyte, the method including one or more of the following steps:
(i) modulating the concentration and/or activity of oocyte secreted factors that the oocyte and/or a cumulus cell associated with the oocyte is exposed to;
(ii) modulating the concentration and/or activity of GDF-9 and/or BMP-15 and/or BMP-6 that the oocyte and/or a cumulus cell associated with the oocyte is exposed to;
(iii) modulating activity of a GDF-9 dependent signalling pathway in the oocyte and/, or in a cumulus cell associated with the oocyte;
(iv) modulating activity of a BMP-15 dependent signalling pathway in the oocyte and/or in a cumulus cell associated with the oocyte; and
(vi) modulating activity of a BMP-6 dependent signalling pathway in the oocyte and/or in a cumulus cell associated with the oocyte.

The embryo so produced is more likely to develop to the blastocyst or morula stage, and more likely to implant into the uterus after embryo transfer.

It will be appreciated that GDF-9 and/or BMP-15 and/or BMP-6, and/or the agent that increases the activity of a GDF-9 dependent signalling pathway in an oocyte, a cumulus cell associated with an oocyte or embryo, and/or the agent that increases the activity of a BMP-15 dependent signalling pathway in an oocyte, a cumulus cell associated with an oocyte or embryo, and/or the agent that increases the activity of a BMP-6 dependent signalling in an oocyte, a cumulus cell associated with an oocyte or embryo, may also be used as a culture medium supplement for an embryos and/or oocyte.

Accordingly, in another form the present invention provides a combination product including the following components:
an oocyte and/or embryo culture medium; and
GDF-9 and/or BMP-15 and/or BMP-6, or a variant or an analogue thereof; and/or
one or more oocyte secreted factors; and/or
an agent that increases the activity of a GDF-9 dependent signalling pathway in an oocyte, a cumulus cell associated with the oocyte; and/or an agent that increases the activity of a BMP-15 dependent signalling pathway in an oocyte, a cumulus cell associated with an oocyte or embryo; and/or an agent that increases the activity of a BMP-6 dependent signalling path way in an oocyte, a cumulus cell associated with an oocyte or an embryo;

wherein the components are provided in a form for addition of the components to the culture medium.

The combination product may be used for any of the stated applications herein described.

The culture medium and the other various components may be packaged separately in suitable containers (preferably sterilized) such as ampoules, bottles, or vials, either in multiuse or in unit forms. The containers may be hermetically sealed after being filled. The proteins components may be in isolated form, or in purified or semi-purified form, and may contain additional additives for the stability and/or use of the proteins. Methods for packaging the various components are known in the art.

It is also contemplated that the development and/or developmental competence of an embryo may be modulated.

Accordingly, there is also provided a method of improving development or developmental competence of an embryo, the method including one or more of the following steps:

(i) modulating the concentration and/or activity of oocyte secreted factors that the embryo is exposed to;

(ii) modulating the concentration and/or activity of GDF-9 and/or BMP-15 and/or BMP-6 that the embryo is exposed to;

(iii) modulating activity of a GDF-9 dependent signalling pathway in the embryo;

(iv) modulating activity of a BMP-15 dependent signalling pathway in the embryo; and (v) modulating activity of a BMP-6 dependent signalling pathway in the embryo.

The method may also be used to alter the developmental ability and/or developmental competence of an embryo.

In particular, this method may be used to improve development of an embryo from the point of fertilization to the blastocyst stage oocyte, by increasing one or more of (i) the concentration and/or activity of oocyte secreted factors that the embryo is exposed to; (ii) the concentration and/or activity of GDF-9 and/or BMP-15 and/or BMP-6 that the embryo is exposed to; and (iii) the activity of a GDF-9 and/or BMP-15 and/or BMP-6 dependent signalling pathway in the embryo.

Thus, an embryo is more likely to develop to the blastocyst or morula stage, and more likely to implant into the uterus after embryo transfer.

A suitable source of one or more oocyte secreted factors includes exposing the embryo to one or more additional denuded oocytes. Alternatively, the embryo may be exposed to a conditioned medium from one or more oocytes.

Preferably, modulation of the development and/or developmental competence of the embryo is by way of modulating the concentration of GDF-9 and/or BMP-15 and/or BMP-6 that the embryo is exposed to.

In this regard, the development and/or developmental competence of the embryo may be improved by increasing the concentration of GDF-9 and/or BMP-15 and/or BMP-6 that the embryo is exposed to.

Accordingly, in a preferred form there is provided a method of modulating development and/or developmental competence of an embryo, the method including the step of modulating the concentration of GDF-9 and/or BMP-15 and/or BMP-6 that the embryo is exposed to.

It will be appreciated that the modulation of the one or more steps may occur at any time after fertilization of the oocyte.

It will also be appreciated that the method may be used to modulate the development and/or developmental competence of an embryo either in vitro or in vivo. Preferably, the embryo is in vitro.

Methods are known in the art for producing embryos in vitro.

In this regard, there also provided an isolated embryo with altered development or developmental competence produced by the present method, and a non-human animal produced from the embryo.

An embryo with altered development or developmental competence produced in vitro may be used in an assisted reproduction technique, including being transferred to a suitable recipient female subject, or may be cultured in vitro while retaining viability for use in embryo transfer, genetic manipulation, or may be stored or frozen prior to embryo transfer or other manipulation. In addition, embryos produced from the embryo may be used as a source of embryonic cells for nuclear transfer or for embryonic stem cell production.

Accordingly, in another form there is provided a method of assisted reproduction involving an embryo, the method including the step of culturing the embryo in a medium including one or more of the following:

(i) one or more denuded oocytes;

(ii) one or more oocyte secreted factors;

(iii) GDF-9 and/or BMP-15 and/or BMP-6, or variants or analogues thereof;

(iv) an agent that increases the activity of a GDF-9 dependent signalling pathway in the embryo;

(v) an agent that increases the activity of a BMP-15 dependent signalling pathway in the embryo; and (vi) an agent that increases the activity of a BMP-6 dependent signalling pathway in the embryo.

The present invention also provides a composition for use in assisted reproduction involving an embryo.

In a preferred form, there is also provided a composition for improving development and/or developmental competence of an embryo, the composition including one or more of the following:

(i) one or more additional denuded oocytes;

(ii) one or more oocyte secreted factors;

(iii) GDF-9 and/or BMP-15 and/or BMP-6, or variants or analogues thereof;

(iv) an agent that increases the activity of a GDF-9 dependent signalling pathway in the embryo;

(v) an agent that increases the activity of a BMP-15 dependent signalling pathway in the embryo; and (vi) an agent that increases the activity of a BMP-6 dependent signalling pathway in the embryo.

In preferred form, the composition is a culture medium for an embryo.

Accordingly, there is also provided an embryo culture medium, the composition including one or more of the following:

(i) one or more additional denuded oocytes;

(ii) one or more oocyte secreted factors;

(iii) GDF-9 and/or BMP-15 and/or BMP-6, or variants or analogues thereof;

(iv) an agent that increases the activity of a GDF-9 dependent signalling pathway in the embryo;

(v) an agent that increases the activity of a BMP-15 dependent signalling pathway in the embryo; and (vi) an agent that increases the activity of a BMP-6 dependent signalling pathway in the embryo.

The medium may be substantially free of one or more of serum, albumin, follicular fluid, fetuin, follicle stimulating hormone (FSH), and growth factors such as IGFs (eg IGF-1) and EGFs (including amphiregulin and epiregulin).

Accordingly, in another form the present invention provides a medium for improving developmental competence of an embryo, the medium including one or more of the following components:
(i) one or more additional denuded oocytes;
(ii) one or more oocyte secreted factors;
(iii) GDF-9 and/or BMP-15 and/or BMP-6, or variants or analogues thereof;
(iv) an agent that increases the activity of a GDF-9 dependent signalling pathway in the embryo;
(v) an agent that increases the activity of a BMP-15 dependent signalling pathway in the embryo; and
(vi) an agent that increases the activity of a BMP-6 dependent signalling pathway in the embryo;
wherein the composition is substantially one or more of free of serum, albumin, follicular fluid, fetuin, follicle stimulating hormone (FSH), and growth factors.

The medium includes other suitable additives for the formulation of the medium.

Preferably, the medium includes NaCl. More preferably, the medium includes 40 mM to 400 mM NaCl.

Preferably, the medium includes KCl. More preferably, the medium includes 0.1 mM to 20 mM KCl.

Preferably, the medium includes glucose. More preferably, the medium includes 0.1 mM to 40 mM glucose.

An effective amount of one or more denuded oocytes, or the concentration of oocyte secreted factors that the oocyte and/or a cumulus cell associated with the oocyte is exposed to, may be chosen depending upon the degree of improved development required. Similarly, an effective amount of GDF-9 and/or BMP-15 and/or BMP-6 that the embryo is exposed to may be chosen, as may an effective amount of an agent that increases the activity of a GDF-9 and/or BMP-15 and/or BMP-6 dependent signalling pathway in the embryo.

Examples of agents include drugs, small molecules, nucleic acids, oligonucleotides, polypeptides, peptides, proteins, enzymes, polysaccharides, glycoproteins, hormones, receptors, ligands for receptors, co-factors, antisense oligonucleotides, ribozymes, small interfering RNAs, lipids, antibodies or a part thereof, aptamers, or viruses.

In a preferred form, there is provided a composition for improving development or developmental competence of an embryo, the composition including GDF-9 and/or BMP-15 and/or BMP-6, or variants or analogues thereof.

In a particularly preferred form, the composition is a medium.

Preferably, the concentration of GDF-9 that the embryo is exposed to is 1 to 1000 ng/ml.

Preferably, the concentration of BMP-15 that the embryo is exposed to is 1 to 1500 ng/ml.

Preferably, the concentration of BMP-6 that the embryo is exposed to is 1 to 200 ng/ml.

The method and composition are also suitable for increasing the likelihood that an embryo will progress to the blastocyst stage.

Accordingly, there is also provided a method of increasing the likelihood that an embryo will progress to the blastocyst stage, the method including one or more of the following steps:
(i) modulating the concentration and/or activity of oocyte secreted factors that the embryo is exposed to;
(ii) modulating the concentration and/or activity of GDF-9 and/or BMP-15 and/or BMP-6 that the embryo is exposed to;
(iii) modulating activity of a GDF-9 dependent signalling pathway in the embryo;
(iv) modulating activity of a BMP-15 dependent signalling pathway in the embryo; and
(v) modulating activity of a BMP-6 dependent signalling pathway in the embryo.

In this regard, there also provided an isolated embryo produced by the present method, and a non-human animal produced from the embryo.

In another form, there is also provided a composition for increasing the likelihood that an embryo will progress to the blastocyst stage, the composition including one or more of the following:
(i) one or more additional denuded oocytes;
(ii) one or more oocyte secreted factors;
(iii) GDF-9 and/or BMP-15 and/or BMP-6, or variants or analogues thereof;
(iv) an agent that increases the activity of a GDF-9 dependent signalling pathway in the embryo;
(v) an agent that increases the activity of a BMP-15 dependent signalling pathway in the embryo; and
(vi) an agent that increases the activity of a BMP-6 dependent signalling pathway in the embryo.

Preferably, the composition is a medium for the culturing of the embryo.

Accordingly, there is also provided an embryo culture medium including one or more of the following:
(i) one or more additional denuded oocytes;
(ii) one or more oocyte secreted factors;
(iii) GDF-9 and/or BMP-15 and/or BMP-6, or variants or analogues thereof;
(iv) an agent that increases the activity of a GDF-9 dependent signalling pathway in the embryo;
(v) an agent that increases the activity of a BMP-15 dependent signalling pathway in the embryo; and
(vi) an agent that increases the activity of a BMP-6 dependent signalling pathway in the embryo.

In a preferred form, the medium includes GDF-9 and/or BMP-15 and/or BMP-6. Accordingly, there is also provided an embryo culture medium, the medium including GDF-9 and/or BMP-15 and/or BMP-6.

This medium is also suitable to improve development and/or developmental competence of an embryo. Accordingly, there is also provided a medium for improving development and/or developmental competence of an embryo, the medium including GDF-9 and/or BMP-15 and/or BMP-6.

The medium may be substantially free of one or more of serum, albumin, follicular fluid, fetuin, follicle stimulating hormone (FSH), and growth factors such as IGFs (eg IGF-1) and EGFs (including amphiregulin and epiregulin).

Preferably, the medium is a serum-free medium.

An example of a suitable media is Bovine Vitro Fert Medium or Bovine Vitro Blast Medium from Cook Australia supplemented with 10% BMP-15 and/or 175 ng/ml GDF-9 and/or 10 ng/ml BMP-6.

Modulation of the activity of a GDF-9 and/or BMP15 and/or BMP-6, and/or their signalling pathways in an embryo may be by a method known in the art. Various methods are known in the art for determining the activity of these pathways in cells.

Modulating the concentration and/or activity of GDF-9 and/or BMP-15 and/or BMP-6 that an embryo is exposed to may be achieved in a number of different ways. For example, in the case of increasing the concentration of one or both of these proteins, the embryo may be exposed to, or contacted with, the proteins.

In this regard, it will be appreciated that the reference to BMP-15 includes the protein from a suitable species (including the protein from the same species as that of the oocyte or embryo), a variant of the protein (such as a form of the protein with one or more amino acid substitutions from that of the wildtype), or a biologically active fragment of the protein. The protein may be an isolated protein, a recombinant protein, purified or semi-purified, or as part of a complex mixture of proteins (such as occurs in conditioned medium from oocytes).

Similarly, the reference to GDF-9 includes the protein from a suitable species (including the protein from the same species as that of the oocyte or embryo), a variant of the protein (such as a form of the protein with one or more amino acid substitutions from that of the wildtype), or a biologically active fragment of the protein. The protein may be an isolated protein, a recombinant protein, purified or semi-purified, or as part of a complex mixture of proteins (such as occurs in conditioned medium from oocytes).

Similarly, the reference to BMP-6 includes the protein from a suitable species (including the protein from the same species as that of the oocyte or embryo), a variant of the protein (such as a form of the protein with one or more amino acid substitutions from that of the wildtype), or a biologically active fragment of the protein. The protein may be an isolated protein, a recombinant protein, purified or semi-purified, or as part of a complex mixture of proteins (such as occurs in conditioned medium from oocytes).

As discussed above, the proteins may be delivered as purified or semi-purified proteins. Methods for producing the proteins are blown in the art. Alternatively, the proteins may be delivered in the form of an extract containing one or more other components.

It is also possible to assess the developmental competence of an oocyte or embryo by determination of the concentration of GDF-9 and/or BMP-15 and/or BMP-6 that the oocyte or embryo is exposed to, and/or the activity of their dependent signalling pathways in the oocyte and/or embryo.

Accordingly, in another form the present invention provides a method of assessing the developmental competence of an oocyte, the method including the steps of:
(i) determining the concentration and/or activity of GDF-9 and/or BMP-15 and/, or BMP-6 that the oocyte and/or a cumulus cell associated with the oocyte is exposed to; and/or
(ii) determining the activity of a GDF-9 dependent signalling pathway in the oocyte and/or in a cumulus cell associated with the oocyte; and/or
(iii) determining the activity of a BMP-15 dependent signalling pathway in the oocyte and/or in a cumulus cell associated with the oocyte; and/or
(iv) determining the activity of a BMP-6 dependent signalling pathway in the oocyte and/or in a cumulus cell associated with the oocyte; and
(v) assessing the developmental competence of the oocyte by the concentration and/or activity of GDF-9 and/or BMP-15 and/or BMP-6 that the oocyte and/or a cumulus cell associated with the oocyte is exposed to, and/or the activity of the GDF-9 and/or BMP-15 and/or BMP-6 dependent signalling pathways in the oocyte or the cumulus cell;
wherein an increased concentration and/or activity of GDF-9 and/or BMP-15 and/or BMP-6 that the oocyte and/or a cumulus cell associated with the oocyte is exposed to, and/or an increased activity of the GDF-9 and/or BMP-15 and/or BMP-6 dependent signalling pathways in the oocyte or the cumulus cell is indicative of an oocyte with increased developmental competence, and a decreased concentration and/or activity of GDF-9 and/or BNP-15 and/or BMP-6 that the oocyte and/or a cumulus cell associated with the oocyte is exposed to, and/or an decreased activity of the GDF-9 and/or BMP-15 and/or BMP-6 dependent signalling pathways in the oocyte or the cumulus cell is indicative of an oocyte with reduced developmental competence.

In this case, improved developmental competence will be associated with a higher concentration and/or activity of GDF-9, and/or BMP-15 and/or BMP-6, and/or a higher activity of a GDF-9 and/or BMP-15 or BMP-6 signalling.

Methods for determining the concentration or activity of GDF-9 and/or BMP-15 and BMP-6, and methods for determining the activity of the appropriate signalling pathways are known in the art.

For example, during human IVF the oocytes used are usually denuded and the developmental competence of the oocyte may be assessed by determining the GDF-9 and/or BMP-15 and/or BMP-6 levels in the medium containing the oocyte prior to fertilization. A suitable method for determining the level of GFD-9 and/or BMP-15 and/or BMP-6 is by ElISA.

Accordingly, in another form the present invention provides a method for assessing the developmental competence of an oocyte, the method including the steps of:
(i) determining the level of expression of GDF-9 and/or BMP-15 and/or BMP-6 in the oocyte and/or determining the concentration of GDF-9 and/or BMP-15 and/or BMP-6 secreted by the oocyte; and
(ii) assessing the developmental competence of the oocyte;
wherein an increased expression and/or concentration of GDF-9 and/or BMP-15 and/or BMP-6 is indicative of an oocyte with increased developmental competency, and a decreased expression and/or concentration of GDF-9 and/or BMP-15 and/or BMP-6 is indicative of an oocyte with reduced developmental competency.

There is also provided a method of modulating expansion of a cumulus oocyte complex, the method including one or more of the following steps:
(i) modulating the concentration and/or activity of one or more of TGF-β1, GDF-9, BMP-15 and activin that the cumulus oocyte complex is exposed to; and
(ii) modulating the activity of a signalling pathway mediated by one or more of the AlK4, AlK5 and AlK7 receptors in the cumulus oocyte complex.

Modulation of the activity of a signalling pathway mediated by one or more of the AlK4, AlK5 and AlK7 receptors in the cumulus oocyte complex may be for example by modulating the level and/or activity of either or both of the intracellular signalling molecule Smad2 and Smad3 in the cumulus oocyte complex.

The modulation of expansion of the cumulus oocyte complex may occur in vitro or in vivo.

In a preferred form, the modulation of the cumulus expansion is achieved by exposing the cumulus oocyte complex to an agent that has the capacity to modulate either or both of (i) the concentration and/or activity of one or more of TGF-β1, GDF-9, BMP-15 and activin that the cumulus oocyte complex is exposed to; and (ii) the activity of a signalling pathway mediated by one or more of the AlK4, AlK5 and AlK7 receptors. There is also provided a composition for modulating expansion of a cumulus oocyte complex, the composition including such an agent.

In the case of a cumulus oocyte complex in vivo, the method is also suitable for modulating ovulation in a female subject. For example, die female subject may be a female human, a female mammal including a primate, a livestock animal (eg. a horse, cow, a sheep, a pig, a goat), a companion animal (eg. a dog, a cat), or a laboratory test animal (eg. a mouse, a rat, a guinea pig).

Accordingly, there is also provided a method of modulating ovulation in a female subject, the method including the step of administering to the female subject one or more of the following:
(i) an agent that modulates the concentration and/or activity of one or more of TGF-β1, GDF-9, BMP-15 and activin that a cumulus oocyte complex in the female subject is exposed to; and
(ii) an agent that modulates the activity of a signalling pathway mediated by one or more of the AlK4, AlK5 and AlK7 receptors in a cumulus oocyte complex in the female subject.

There is also provided a composition for modulating ovulation in a female subject, the composition including an agent that has the capacity to modulate either or both of (i) the concentration and/or activity of one or more of TGF-β1, GDF-9, BMP-15 and activin that a cumulus oocyte complex in the female subject is exposed to; and (ii) the activity of a signalling pathway mediated by one or more of the AlK4, AlK5 and AlK7 receptors in a cumulus oocyte complex in the female subject.

The method is also suitable for modulating fertility in a female subject.

Accordingly, there is also provided a method of modulating fertility in a female subject, the method including the step of administering to the female subject one or more of the following:
(i) an agent that modulates the concentration and/or activity of one or more of TGF-β1, GDF-9, BMP-15 and activin that a cumulus oocyte complex in the female subject is exposed to; and
(ii) an agent that modulates the activity of a signalling pathway mediated by one or more of the AlK4; AlK5 and AlK7 receptors in a cumulus oocyte complex in the female subject.

There is also provided a composition for modulating fertility in a female subject, the composition including an agent that has the capacity to modulate either or both of (i) the concentration and/or activity of one or more of TGF-β1, GDF-9, BMP-15 and activin that a cumulus oocyte complex in the female subject is exposed to; and (ii) the activity of a signalling pathway mediated by one or more of the AlK4, AlK5 and AlK7 receptors in a cumulus oocyte complex in the female subject.

For example, the method is suitable for reducing fertility in a female subject, by the use of an agent that an agent that has the capacity to inhibit either or both of (i) the concentration and/or activity of one or more of TGF-β1, GDF-9, BMP-15 and activin that a cumulus oocyte complex in the female subject is exposed to; and (ii) the activity of a signalling pathway mediated by one or more of the AlK4, AlK5 and AlK7 receptors in a cumulus oocyte complex in the female subject.

There is also provides a contraceptive composition including such an agent.

DESCRIPTION OF THE PREFERRED EMBODIMENTS

Reference will now be made to experiments that embody the above general principles of the present invention. However, it is to be understood that the following description is not to limit the generality of the above description.

Study 1 Oocyte Secreted Factors Prevent Cumulus Cell Apoptosis

EXAMPLE 1

Collection of Bovine Oocyte and Culture Conditions (Collection and Preparation of COC)

Unless specified, all chemicals and reagents were purchased from sigma (St lois Mo.).

Bovine ovaries were collected from local abattoir and transported to the laboratory in warm saline (30-35° C.). Cumulus-oocyte complexes (COC) were aspirated from antral follicles (2- to 8-mm diameter) using an 18-gauge needle and a 10-ml syringe containing ~2 ml aspiration media (Hepes-buffered Tissue Cultured Medium-199: TCM-199, ICN Biochemicals, Irvine, Calif., USA) supplemented with 50 µg/ml kanamycin (Sigma-Aldrish, St. louis, Mo.), 4 mg/ml fatty acid-free bovine serum albumin (FAF-BSA) (ICPbio ltd, Auckland, NZ). Intact COC with compact cumulus vestment greater than five cell layers and evenly pigmented cytoplasm were selected under a dissecting microscope and washed twice in Hepes-buffered TCM-199 and once in corresponding culturing media. Complexes were cultured with or without 0.1 IU/ml FSH (Organon, Netherlands) in pre-equilibrated 50 µg drops of culture media (bicarbonated-buffered TCM-199 supplemented with 0.23 mmol sodium pyruvated $1^{-1}$, 0.3 mg/ml polyvinyl alcohol (PVA; sigma, St louis, Mo.) overlaid with mineral oil and incubated at 39° C. with 5% CO2 in humidified air for 24hour.

EXAMPLE 2

Treatment of Cumulus Cells (i) Generation of Oocytectomized Complexes

The cytoplasm of each oocyte was microsurgically removed from the COC (oocytectomy) using a micromanipulator as described in Buccione et al (Buccione et al. (1990) *Dev Biol* 138, 16-25.). The resulting oocytectomized complex (OOX) consists of a hollow zona pellucida surrounded by several layers of intact CC.

(ii) Generation of Denuded Oocytes

Denuded oocytes (DO) were generated by removing CC from COC by vortexing for approximately 4 minutes in 2 ml H-TCM-199/BSA. Any remaining CC were removed by repeated passage of the oocytes through a fine-bore fire-polished glass pipette in H-TCM-199/BSA.

(iii) Growth factors and binding proteins

Recombinant mouse GDF-9 and recombinant ovine BMP-15 were produced in-house as previously described (Kaivo-Oja et al (2003) *J Clin Endocrinol Metab* 88, 755-62; McNatty et al (2005) *Reproduction* 129:473-480) using transfected 293 human embryonic kidney cell lines (293H). Recombinant proteins were partially purified using hydrophobic interaction chromatography (HIC), and their concentrations were then estimated by Western blot (Kaivo-Oja et al (2003) *J Clin Endocrinol Metab* 88: 755-62). Control conditioned medium (293H) was also produced from untransfected 293H cells and purified by HIC. Recombinant human BMP-6, recombinant human BMP-7, BMP-6 neutralizing antibody, and gremlin were obtained from R&D systems (Minneapolis, Minn.).

EXAMPLE 3

Determination of DNA Damage by TUNEL (Assessment of Apoptosis in Cumulus Cells by TUNEL)

CC apoptoic DNA was detected using TUNE1 (Roche Diagnostic, Penzberg, Germany) according to the manufacturer's instructions. Briefly, following culture COC and OOX complexes were washed twice in PBS (pH 7.4) containing 1% BSA, fixed in 4% paraformaldehyde in PBS (pH 7.4) overnight at 4° C. and washed twice with PBS/BSA before placing on Cell-Tak-coated coverslips (Beckton Dickinson Biosciences, Franklin lakes, N.J.). Complexes were then permeabilized in 0.11/u Triton X-100 in 0.1% sodium citrate for 1 hour at room temperature and washed 3 times in PBS/BSA. The complexes were then incubated in fluorescein-conjugated dUTP and terminal deoxynucleotide transferase (TUNE1 reagents, Roche) for 1 hour at 37° C. in the dark. Positive controls were incubated in DNAse 1 (0.005 U/□l), which cleaves all DNA, for 20 minutes at room temperature and washed twice in PBS/BSA before TUNE1. Negative controls were incubated in fluorescein-dUTP in the absence of TdT. After TUNE1, complexes were washed twice in PBS/BSA and counterstained with propidium iodide 0.5 µg/ml (PI) plus RNase A (0.1 mg/ml) for 1 hour at room temperature in the dark to label all nuclei. Complexes were then washed twice in PBS/BSA and mounted with slight coverslip compression in VectaShield anti-bleaching solution (Vector labs, Burlingame, Calif.), and stored in the dark at 4° C. for confocal analysis.

EXAMPLE 4

Confocal Microscopy and Analysis

Apoptosis in COC and OOX was visualised and quantified using confocal microscopy. Dual fluorescence emission from CC was detected using a Nikon C1 Confocal Scanning Head and a Nikon TE2000E microscope (Nikon, Tokyo, Japan). Simultaneous emission capture of the apoptotic signal (fluorescein, lacer excitation 488 nm, emission 510-530 nm) and the nuclear signal (propidium iodide, excitation lacer 532, emission 590-640 nm) was performed.

In order to generate an accurate representation of the overall apoptotic incidence for all complexes, the depth of each complex was measured through a Z series to divide the construct into three percentiles (optical Z plane sections) at 25%, 50% and 75%. These optical section images were acquired and saved as independent colour channels (green, apoptotic cumulus fluorescence and red, nuclear cumulus fluorescence). The captured images were then processed in Scanalytics IPlab software Version 3.6. (Scanalytics, Fairfax, Va.). Quantification of CC number (for each colour channel) was independently measured using a macro script utilizing an auto segmentation filter for each optical section percentile (3 optical "z"-plane sections for each complex). A percentage of apoptotic nuclei were generated for each slice and the three percentile values were then averaged to achieve a representation of the total apoptotic nuclei percentage for the whole complex. These processes were repeated separately on each individual complex.

EXAMPLE 5

Western Blot Analysis

Following culture treatments, OOX complexes were lysed in 25 ml RIPA lysis buffer (10 mM Tris [pH 7.4], 150 mM NaCl, 1 mM EDTA, 1% Trinton X-100 and stored at −80° C., for detection of apoptotic proteins using the sensitive Enhanced Chemiluminescence (ECl) Advance system (Amersham Biosciences, Ontario, Canada). Thawed lysates were mixed with 4× loading buffer containing 100 mM Dithiothretol (DTT) and subjected to SDS-PAGE (12% polyacrylamide gel). Proteins were subsequently electrotransferred to nitrocellulose membranes (Hybond-ECl, Amersham life Science, Ontario, Canada.) in 25 mM Tris-192 mM glycine containing 20% methanol. Blots were blocked in 20 mM Tris (pH 7.6) containing 13.7 mM NaCl, 1% Tween-20, and 2% blocking agent (provided in ECl Advance Kit) for 1 hr at RT, then incubated overnight with Bcl-2 or Bax rabbit polyclonal antibodies (0.35 µg/ml; Santa Cruz Biotechnology, Calif., USA) at 4° C., followed by incubation with horseradish peroxidase-conjugated anti-rabbit antibody (1:200 000; Silemus laboratories, Melbourne, Australia). Images were then scanned using a flat bed scanner and the intensity of Bcl-2 and Bax bands in each sample was quantitated by the ImageJ Imaging System Software version 1.3 (National Institutes of Health, USA).

EXAMPLE 6

Effect of Oocytectomy on Cumulus Cell Apoptosis

To determine whether intact COC have a different level of apoptosis to OOX, groups of 5 COC or OOX were cultured in 50 µl drops of culture media for 24 h before apoptosis was assessed. Six replicate experiments were performed.

Figure 1B:
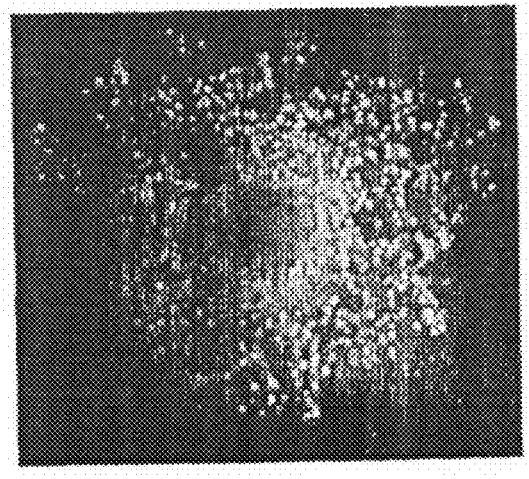
Figure 1C:
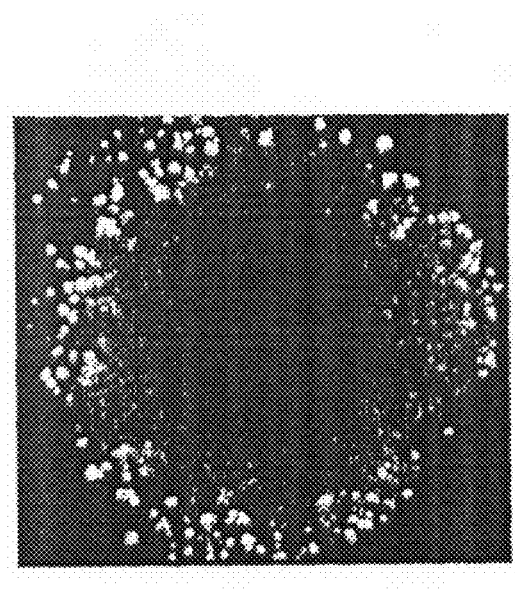
Figure 1D:
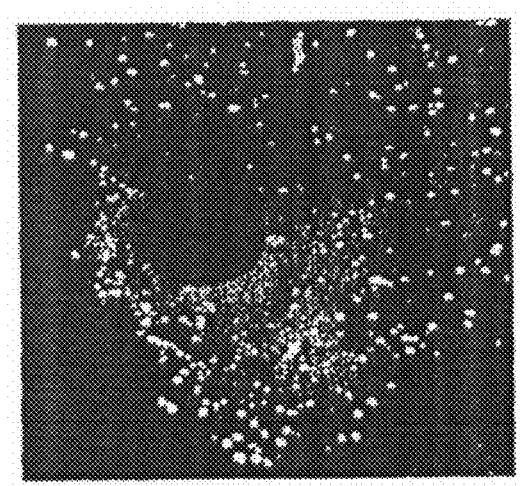
Figure 2A:
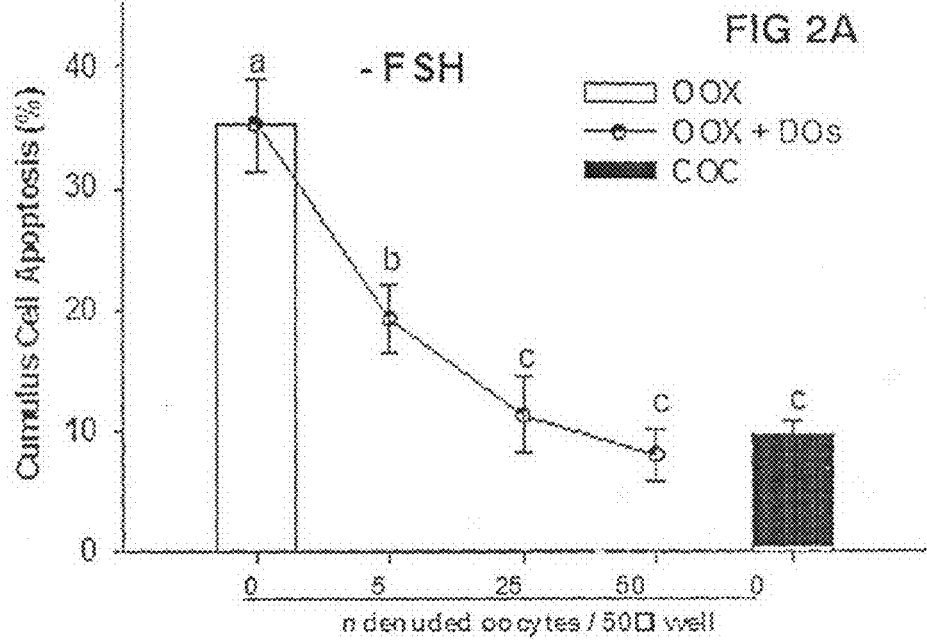
FIGS. 2A and 2B show dose response of oocyte-secreted factors on cumulus cell apoptosis in the presence (A) or absence (B) of FSH. Oocytectomized complexes (OOX) were cultured with increasing numbers of denuded oocytes (DO) and at the maximum dose were effective at reducing apoptosis to the control COC levels, Points represent average percentage of apoptotic cumulus cells (mean±SEM). Values from points with different labels $^{a,\ b,\ c}$ differ significantly ($p<0.001$).

TUNEL coupled with confocal scanning microscopy proved a highly effective means of visualising and quantifying CC apoptosis. TUNEL positive and negative controls (FIGS. 1A and 1B; 99% and 0% apoptosis, respectively) demonstrated specificity. COCs exhibited a low incidence of CC apoptosis (9%; FIG. 1C), and removal of the oocyte led to a significant increase to 35% in OOXs (p<0.001; FIG. 1D). Supplementation of media with FSH significantly decreased the incidence of apoptosis in OOXs (by 10%) and in COCs (by 6%) (p<0.001; FIG. 2).

EXAMPLE 7

Effect of Oocyte-Secreted factors on Cumulus Cell Apoptosis

To determine whether OSF are responsible for the low incidence of apoptosis in CC of intact COC, OOX were cultured with increasing numbers of DO and compared to COC. 5, 25 or 50 DO were added to 50 µl culture drops containing 5 OOX. Three replicate experiments were performed.

To determine if oocyte paracrine factors are responsible for low COC apoptosis, an attempt was made to reduce the incidence of apoptosis in OOX to COC levels, by co-culturing OOXs with increasing concentrations of DOs. CC apoptosis was significantly reduced (p<0.001), in a dose-dependent manner, by incubating OOXs with increasing numbers of DOs. Apoptotic levels in OOXs were completely restored to COC levels at the maximum number of DO (50 DO/well), whether in the presence or absence of FSH. (FIG. 2). These results indicate that OSF prevent apoptosis within CC.

EXAMPLE 8

Pattern of Apoptosis in relation to the Proximity of OSF Origin

To determine the distribution of apoptosis within the CC complex in relation to the complex's proximity to the oocyte, we quantified the apoptotic incidence in COCs, where the origin of the OSF is central to the CC complex, and in contrast, in OOXs co-cultured with DOs, where the origin of the OSF is on the outside of the CC complex. Using the confocal microscope, the diameter of complexes was measured alter the diameter of the oocyte region was subtracted using Scanalytics IPLab software Version 3.6. This was then divided into 3 equal layers; inner, middle and outer CC layers, forming 3 ring zones around the oocyte. Each layer was equivalent to a proportion of 33% of the total radius. The incidence of apoptosis was then analysed independently in each layer.

Figure 3A:
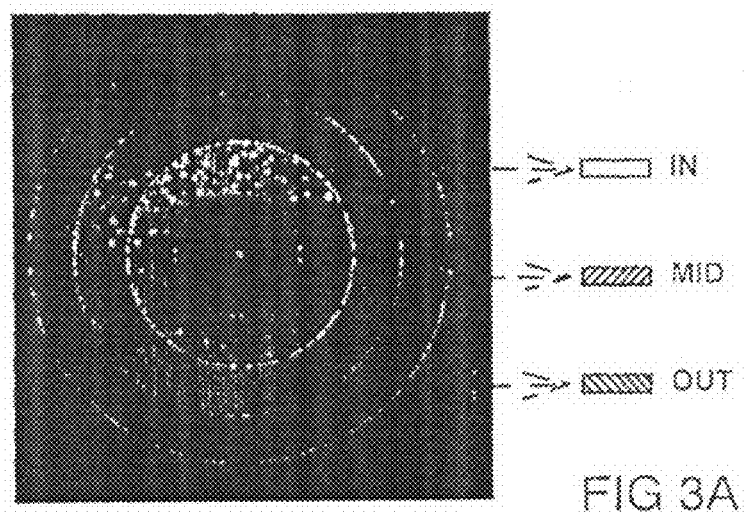
FIGS. 3A to 3D show the pattern of apoptosis within cumulus complexes in relation to proximity to OSF origin. Diameters of COCs and OOXs were measured using confocal microscopy and divided into 3 layers; inner, middle and outer layers, each layer representing 33% of the radius (A). The incidence of apoptosis was lowest closest to the oocyte, COC inner layer; in contrast to [D], OOX outer layer) and increased with increasing distance from the oocyte (B). *Treatment X layers (2-way ANOVA; $P=0.026$).
Figure 3B:
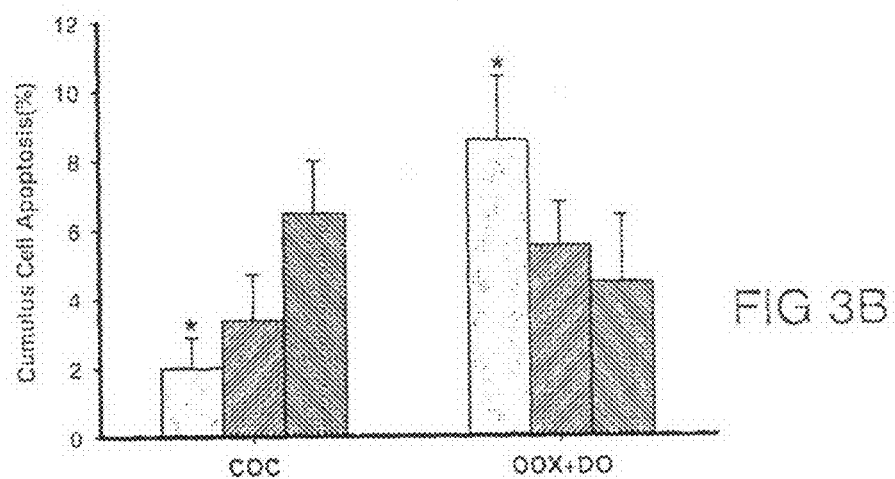
Figures 3C, 3D:
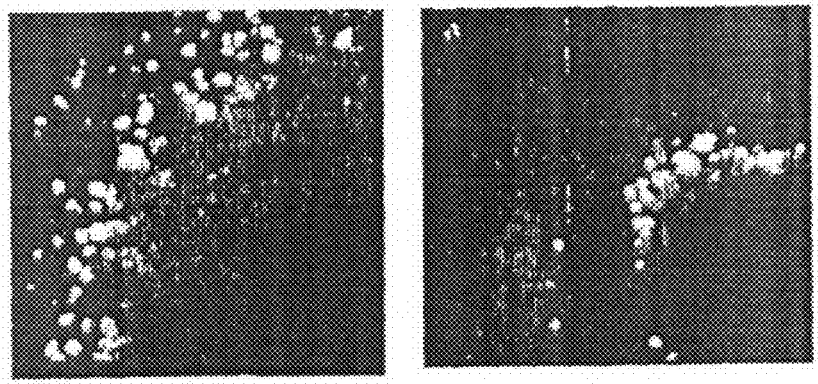

Qualitative observations of confocal images suggested that the apoptotic cells within COCs were mostly distributed to the outer layer of complexes, whereas apoptosis was observed in the inner cumulus layers when OOXs were co-cultured with DOs. We therefore hypothesized that OSF establish an anti-apoptotic morphogenic gradient through the CC layers. To test this hypothesis, we measured the diameter of COC and OOX complexes and then divided them into 3 layers; inner, middle and outer (FIG. 3A). Within COCs, which contain an intact oocyte, the incidence of apoptosis increased significantly ($P<0.026$) from the inner layer toward the outer layer (FIGS. 3B and 3C). Conversely, when OOXs were co-cultured with DOs, the incidence of apoptosis decreased from the inner layer toward the outer layer, which is closest to the source of OSFs (FIGS. 3B and 3D). To further illustrate this effect, the inner layer in COC, which is closest to the oocyte and has the lowest incidence of apoptosis, has a 4-fold and significantly ($P<0.026$) lower incidence of apoptosis, compared to its counterpart inner layer from the OOX+DO group, which has the highest incidence of apoptosis, being the furthest layer from the DOs (FIG. 3B).

EXAMPLE 9

Dose Response of GDF-9, BMP-6, BMP-15 on Cumulus Cell Apoptosis

In an attempt to examine which of the putative OSFs may be contributing to the low incidence of apoptosis observed in COC, OOX were cultured with increasing concentrations of either GDF-9 (0-175 ng/ml), BMP-6 (0-100 ng/ml) or BMP-15 (0-20% v/v), either in the absence or presence of FSH. OOX were also treated with 10% (X/v) 293H, which served as a parent cell line-conditioned media negative control for GDF-9 (equivalent to 132 ng/ml) and BMP-15 equivalent to 10% (v/v). Three replicates of these experiments were performed using 10 OOX per treatment group per replicate experiment.

Figure 4A:
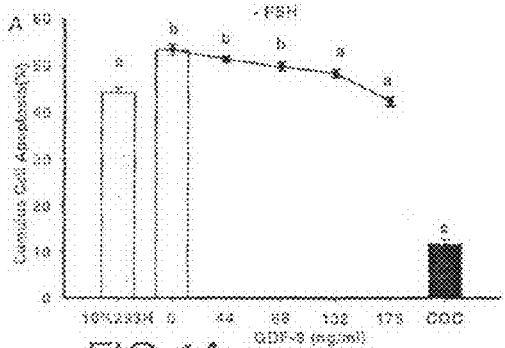
FIGS. 4A to 4D show the dose response of the putative oocyte-secreted factors; GDF-9, BMP-6, BMP-15 on cumulus cell apoptosis. OOX were cultured with increasing concentrations of GDF-9 (0-175 ng/ml), BMP-6 (0-100 ng/ml), and BMP-15 (0-20% v/v), either in the absence (A, C, E) or presence (B, D, F) of FSH. Cumulus cell apoptosis was unaffected by GDF-9 and attenuated in a dose-dependent manner by BMP-6, but more notably by BMP-15. Points represent average percentage of apoptotic cumulus cells (mean±SEM). Values from points with different labels $^{a,\ b,\ c}$ differ significantly (A-B; $p<0.001$). Asterisks represent significant difference ($p<0.001$) relative to the control (OOX) for that factor (C-F).
Figure 4B:
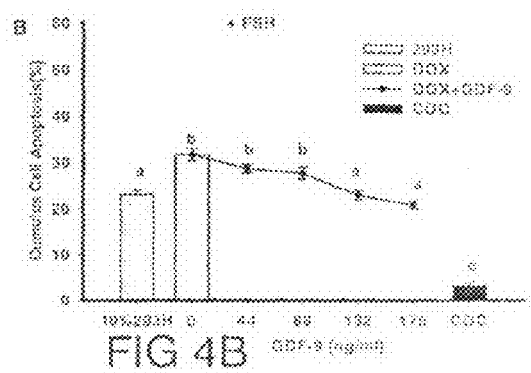
Figure 4C:
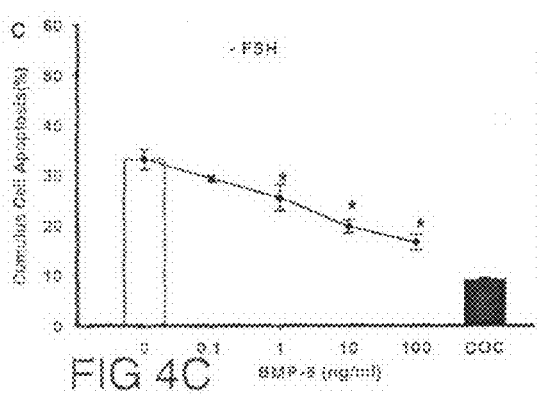
Figure 4D:
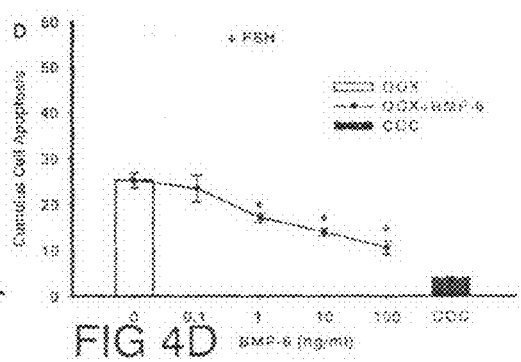
Figure 4E:
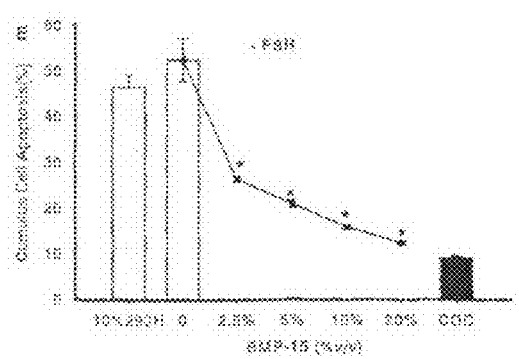
Figure 4F:
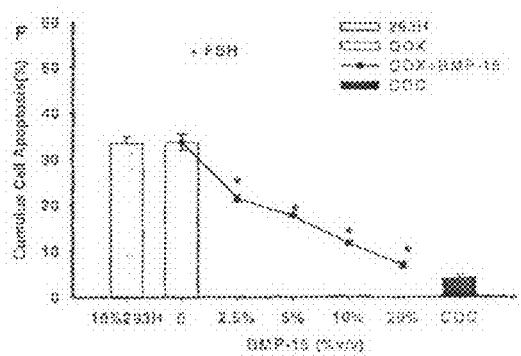

These experiments were conduct to determine the effect of these putative OSF on the regulation of CC apoptosis. OOX complexes were treated with increasing doses of GDF-9, BMP-6 and BMP-15. GDF-9 had no significant effect on the incidence of CC apoptosis in the presence or absence of FSH, as at the highest dose (175 ng/ml) of GDF-9, apoptosis was not significantly different to the 293H control conditioned medium group (FIGS. 4A, 4B). With an increasing dose of BMP-6, CC apoptosis significantly decreased ($P<0.001$), whether in the presence or absence of FSH (FIGS. 4C, D). CC apoptosis was significantly reduced ($p<0.001$) in a dose-dependent manner, by treating OOX with an increasing dose of BMP-15, having maximal effect at 20% BMP-15 (FIG. 4E). A similar response was observed when BMP-15 was used in combination with FSH (FIG. 4F).

EXAMPLE 10

Effect of DO, GDF-9 and BMP-15 on OOX Expression of Bcl-2 and Bax Proteins

This experiment was conducted to confirm that treatment effects on CC apoptosis, as assessed by TUNEL, are concomitant with changes in expression of key proteins regulating cell death and survival. OOX were cultured for 24 h untreated, or treated with 132 ng/ml GDF-9, 10% v/V BMP-15, co-cultured with 35 DO/well, or 10% 293H (control conditioned medium), and then subjected to Western blot for analysis of Bcl-2 and Bax expression.

Figure 5:
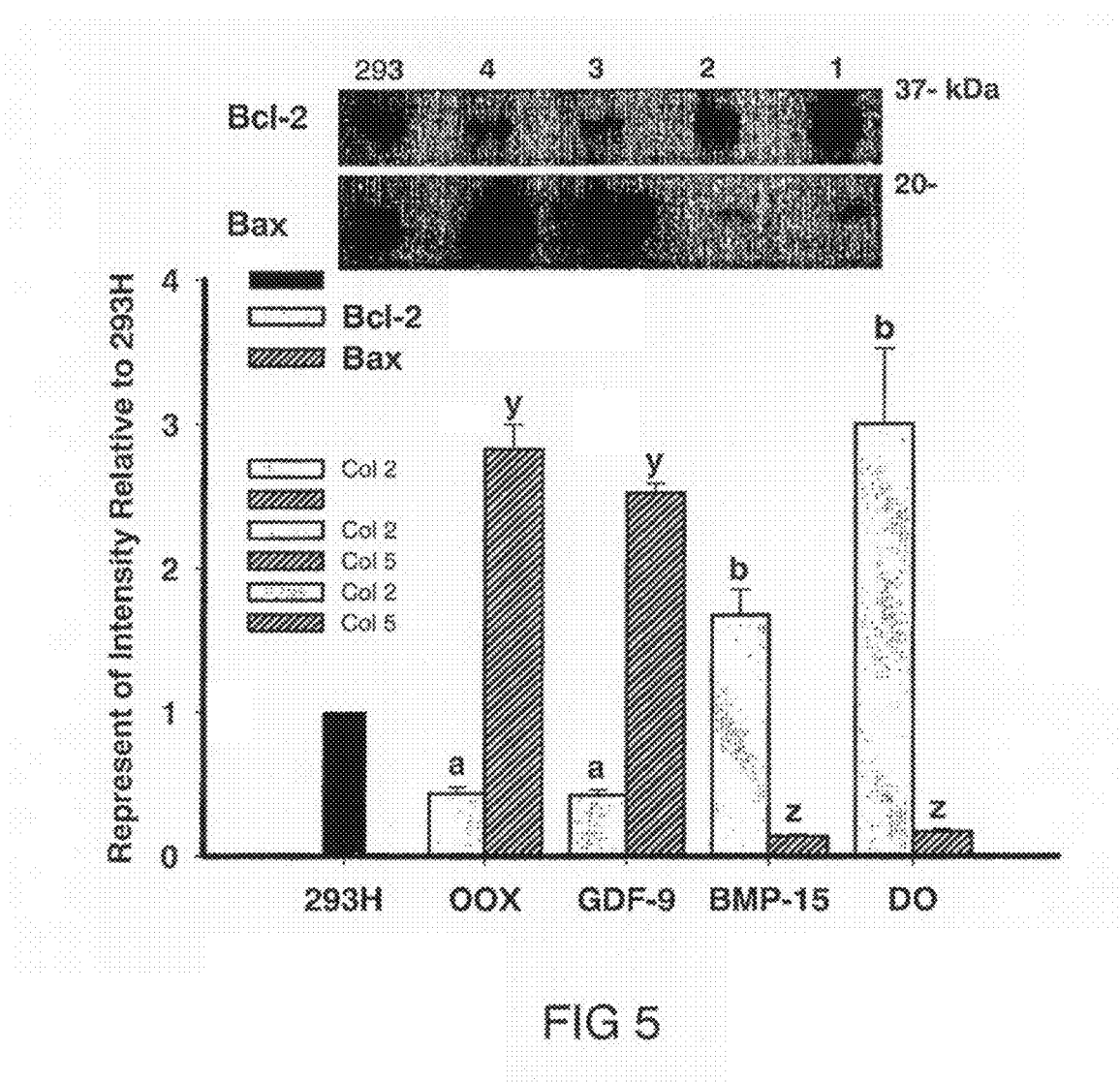
FIG. 5 shows the effect of DO, GDF-9 and BMP-15 on OOX expression of Bcl-2 and Bax proteins as examined by Western blot analysis. Groups of 35 OOX were loaded in each lane after the following treatments: lane 1, 10% v/v 293H (control conditioned medium); lane 2, control (OOX alone); lane 3, 132 ng/ml GDF-9; lane 4, 10% v/v BNP-15; lane 5, 0.7 DO/µl. Band intensities were quantified by densitometry and are expressed relative to the 293H control, from three replicate experiments (mean±SEM). Bars with different-superscripts within a group ($^{a-b}$ Bcl-2, $^{y-z}$ Bax) are significantly different ($P<0.001$).

This experiment was conducted to study the pattern of Bcl-2 and Bax expression in CC of OOX complexes. Expression of Bcl-2 protein was significantly ($P<0.001$) higher in CC when OOX were co-cultured with DO and BMP-15 compared to when untreated or treated with GDF-9 (FIG. 5). In contrast, expression of Bax protein was found to be significantly ($P<0.001$) higher in CC when OOX were untreated or co-cultured with GDF-9 compared to OOX co-cultured with DO or BMP-15, where Bax levels were barely detectable (FIG. 5). These results support our TUNEL results; namely that DO and BMP-15, but not GDF-9, are associated with the prevention of CC apoptosis, and that DO and BMP-15 alter the ratio of Bcl-2 to Bax in favour of cell survival (Oltvai et al., 1993), whereas GDF-9 has no effect on the Bcl-2 to Bax ratio.

EXAMPLE 11

Effect of DO, BMP-6, and BMP-15 on Cumulus Cell Apoptosis Induced by Staurosporine A preliminary experiment was conducted to determine the apoptotic effect of staurosporine on bovine CC, which induced apoptosis in a dose-dependent manner (range; 0.1-100 μM, data not shown). The aim of this experiment was to determine whether OSF could prevent CC from undergoing apoptosis induced by staurosporine. OOX alone or co-cultured with 35 DO, 10 ng/ml BMP-6 or 10% (v/v) BMP-15, and were then exposed to either 0.1 μM or 1.0 μM staurospourine for the last 6 hours of the 24 hour incubation period. Three replicates of this experiment were carried out using 10 OOX per treatment group per replicate experiment.

Figure 6:
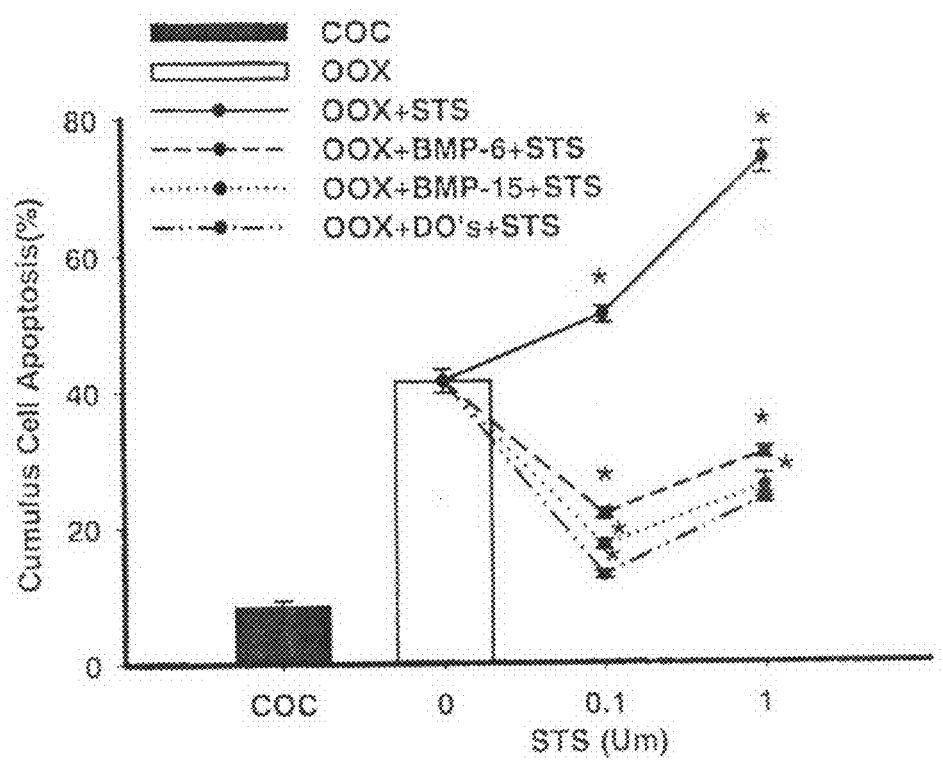
FIG. 6 shows protection of cumulus cells from staurosporine-induced apoptosis by DO, BMP-6 and BMP-15. OOX alone or co-cultured with 35 DO, 10 ng/ml BMP-6, or 10% v/v BMP-15, were exposed to either 0.1 µM or 1.0 µM staurosporine (STS) in the last 6 hours of incubation. Oocytes, BMP-6 and BMP-15 all prevented staurosporine-induced cumulus cell apoptosis. Asterisks represent OOX means significantly different ($p<0.001$) relative to the OOX control.
Figure 10:
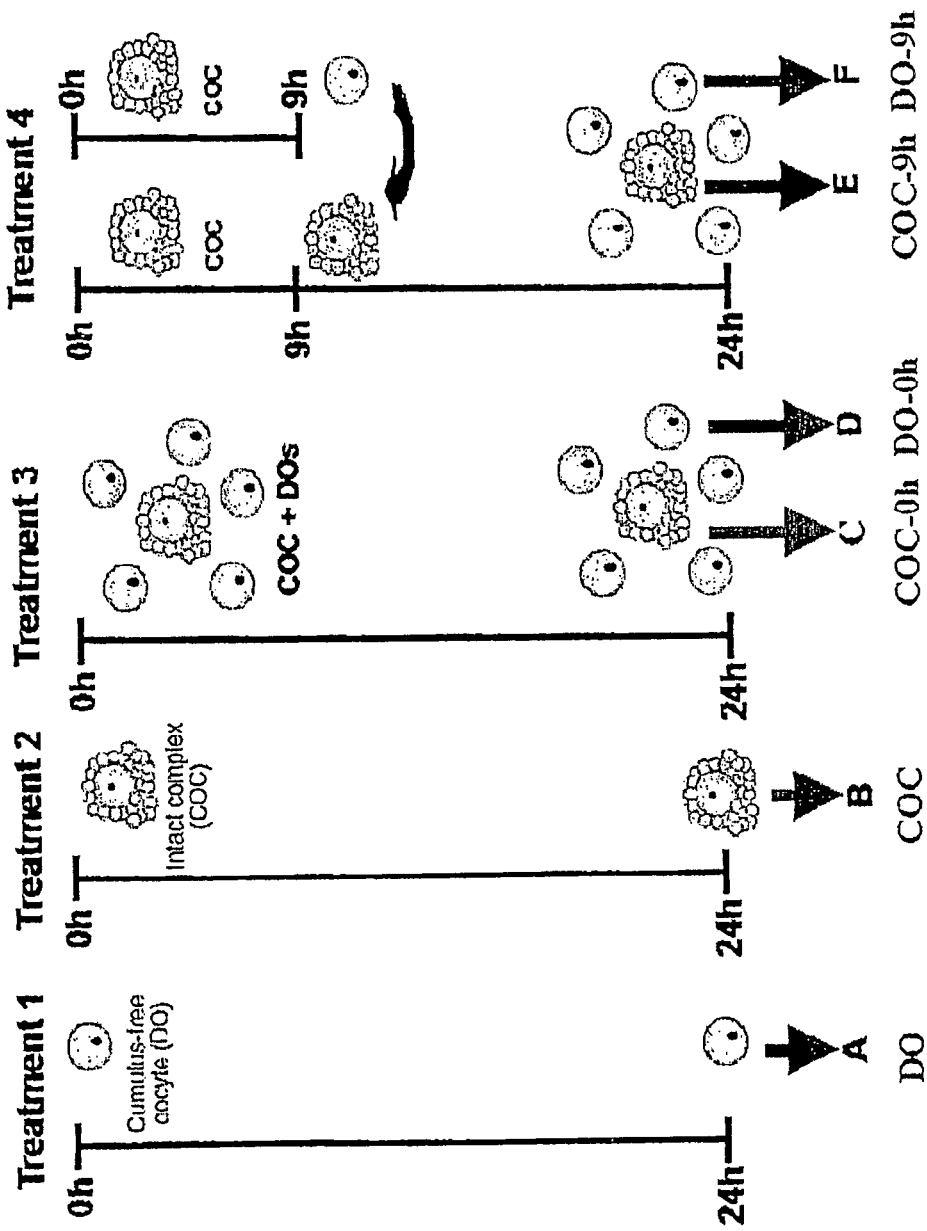
FIG. 10 shows the results of co-culture of cumulus-oocyte complexes in presence or absence of denuded oocytes during IVM. Complexes and oocytes were divided into 6 treatment groups after IVM. Denuded oocyte (A), Cumulus-oocyte complex (B), cumulus-oocyte complexes co-culture with denuded oocytes at 0 hour (C), denuded oocytes co-culture with cumulus-oocyte complexes at 0 hour (D), cumulus-oocyte complexes for 9 hour, then co-culture with denuded oocyte for the last 15 hour of IVM (E), cumulus-oocyte complexes for 9 hour prior to denuding, then co-culture with cumulus-oocyte complexes for the last 15 hour of IVM (F).

The aim of this experiment was to determine whether oocytes are capable of protecting CC from an apoptosis-inducing event and whether such an effect can by mimicked by BMP-15 and BMP-6. Staurospourine significantly increased ($P<0.001$) the incidence of CC apoptosis from 41% to 51 and 74% when treated with 0.1 and 1.0 μM respectively (FIG. 6). The apoptosis-inducing effects of both doses of staurosporine were completely negated when staurosporine-treated OOXs were co-cultured with DOs, with apoptosis reduced to COC levels. Also, OOX treated with 10% BMP-15 or 10 ng/ml BMP-6, exposed to the same 2 doses of staurosporine, showed significantly decreased apoptosis; 17% and 21% (0.1 μM); 25% and 31% (1 μM), respectively ($P<0.001$). These results indicate that the anti-apoptotic actions of OSF can protect CC from an apoptotic insult and that both BMP-15 and BMP-6 can mimic this effect.

EXAMPLE 12

Effect of BMP Antagonists on Cumulus Cell Apoptosis

Follistatin binds to both BMP-15 and activin with high affinity and antagonizes their bioactivity (Lin et al., 2003; Otsuka et al., 2001). Gremlin is expressed in both mural GC and CC and selectively blocks BMP-4 and BMP-7 (Merino et al., 1999), and may antagonize BMP-15. The aim of this experiment was, to examine the effectiveness of these antagonists against BMP-6 and BMP-15-prevented CC apoptosis. OOX were cultured with 10% (v/v) BMP-15 in the presence of increasing doses of follistatin (0-100 μg/ml) or in the presence of increasing doses of gremlin (0-40 μg/ml). In a separate experiment, OOX were treated with 10 ng/ml BMP-6 in the absence or presence of a high dose (20 μg/ml) of a BMP-6 monoclonal neutralizing antibody (NAb). Three replicates of each of these experiments were carried out using 10 OOX per treatment group per replicate experiment.

These experiments were conduct to examine whether BMP-15 and BMP-6 antagonists could neutralize the anti-apoptotic effects of BMP-15 and BMP-6 on CC apoptosis.

There was a significant ($P<0.001$), dose-dependent increase in apoptosis when BMP-15-treated OOXs were cultured with increasing concentrations of follistatin (FIG. 7A). OOX complexes cultured with 10 ng/ml BMP-6 were treated with a high dose (20 μg/ml) of a BMP-6 neutralizing antibody. FIG. 7B illustrates that the BMP-6 antagonist significantly ($P<0.001$) neutralized the anti-apoptotic effect of 10 ng/ml BMP-6.

EXAMPLE 13

Role of BMP-15 and BMP-6 in the Anti-Apoptotic Actions of Oocytes on Cumulus Cells In an attempt to neutralize the anti-apoptotic bioactivity of oocytes on CC. OOX were co-cultured with 25 DO, either in the absence or presence of 50 μg/ml follistatin, 20 μg/ml BMP-6 NAb, or in the presence of both antagonists. A separate experiment was conducted to examine any additive effects of BMP-15 and BMP-6, compared to OOX+DO. OOX were treated DO, or with 10 ng/ml BMP-6 and/or 10% v/v BMP-15. Three replicates of these experiments were carried out using 10 OOX per treatment group per replicate experiment.

To further determine if the anti-apoptotic effects of oocytes on CC can be attributed to either BMP-15 and/or BMP-6, an attempt was made to neutralize OSFs using follistatin with and without a BMP-6 NAb. FIG. 8A illustrates that OOX co-cultured with oocytes have a reduced incidence of CC apoptosis compared to OOX alone, which was comparable to the COC control. Either follistatin alone or the BMP-6 NAb alone significantly antagonized ~50% of the anti-apoptotic effects of oocytes on cumulus cells ($P<0.001$). The effects of follistatin and the BMP-6 NAb were not additive as their combined presence did not further restore apoptosis levels.

The results from FIG. 8A suggested that oocyte-secreted BMP-15 and BMP-6 act redundantly to prevent CC apoptosis, and as such, should not act in an additive fashion. An experiment was conducted to test this proposal. Co-culturing OOX with DO or treatment with BMP-15 alone or BMP-6 alone significantly ($P<0.001$) decreased CC apoptosis (FIG. 8B). Combined treatment of OOXs with BMP-6 and BMP-15 did not further decrease apoptosis levels beyond that of BMP-15 alone ($P>0.05$), suggesting no additive effect of these two BMPs.

EXAMPLE 14

Effect of BMP-7 and its Antagonist, Gremlin, on Cumulus Cell Apoptosis

To examine the influence of BMP-7 and its antagonist, gremlin, on CC apoptosis, OOX were treated with 100 ng/ml BMP-7 and/or 10% BMP-15 in the presence or absence of 2 μg/ml gremlin. Three replicates of this experiment were carried out using 10 OOX per treatment group per replicate experiment.

This experiment was conduct to determine the effect of adding BMP-7 and its antagonist, gremlin, in the presence of BMP-15, on the regulation of CC apoptosis. BMP-7 and BMP-15 significantly reduced cumulus cell apoptosis ($P<0.001$: FIG. 9). Apoptosis was not significantly increased when BMP-15-treated OOXs were cultured with an increasing dose of gremlin (FIG. 9A). Conversely, 2 μg/ml gremlin significantly ($P<0.001$) reversed the inhibitory effect of 100 ng/ml BMP-7, but not when BMP-15 was present (FIG. 9B).

EXAMPLE 15

Statistical Analysis

Frequencies of cumulus cell apoptosis were analysed by ANOVA using SigmaStat software (SPSS Inc, Chicago, Ill.), and significant differences between means were determined using Tukey-Kramer post-hoc test for comparison of multiple means. All cell proportional data were arc-sine transformed prior to analysis. Differences were considered statistically significant at $p<0.05$.

Discussion—Study I

The present study demonstrates that removal of the oocyte from the COC by oocytectomy leads to a substantial increase in CC apoptosis. However, low apoptosis levels can be restored by co-culturing OOX with oocytes, which reduces the incidence of apoptosis in a dose dependent manner, and which is completely restored to COC levels at the maximum concentration of 50 DO/well. These findings demonstrate that the low level of CC apoptosis is largely dependent on the presence of the oocyte. Furthermore, the characteristically low incidence of CC apoptosis can be specifically attributed to soluble paracrine signals from the oocyte, rather than oocyte gap junctional signalling to CC, since these effects were observed in a co-culture environment devoid of direct oocyte-CC contact.

The study demonstrates that oocytes actively prevent CC apoptosis by establishing a morphogenic gradient of OSF. Firstly, the reduction in CC apoptosis was assessed by two different methods: TUNEL together with quantitative confocal microscopy. The expression of key proteins regulating apoptosis was also determined by Western blot. Exposure of OOX to oocytes dramatically induced anti-apoptotic Bcl-2 expression. Conversely, pro-apoptotic Bax expression was high in OOX alone and was notably reduced by OSF. These results indicate that oocytes prevent apoptosis within CC by altering the ratio of Bax to Bcl-2 in favour of cell survival. Secondly, the anti-apoptotic actions of oocytes followed a gradient from the site of the oocyte(s). In intact COCs, the incidence of apoptosis was lowest in the inner most layer of CC and increased with increasing distance from the oocyte. Conversely, in OOX+DO, where the oocytes are outside the complex and the OOX is hollow, the outer layer of CC closest to the oocytes had the lowest level of apoptosis. This is the first direct evidence of a very localised morphogenic gradient of OSF in the COC. Thirdly, OSF were able to protect CC from an apoptotic insult. Staurosporine induces apoptosis via a cellular signal cascade (to date uncharacterized) as opposed to causing indiscriminate DNA damage. OSF prevented apoptosis induced by staurosporine demonstrating that oocytes are able to protect CC from an apoptosis-inducing event. Together these results demonstrate that oocytes secrete a potent anti-apoptotic factor(s) that acts in a very localised manner.

Supplementation of media with FSH also decreased the incidence of CC apoptosis in both COCs and OOXs. This is consistent with other studies and with the notion that FSH is an indispensable hormone driving follicular growth and that the primary cause of follicular atresia is inadequate exposure to FSH.

GDF-9 had no significant effect on the incidence of CC apoptosis, despite the fact that GDF-9 is an exceptionally potent GC mitogen. Instead, CC apoptosis was markedly reduced by BMP-15, BMP-6 and BMP-7, which in general are weak mitogens. This study provides multiple lines of evidence that BMP signalling, and not GDF-9 signalling, prevents CC apoptosis; 1) all three BMPs tested reduced the incidence of CC apoptosis in a dose-dependent manner, 2) both BMP-6 and BMP-15 protected CC from apoptosis induced by staurosporine, 3) expression of CC anti-apoptotic Bcl-2 was stimulated by BMP-15 but not by GDF-9, and in contrast, 4) pro-apoptotic Bax expression was inhibited by BMP-15 but not by GDF-9. These findings support the concept that the ratio of Bcl-2 to Bax determines whether a cell lives, or dies and that BMP-15 and BMP-6 can regulate that ratio.

There are two divergent signalling pathways activated by the TGF-β superfamily; the BMP pathway and the TGFβ/activin pathway. GDF-9 signals through the ALK5 receptors, activating SMAD 2/3 molecules and hence eliciting a TGF-β-like intracellular response. On the other hand, BMP-15, BMP-6 and BMP-7 signal through the ALK6 and BMPRII receptors, thereby activating the alternate SMAD 1/5/8 pathway. Hence it appears that bovine OSF stimulate both signalling pathways simultaneously in CC; activation of the SMAD 1/5/8 pathway by BMP-15 and BMP-6 transmitting the anti-apoptotic actions of the oocyte, and activation of the alternate SALAD 2/3 pathway by GDF-9 conveying the oocyte's mitogenic signal.

A further objective of the current study was to attempt to identify the native OSFs preventing CC apoptosis. This is most easily achieved through experimental neutralization of the effects of oocytes on CC, as actual purification of OSFs has so far proved unfeasible. Several high-affinity binding proteins antagonize BMP actions, including follistatin and gremlin. Follistatin, which is highly expressed by GCs in developing follicles, inhibits the biological activities of activins and BMP-15 by forming inactive complexes. In the current study, follistatin and a BMP-6 neutralizing antibody were able to antagonize the anti-apoptotic effects of BMP-15 and BMP-6, respectively. Gremlin, which is expressed in GCs and CC and is a known BMP-2, BMP-4 and BMP-7 antagonist, did not antagonize the anti-apoptotic actions of BMP-15.

We next went on to examine the capacity of the BMP antagonists to neutralise the anti-apoptotic effects of the oocyte. Follistatin or the BMP-6 neutralizing antibody alone were able to partially antagonize the anti-apoptotic actions of the oocyte, suggesting that this action by bovine oocytes can be attributed in part to BMP-5 and/or BMP-6. These findings describe an entirely novel function for these oocyte-secreted molecules. BMP-15 and BMP-6 appear to act redundantly to prevent cumulus cell apoptosis. The recombinant proteins did not have an additive effect on apoptosis when added together, and simultaneous neutralization or native oocyte BMP-15 and BMP-6 did not increase the effect of neutralizing either alone. These data provide the first direct evidence that endogenous BMP-15 and BMP-6 oocyte proteins are important anti-apoptotic OSFs.

In the present study, we show that BMP-7 can mimic the action of oocyte-secreted BMP-15 or BMP-6 in preventing CC apoptosis, even though it is not an OSF and is only expressed by theca in the follicle. Gremlin, which is known to be highly effective at antagonizing BMP-2 and BMP-4 actions, neutralized the anti-apoptotic effect of BMP-7 but was ineffective against BMP-15. As such, the anti-apoptotic actions on CC of the endogenous oocyte-product, BMP-15, were unaffected by the combined presence of BMP-7 and gremlin.

Study II Developmental Competence of Bovine Cumulus-Oocyte Complexes in a Co-Culture System with Denuded Oocytes: Role of Oocyte-Secreted Factor(s)

EXAMPLE 16

Collection of Bovine Oocytes and Culture Conditions

Unless otherwise specified, all chemicals and reagents were purchased from Sigma (St Luis, Mo.).

Bovine ovaries were collected from local abattoirs and transported to the laboratory in warm saline (30-35° C.). Cumulus-oocyte complexes (COC) were aspirated from antral follicles (2 to 8 mm diameter) using an 18-gauge needle and a 10-ml syringe containing ~2 ml aspiration media (Hepes-buffered Tissue Cultured Medium-199; TCM-199, ICN Biochemicals, Irvine, Calif., USA) supplemented with 50 µg/ml kanamycin, 0.5 mM sodium pyruvate, 50 µg/ml heparin and 4 mg/ml fatty acid-free bovine serum albumin (FAF-BSA; ICPbio Ltd, Aukland, NZ). Intact COC with compact cumulus vestments greater than five cell layers and evenly pigmented cytoplasm were selected under a dissecting microscope and washed twice in Hepes-buffered TCM-199 and once in Hepes-TCM199 supplemented with 10% fetal calf serum (FCS) (Invitrogen, Carlsbad, Calif.). Base media for oocyte maturation was Bovine VitroMat (Cook Australia, Eight Mile Plain, Qld, Australia), and is a medium based on the ionic composition of bovine follicular fluid and also containing 100 µm glycylglutamine (Glutamax; Gibco Invitrogen, Carlsbad, Calif., USA), 100 µm N-acetyl-1-cysteine, 100 µm 2-mercaptoethylamine, 1% v/v non-essential amino acids (100×; Gibco Invitrogen), 2% v/v essential amino acids (50×; Gibco Invitrogen), 4 mg mL-1 fatty acid-free BSA and 5.6 mm glucose. All IVM treatments were supplemented with 0.1 IU/ml FSH. (Puregon, Organon, Oss, Netherlands). Complexes were cultured pre-equilibrated 50 ml drops overlaid with mineral oil and incubated at 39° C. with 5% CO2 in humidified air for 24 hour.

EXAMPLE 17

Treatments of Cumulus-Oocyte Complexes
(i) Generation of Denuded Oocytes

Denuded oocytes (DO) were generated by removing CC from COC by vortexing for ~4 minute in 2 ml H-TCM-199/BSA. Any remaining cumulus cells were removed by repeated passage of the oocytes through a fine-bore lire-polished glass pipette in H-TCM-199/BSA.
(ii) Growth Factors Recombinant mouse GDF-9 and recombinant ovine BMP-15 were produced in-house as previously described (Kaivo-Oja et al. (2003) *J. Clin. Endocrinol Metab* 88:755-762; McNatty et al. (2005) *Reproduction* 129:473-480) using transfected 293 human embryonic kidney cell lines (293H). Recombinant proteins were partially purified using hydrophobic interaction chromatography (HIC), as recently described (Hickey et al., (2005) *Biol Reprod* on line), and their concentrations were then estimated by Western blot (Kaivo-Oja et al., 2003 3) *J. Clin. Endocrinol Metab* 88:755-762). Control conditioned medium (293H) was also produced from untransfected 293H cells and purified by HIC.
(iii) In Vitro Fertilization and Embryo Culture.

All experiments were carried out using frozen semen from the same bull of proven fertility. Briefly, one straw of semen stored in liquid nitrogen was rapidly thawed in a water bath for one minute. The semen sample was layered on top of a discontinuous (45%:90%) Percoll gradient (Amersham Bioscience) and centrifuged at room temperature for 20-25 mins at 700 g. The supernatant was removed and the sperm pellet was washed with 500 ml Bovine Vitro Wash (Cook Australia, Eight Mile Plains, Qld, Australia) and centrifuged for a further 5 minutes at 200 g. spermatozoa were resuspended with TVF medium (Bovine Vitro Fert, Cook Australia), then added to the fertilization media drops (Bovine Vitro Fert, Cook Australia, supplemented with 0.01 mM heparin, 0.2 mM penicillamine and 0.1 in M hypotaurine) at a final concentration of $1 \times 10^6$ spermatozoa/ml. COCs were inseminated at a media density of 10 ml of IVF medium per COCs for 24 h, at 39° C. in 6% CO2 in humidified air.

Cumulus cells were removed by gentle pipetting 23-24 h post insemination and five presumptive zygotes were transferred into 20 μl drops of pre-equilibrated Cook Bovine Cleave medium (modified SOFaa, Cook Australia) and cultured under mineral oil at 38.5° C. in 7% O2, 6% CO2, balance N2, for five days (day 1 to day 5).

On Day 5, embryos were transferred in groups of 5-6 to 20 ml drops of pre-equilibrated Bovine Vitro Blast (Cook Bovine Blast medium; Cook Australia) at 38.5° C. overlaid with mineral oil and cultured to Day 8. Embryos were assessed for quality at Day 8 according to the definitions presented in the Manual of the International Embryo Transfer Society and were performed independently and blinded by an experienced bovine embryologist.

EXAMPLE 18

Statistical Analysis

Statistical analysis were carried out by ANOVA using SigmaStat software (SPSS Inc, Chicago, Ill.), and significant differences between means were determined using Tukey-Kramer post-hoc test for comparison of multiple means. All percentage data were arc-sine transformed prior to analysis. Differences were considered statistically significant at $p<0.05$.

EXAMPLE 19

Effect of Co-Culture of intact COCs with DOs during IVM on Subsequent Embryonic Developmental Competence To determine the effect of oocyte-secreted factors in oocyte developmental competence, cumulus-oocyte complexes were randomly allocated into 4 treatment groups during in vitro maturation (IVM). After IVM, all complexes and oocyte were fertilized and the quality of blastocyst formation was assessed on day 8.

Treatment (1) 20 denuded oocytes were cultured in a 200 ml drop for 24 hours (DO; FIG. 1A). Treatment (2) 20 cumulus oocyte complexes were cultured in a 200 ml drop for 24 hours, (COC; FIG. 1B). Treatment (3) 20 COCs were co-cultured from 0 hour with 100 denuded oocytes in a 200 ml drop for 24 hours, of which the 20 complexes (COC-0 h; FIG. 1C) and 20 denuded oocytes (DO-0 h; FIG. 1D) were fertilized after IVM. Treatment 4, 20 COCs were matured in 200 ml IVM medium for the first 9 hours as intact COCs. In parallel, 100 COCs were matured for 9 hours prior to denuding, after which the 100 DOs were transferred to mature with the 20 COCs for the last 15 hour of IVM. As for treatment 3, the 20 complexes (COC-9 h; FIG. 1E) and 20 of the denuded oocytes (DO-9 h; FIG. 1F) were then fertilised as described above. Seven replicate experiments were performed.

Culturing one COC together with 5 DO in a 10 ml drop, gives a concentration of 0.5 DO/ml, which is within the distinctive range used to examine the influence of oocyte-secreted factors.

Figure 11:
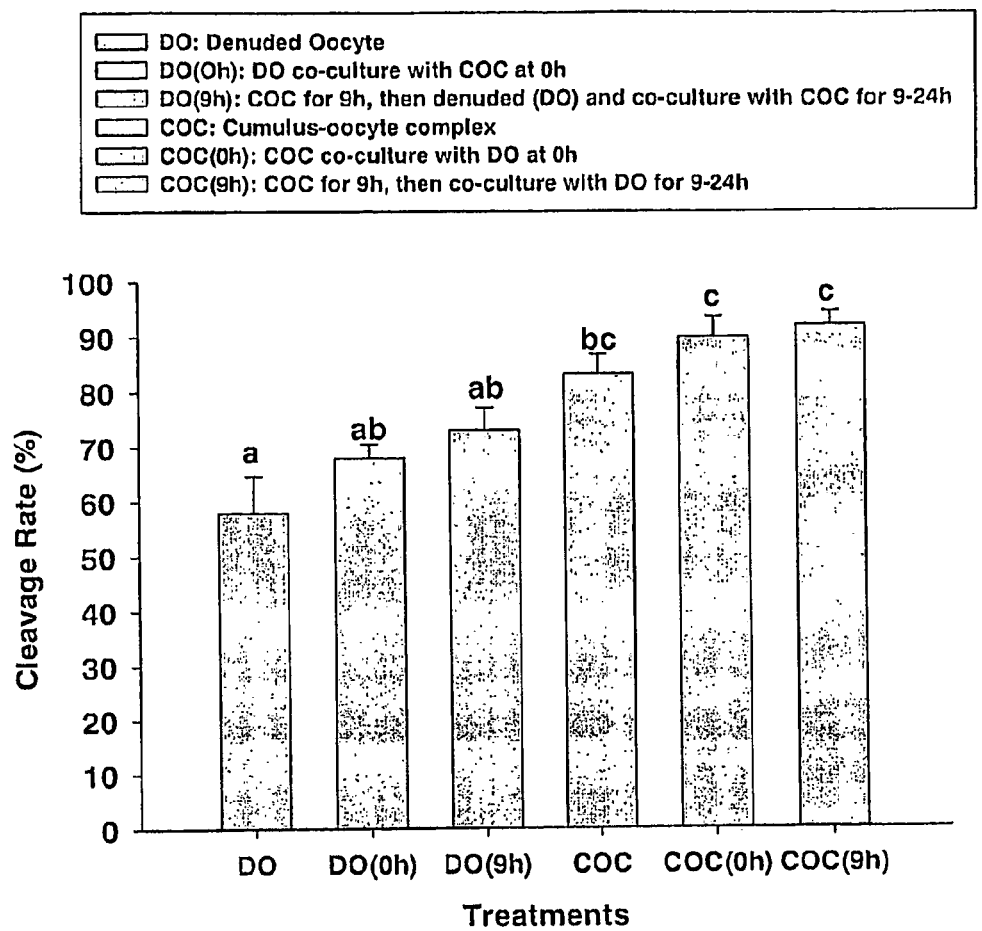
FIG. 11 shows the effect of co-culture of intact cumulus oocyte-complexes with or without denuded oocytes during IVM on the cleavage rate of the subsequent oocyte development. Cumulus-oocyte complexes were randomly allocated into 4 treatment groups during IVM. After IVM, all complexes and oocyte were fertilized and the cleavage rate was assessed on day 2. Bars represent average percentage of cleavage rate (mean±SEM). Values from bars with different labels a, b, c differ significantly ($p<0.001$).
Figure 12:
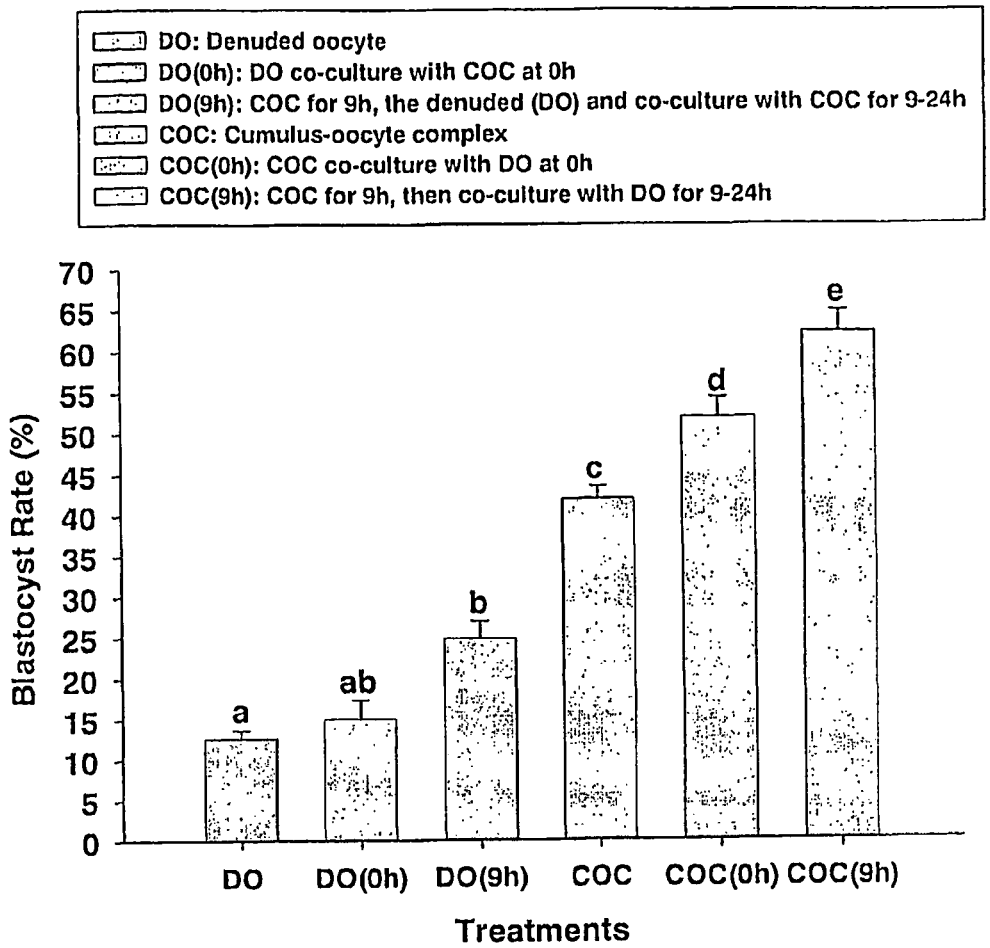
FIG. 12 shows the effect of co-culture of intact COCs with DOs during IVM on the subsequent embryonic developmental competence. Cumulus-oocyte complexes were randomly allocated into 4 treatment groups during in vitro maturation (IVM). After IVM, all complexes and oocyte were fertilized and the quality of blastocyst formation was assessed on day 8. Bars represent average percentage of cleavage rate (mean±SEM). Values from bars with different labels a-e differ significantly ($p<0.001$).

The results are provided in Table 1, and FIGS. 11 and 12.

TABLE 1

Effect of co-culture of intact COCs with DOs during IVM on the subsequent embryonic developmental competence

| Treatments | oocyte (n) | Cleaved (CL) (%) | Blastocyst (BL) BL/CL (%) |
|---|---|---|---|
| DO | 123 | 58.0 ± 6.6 | 12.0 ± 1.1 |
| DO(0 h) | 134 | 68.0 ± 2.4 | 15.0 ± 2.3 |
| DO(9 h) | 127 | 73.0 ± 4.1 | 24.8 ± 2.1 |
| COC | 120 | 83.2 ± 3.5 | 42.0 ± 1.5 |
| COC(0 h) | 125 | 89.8 ± 3.7 | 52.0 ± 2.4 |
| COC(9 h) | 113 | 92.0 ± 2.5 | 62.4 ± 2.5 |

*Values are expressed as mean ± SEM.

As can be seen, co-culturing intact cumulus-oocyte complexes with denuded oocytes at 0 or 9 hour significantly increased ($P<0.001$; FIG. 12) the number of oocyte that reached the blastocyst stage post insemination (50% and 61%, respectively), compared with COC cultured alone (40%; FIG. 12), indicating that paracrine Factors secreted from the denuded oocytes improve the capability of the COC to developed to the blastocyst stage. Furthermore, maturation of oocytes with intact cumulus cells communication during the first 9 hours of IVM prior to denuding, and subsequently cultured with complexes for the last 15 hours of IVM, resulted in significantly more blastocysts on day 8.

The presence of cumulus cells (from neighboring COCs) did not improve the developmental capability of DOs (DO-0 h) whereby blastocyst rates were similar to DOs cultured alone (DO) (FIG. 12). Removal of cumulus cells before IVM significantly ($P<0.001$; FIG. 12) decreased the number of oocytes that reached the blastocyst stage post-insemination, compared with intact COCs (12%, 40% respectively). Maturing oocytes with intact cumulus for the first 9 hours prior to denuding significantly ($P<0.001$; FIG. 12) improved the blastocyst rate compared with DOs cultured alone (12%, 25% respectively).

Cleavage of oocytes was not significantly different between denuded oocyte treatments, nor between cumulus-oocyte complex treatments (FIG. 11), but denuding in general significantly lowered subsequent fertilization rates. However, the incidence of polyspermy (as assessed by separate cohorts of oocytes stained with the DNA fluorescence, H33349) were not difference between denuded oocytes and cumulus-oocyte complexes (data not shown).

EXAMPLE 20

Effect of GDF-9, BMP-15 (Alone and In Combination) on Oocyte Developmental Competence In an attempt to examine which of the oocyte-secreted factors may be contributing to the developmental competence observed in COC. Complexes were cultured for 24 h in the presence or absence of, 10% 293H (control conditioned medium), 10% BMP-15, 175 ng/ml GDF-9, or BMP-15+GDF-9 in combination using the same IVM system previously described. Three replicates of these experiments were performed using 25 COC per treatment group per replicate experiment.

As shown in Table 2, BMP5 alone or in combination with GDF9 was more effective in increasing the number of oocytes that reached the blastocyst stage post insemination compared with COCs treated with GDF-9 alone or COCs matured in the absence of any supplement.

TABLE 2

Effect of GDF-9, BMP-15 (alone and in combination) on oocyte developmental competence

|  | CLEAVAGE RATE | BLACTOCYST RATE | NUMBER OF OOCYTE |
|---|---|---|---|
| CONTROL(COC) | | | |
| $1^{ST}$ REP | 81% | 41% | 21 |
| $2^{nd}$ REP | 96% | 42% | 27 |
| $3^{rd}$ REP | 76% | 41% | 29 |
| $4^{th}$ REP | 84% | 42% | 31 |
| AVERAGE/TOTAL | 84% | 41.5% | 108 |
| GDF-9 | | | |
| $1^{ST}$ REP | 88% | 50% | 25 |
| $2^{nd}$ REP | 92% | 58% | 13 |
| $3^{rd}$ REP | 84% | 35% | 31 |
| $4^{th}$ REP | 83% | 36% | 30 |
| AVERAGE | 87% | 45% | 99 |
| BMP-15 | | | |
| $1^{ST}$ REP | 76% | 58% | 25 |
| $2^{nd}$ REP | 90% | 63% | 21 |
| $3^{rd}$ REP | 80% | 50% | 30 |
| $4^{th}$ REP | 85% | 50% | 33 |
| AVERAGE | 83% | 55% | 109 |
| GDF-9+BMP-15 | | | |
| $1^{ST}$ REP | 100% | 62% | 21 |
| $2^{nd}$ REP | 83% | 63% | 23 |
| $3^{rd}$ REP | 92% | 39% | 25 |
| $4^{th}$ REP | 80% | 40% | 26 |
| AVERAGE | 89% | 51% | 95 |
| 293H | | | |
| $1^{ST}$ REP | 81% | 35% | 21 |
| $2^{nd}$ REP | 86% | 17% | 21 |
| $3^{rd}$ REP | 75% | 28% | 24 |
| $4^{th}$ REP | 92% | 29% | 26 |
| AVERAGE | 84% | 27% | 92 |

EXAMPLE 21

Figure 13:
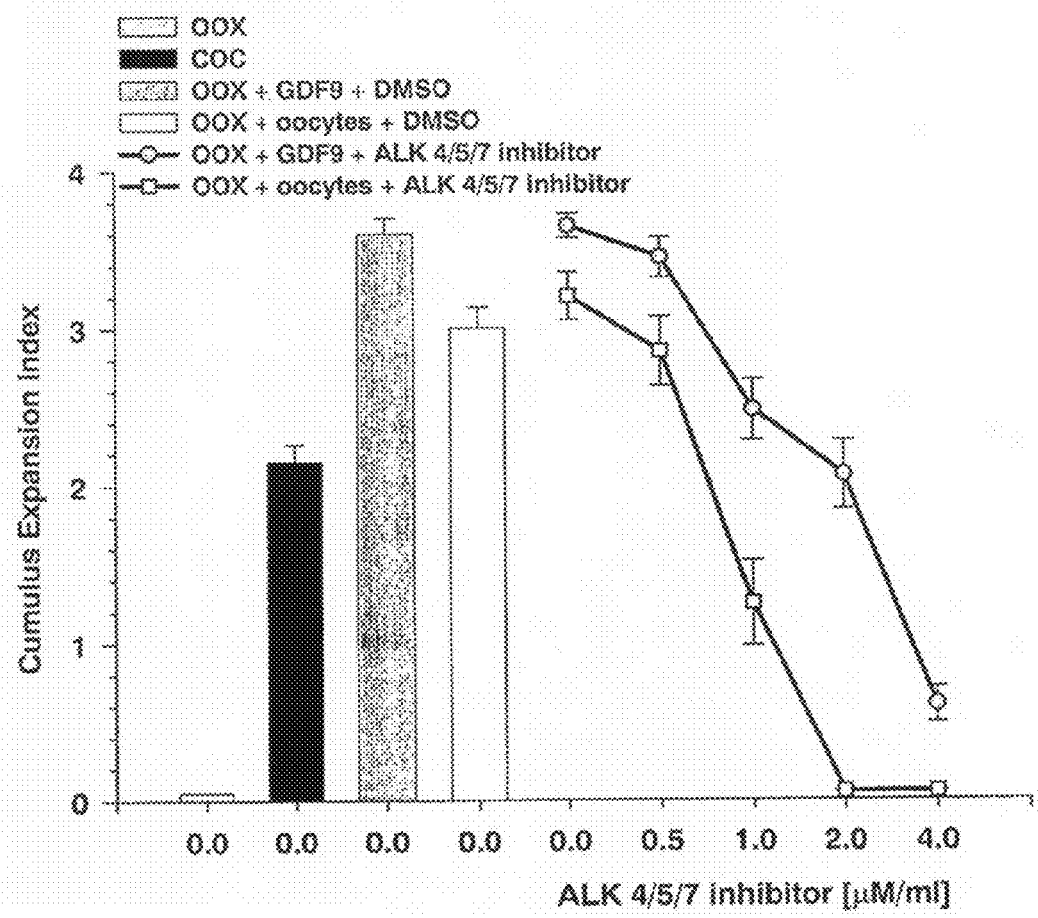
FIG. 13 shows the effect of an AlK4/5/7 inhibitor on GDF-9 and oocyte induced cumulus expansion.

Oocyte Paracrine Signalling to Cumulus Cells by TGF-β Superfamily Molecules is Indispensable for Cumulus Expansion Members of the TGF-β superfamily are prime candidates for the mouse cumulus expansion-enabling factor (CEEF). This study was conducted to examine TGF-β superfamily processes regulating cumulus expansion. COCs were collected from eGG-primed mice and the oocyte microsurgically removed to generate oocytectomised (OOX) complexes. An established scoring system was used to measure FSH-induced cumulus expansion; 0 (no expansion) to +4 (maximum expansion). OOX complexes treated with FSH alone failed to expand (score:0), whereas expansion was significantly ($p<0.05$) induced by either GDF9 (score; mean ±SEM: 3.7±0.1), activin A (2.6±0.1), or co-culture with oocytes (score 3.2±0.2). The type-I receptors for GDF9 and activity are ALK5 and ALK4, respectively. We tested the ability of an ALK4/5/7 kinase inhibitor to neutralize cumulus expansion. The data is shown in FIGS. 13 to 15.

Figure 14A:
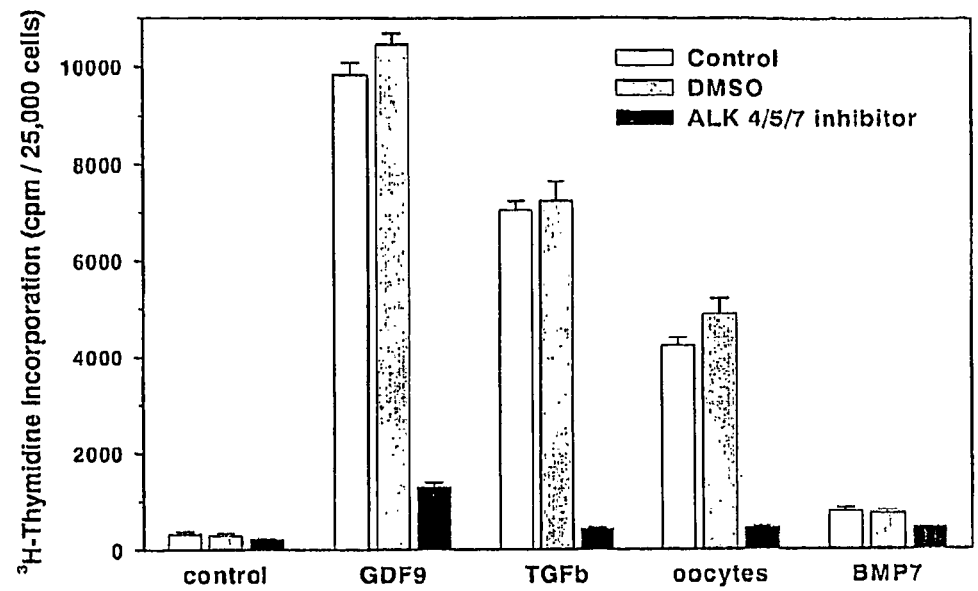
FIGS. 14A and 14B show the effect of an AlK4/5/7 inhibitor on either GDF-9, TGF-β1, or oocyte induced DNA synthesis (Panel A), and the effect of various concentrations of the inhibitor on GDF-9 and oocyte induced DNA synthesis (Panel B).
Figure 14B:
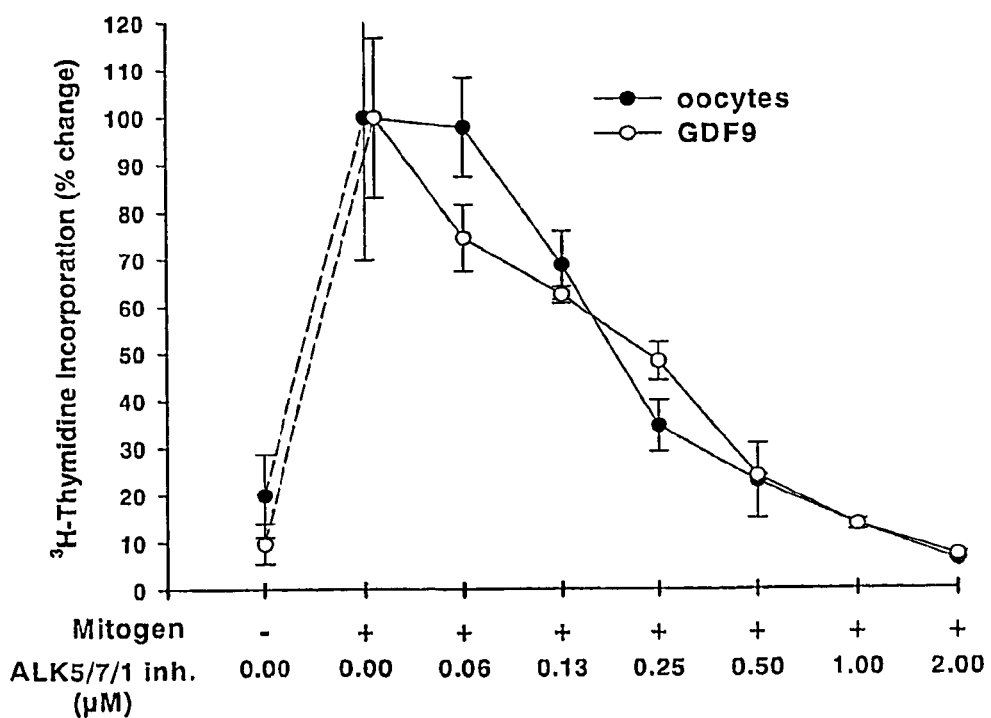

As can be seen, the inhibitor completely neutralised GDF-9 and oocyte-induced cumulus expansion (FIG. 13) and the inhibitor also completely abrogated GDF-9 and oocyte-induced granulosa cell DNA synthesis (FIG. 14).

Figure 15A:
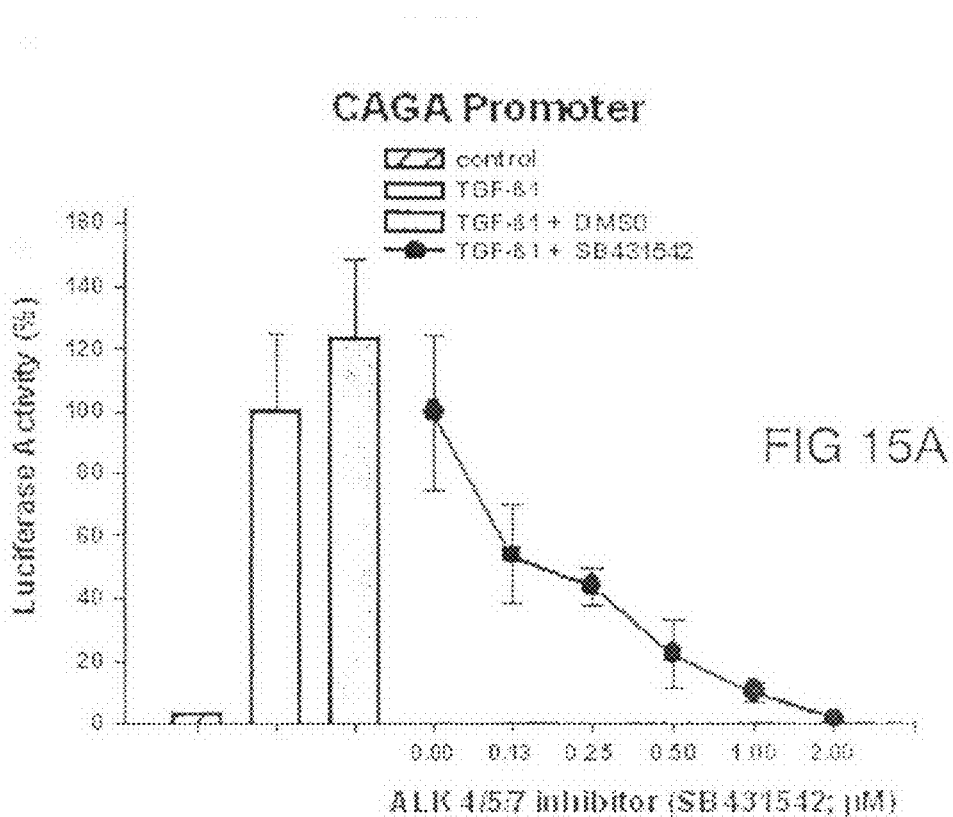
FIGS. 15A and 15B show the effect of various concentrations of the AlK4/5/7 inhibitor on TGF-β1 stimulated CAGA luciferase activity.
Figure 15B:
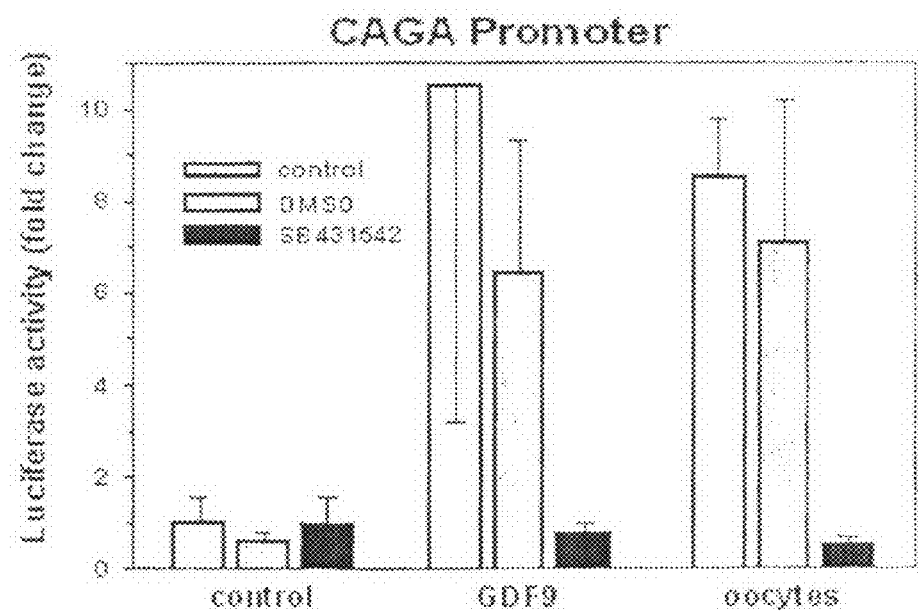

The inhibitor also completely abrogated TGF-β1, GDF9 and oocyte-stimulated activation of Smad2/3 molecules, as evidenced by inhibition of CAGA-luciferase activity (FIGS. 15A and 15B).

Follistatin, an activin antagonist was also effective at neutralising the response of OOX complexes to activin (score: 0), but had no significant effect ($p>0.05$) on the expansion of OOX complexes co-cultured with oocytes (score: 2.7±0.2). This study provides evidence that activin is not the sole CEEF, but signalling through the ALK4/5/7 pathway is indispensable for mouse cumulus expansion.

EXAMPLE 22

Study III —Growth Differentiation Factor 9 Signalling Systems Regulating Marmoset Monkey Granulosa Cell Proliferation Introduction & Aims:

Oocytes regulate follicle growth and development by secreting paracrine growth factors that act on neighbouring granulosa cells (GC). In humans and nonhuman primates, very little is known about the nature of these oocyte-factors or the GC receptor/signalling system(s) they employ, mainly due to the scarcity of oocytes and nonluteinized GC. The aim of this study was to identify the receptor/signalling system utilized by the oocyte-secreted growth differentiation factor 9 (GDF9) to promote GC growth in the common marmoset monkey, *Callithrix jacchus*.

Methods:

(i) Animals

Seven adult female marmosets were used for this study and were housed at The Queen Elizabeth Hospital Animal House. This study was approved by local animal ethics committees and was conducted in accordance with the Guiding Principals for the Care and Use of Research Animals.

Female marmosets were primed with twice daily injections of hFSH (50 IU/day) for 6 days and whole ovaries were removed on day 7 of the follicular phase.

(ii) GC Cultures

Follicles were manually excised and separated into 3 size classes: periantral (PA; 0.42-0.66 mm), small antral (SA; 0.66-1.5 mm) and large antral (LA; >1.5 mm). GCs from each follicle size were collected and pooled, then washed twice in bicarbonate-buffered tissue culture medium-199 (B-TCM) supplemented with 0.3 mg/ml of polyvinyl alcohol (PVA, Sigma). Depending on the individual experiments, mural GCs ($1\times10^5$ cells/ml), hormones, inhibitors and media were added to wells of 96-well plates (Falcon) to give a final volume of 125 µl. Within each experiment, all treatments were carried out in at least duplicate wells and each experiment was replicated on at least 3 occasions. Cells were cultured in an atmosphere of 37° C., 96% humidity in 5% $CO_2$ in air for 18 hours, followed by a further 6 hour pulse of 15.4 kBq tritiated thymidine (3H-thymidine, ICN) under the same conditions. Following culture, mural GCs were harvested, and incorporated $^3$H-thymidine was quantified using a scintillation counter as an indicator of the proportion of cells in S-phase, hence providing an indication of the level of mural GC DNA synthesis and proliferation (30).

(iii) RNA and RT-PCR

Granulosa cells were examined for the expression of ribosomal protein-L19 (L19), bone morphogenetic protein-receptor type 2 (BMPRII), activin receptor like kinase 5 (ALK5) and Smad 3 mRNA by RT-PCR. MGC were collected as described above, 100,000 cells from each follicle size were transferred to Eppendorf tubes on ice, lysed in RLT buffer (Qiagen, Clifton Hill, Australia) and snap frozen in liquid nitrogen before storage at −80° C.

RNA was isolated using a Micro RNA isolation kit (Qiagen, Clifton Hill, Australia). This included the addition of 20 ng of carrier RNA to each sample prior to homogenisation and all samples were DNase treated to eliminate any contaminating genomic DNA.

RNA was quantified using a Ribogreen RNA quantification kit (Molecular Probes, Eugene, Oreg.) according to the manufacturer's protocol.

70 ng of RNA was reverse transcribed using random primers (Boehringer Mannheim, Germany) and a Superscript II RT kit (Life Technologies, Inc.; Grand Island, N.Y.) according to the manufacturer's instructions. A negative RT control substituting water for RNA was included.

PCR amplification utilized reagents supplied in a HotStarTaq DNA polymerase kit (Qiagen, Clifton Hill, Australia). Each reaction consisted of 2.5 µl of Qiagen 10× buffer, 0.4 mM of each dNTP (Applied Biosystems, Australia), 0.5 U of HotStarTaq DNA polymerase, 0.56 µM of each primer, 1 µl of cDNA (diluted 1:4) and made up to a final volume of 25 µl with ultra pure water (Fisher Biotech, Perth, Australia). A negative PCR control, substituting water for cDNA was included in each PCR run. Initial activation of the polymerase at 95° C. for 5 min was followed by 40 amplification cycles of 95° C. for 1 min, 60° C. for 1 min, 72° C. for 1 min and a final extension step of 72° C. for 7 min. Products were then run on a 2% agarose gel for confirmation of a correctly sized products. Finally, the identity of the each PCR product was verified by sequencing.

As marmoset sequence data was lacking, primer pairs were designed against human L19, BMPRII, ALK5 and Smad 3 using Primer Express software (PE Applied Biosystems, Foster City, Calif.), and synthesised by Geneworks (Adelaide, Australia). All primer pairs were designed to bracket an intron. Oligonucleotide sequences of primers used in this study are provided in table 1.

(iv) Luciferase

Luciferase reporter constructs responsive to specific phosphorylated Smads were used to detect the activation of mural GC Smad proteins by recombinant GDF9 Mural GCs were collected and processed as described above, except cells were given a final wash in DMEM(MP Biomedicals, Seven Hills, Australia)+2% FCS (Trace Biosciences, Castle Hill, Australia). Following the final wash, cells were transferred to individual wells of a 96-well plate (Falcon) and cultured at 1.6× $10^5$ cells/ml. After 4 hours of culture, cells were transiently transfected with 50 ng of luciferase reporter construct DNA using Fugene 6 (Roche Diagnostics, Castle Hill, Australia). 18 hours after transfection, medium was aspirated from cells and replaced with DMEM supplemented with 0.1% FCS. Various ligands were added to cells at this point (see below) and the culture period extended for a further 48 hours. Experiments were terminated by removing media from wells and freezing plates at −20° C. To harvest cells, 100 µl of lysis buffer was added to each well and plates were incubated at room temperature on a rocking platform for 20 minutes. 20 µl of cell lysate was used for measurement of luciferase activity using a Galaxystar luminometer (GMB Labtechnologies, Offenburg, Germany).

(v) Stats

Seven adult female marmosets were primed with hFSK for 6 days, whole ovaries were removed on day 7, follicles manually excised, and GC were then collected from 3 size classes: periantral (PA; 0.42-0.66 mm), small antral (SA; 0.66-1.5 mm) and large antral (LA; >1.5 mm). Four different approaches were utilized to examine GDF9 function in GC.

RNA was extracted from oocytes, cumulus cells (CC) and GC and subjected to RT-PCR using human primers, to confine expression of the receptors/intracellular signalling molecules suggested to be involved in GDF9 signal transduction in other species. To examine the GDF9 signalling pathway, cultured GC from LA follicles were transfected with either a CAGA-luciferase or BRE-luciferase reporter construct and treated with various TGF-β superfamily growth factors or co-cultured with mouse oocytes. In order to determine the effects of GDF9 on marmoset GC proliferation, we employed a GC bioassay whereby after 24 h $^3$H-thymidine incorporation is assessed as an indicator of DNA synthesis and cellular proliferation. Cells were treated with various concentrations of GDF9, either alone or with FSH and/or IGF1. In another experiment, GC were treated with an increasing dose of SB431542, an activin-like kinase (ALK) 4/5/7 inhibitor, in the presence of GDF9+/−IGF1.

Results:

EXPERIMENT 1

Expression of GDF9 mRNA by Oocytes

Figure 16A:
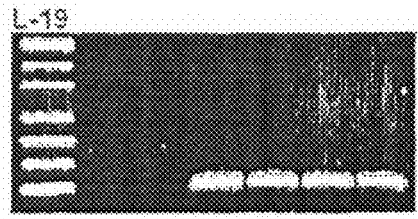
FIGS. 16A and 16B show the expression of GDF9 mRNA by oocytes from different sized follicles. Follicles were manually excised and separated into 3 size classes: periantral, small antral and large antral. Cumulus-oocyte complexes (COC) were collected from each size range and denuded of their cumulus cells (CC). Oocyte RNA was extracted using a Qiagen Micro Rneasy kit. RNA was reverse transcribed using random hexamers and amplified by PCR. –ve RT: no reverse transcriptase; –ve PCR: no DNA polymerase and +ve: positive tissue sample (ovary).
Figure 16B:
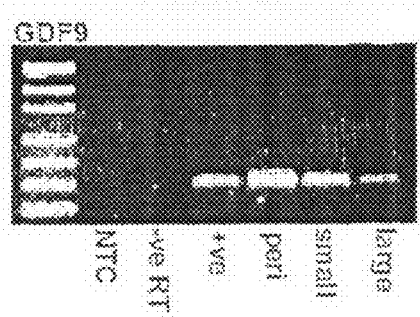
Figure 17A:
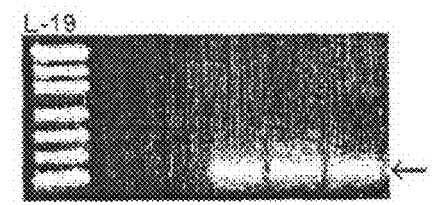
FIGS. 17A to 17D show the expression of receptor/signalling mRNA by granulosa cells (GC) from different sized follicles. $1 \times 10^5$ GCs from each follicle size was collected and total RNA extracted. GC RNA was reverse transcribed using random hexamers and amplified by PCR. –ve RT: no reverse transcriptase; –ve PCR: no DNA polymerase and +ve: positive tissue sample (ovary).
Figure 17B:
Figure 17C:
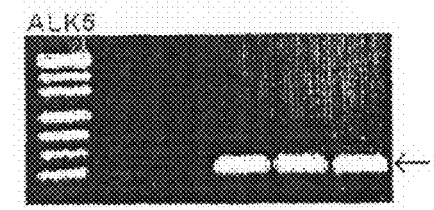
Figure 17D:
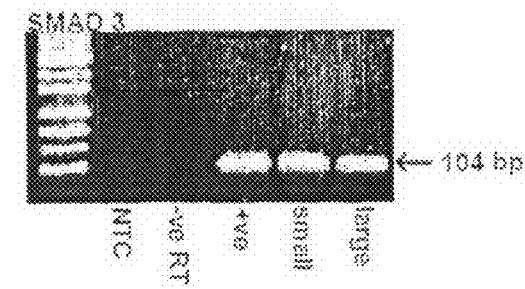

RT-PCR was carried out on cDNA derived from denuded oocytes retrieved from either peri, small or large antral follicles. As expected oocytes from all size classes expressed GDF9 mRNA (FIG. 16). The identity of the PCR product was confirmed by sequencing.

EXPERIMENT 2

Expression of GDF9 Signalling Pathway Molecules by GC

This experiment was conducted to determine whether GC from small and large antral follicles express mRNA for the key GDF9 signalling pathway molecules; bone morphogenetic protein receptor II, ALK5 and Smad 3. mRNA expression for all 3 transcripts were detected in GC form both small and large antral follicles (FIG. 17). All PCR products were sequenced and showed homology to their corresponding human sequences.

EXPERIMENT 3

Activation of the Smad Intracellular Signalling Pathway

Figure 18A:
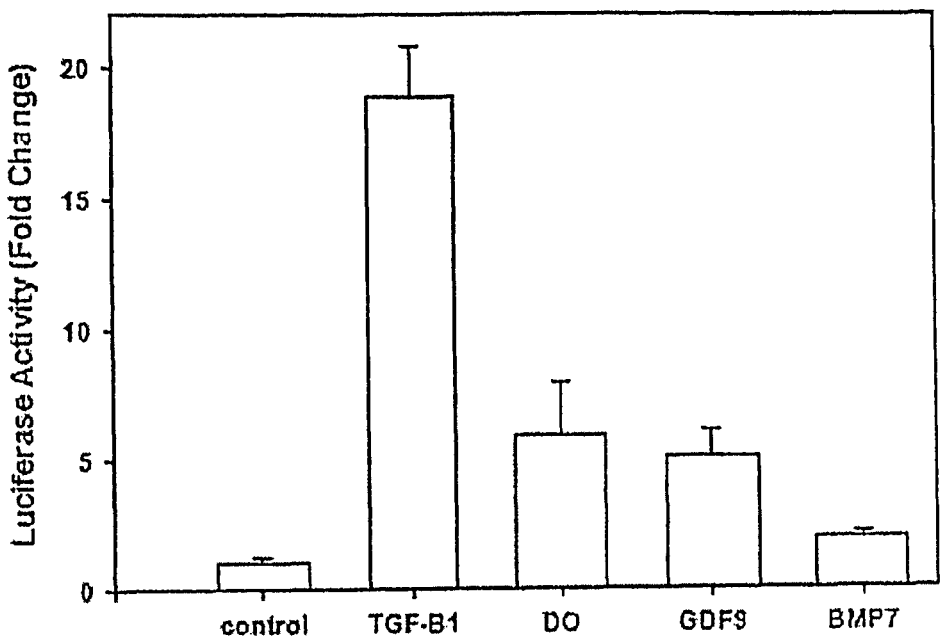
FIGS. 18A and 18B show the activation of the TGF-β signalling pathway by GDF9 and oocytes. MGC from large follicles were transiently transfected with either a Smad 3-responsive CAGA-luciferase reporter construct (A) or a Smad 1-responsive BRE-luciferase reporter construct (B). Cells were subsequently left untreated, treated with 0.5 ng/ml TGFβ1, 88-265 ng/ml GDF9, 50 ng/ml BMP7 or co-cultured with 60 mouse oocytes. Cells were cultured for 48 h after which time luciferase activity was measured from cell extracts. Bars represent means+/– SEM from 3 replicate experiments expressed as a fold change relative to control.

This is experiment was conducted to determine whether GC from large antral follicles were capable of responding to TGF-β and/or BMP signals. Cells were transfected with either a CAGA or BRE luciferase plasmid construct and then treated with TGF-β1, GDF9, BMP7 or oocytes. CAGA-luciferase activity was stimulated by TGF-β1, oocytes and GDF9, 19 fold, 6 fold and 5 fold above control levels respectively, but was not stimulated by BMP7 (FIG. 18A). Conversely, BRE-luciferase activity was stimulated 31 fold by BMP7, compared to control levels, but was not activated by TGF-β1, GDF9 or oocytes (FIG. 19B).

EXPERIMENT 4

Figure 18B:
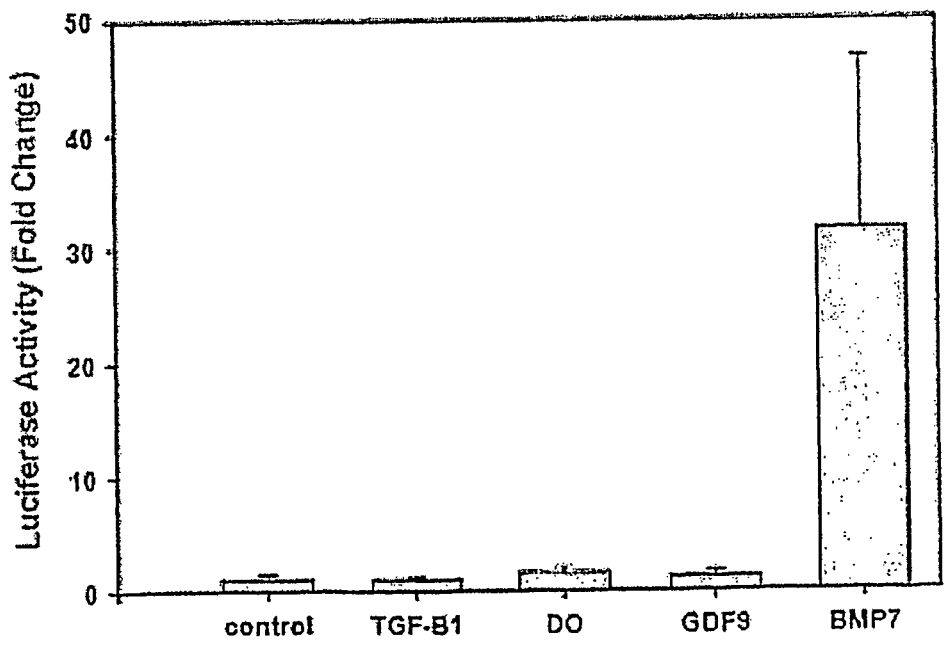

GDF9 Stimulates Granulosa Cell Proliferation Via the TGF-β/Activin Signalling Pathway We next exploited an ALK 4/5/7 kinase inhibitor to provide another line of evidence that GDF9 promotes GC proliferation via the TGF-β/activin signalling pathway. The inhibitor, SB431542, specifically antagonizes the kinase activity of ALK4, ALK5 and ALK7, without affecting the activity of ALK6 (Inman 2002). We have previously shown that SB431542 dose-dependently inhibits TGF-β1, GDF9 and oocyte-stimulated mural GC growth in the mouse. In this study, using marmoset GC from large antral follicles we have also shown that DNA synthesis, stimulated by GDF9, is dose-dependently inhibited in the presence of SB431542 (FIG. 18). At a concentration of 1 μM the kinase inhibitor can completely eliminate the stimulatory effects of GDF9.

EXPERIMENT 5

Mural Granulosa Cells from Peri Antral Follicles have a Higher Mitogenic Index

Figure 19:
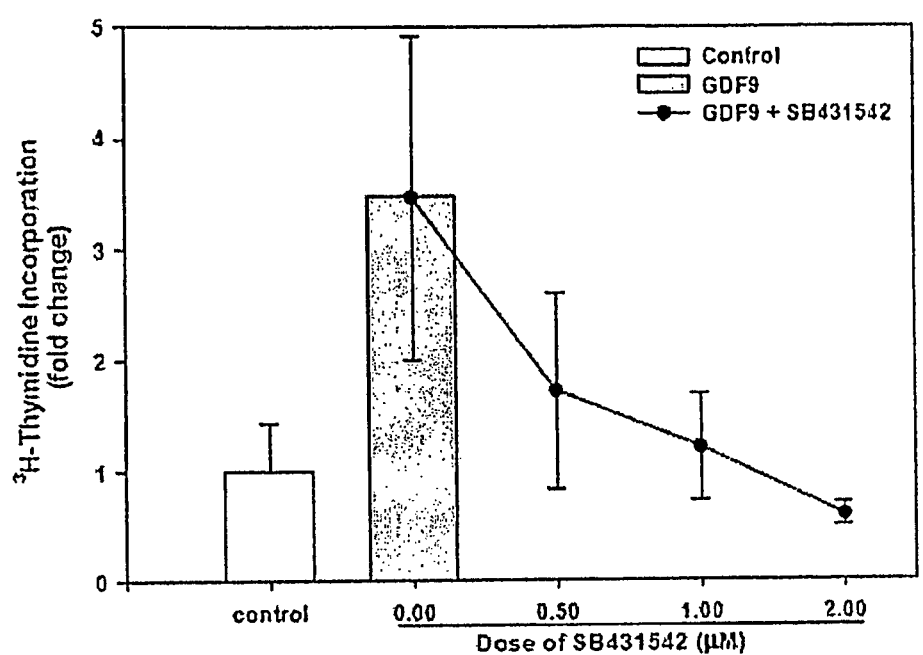
FIG. 19 shows the inhibition of GDF9-stimulated mural granulosa cell DNA synthesis using the AlK4/5/7 kinase inhibitor, SB431542. Mural GC from large antral follicles were cultured for 24h and thymidine incorporation was stimulated with 175 ng/ml GDF9. The AlK4/5/7 kinase inhibitor, SB-431542 dose dependently inhibited thymidine incorporation stimulated by GDF9. Bars/points represent means+/–SEM from 3 replicate experiments expressed as a fold change relative to control.

In this experiment we looked at the capacity of mural granulosa cells from different sized follicles to respond to the growth promoting activity of GDF9. In general, DNA synthesis was lowest (399 cpm/12,500 cells) in GC from large follicles and highest (5936 cpm/12,500 cells) in GC from peri-antral follicles (FIG. 19).

Figure 20:
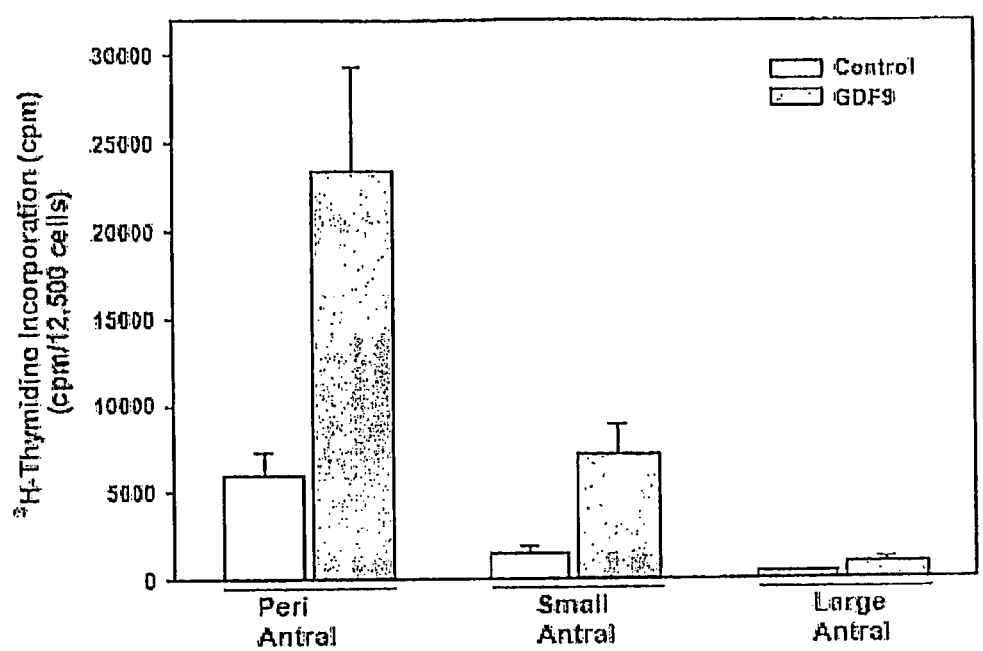
FIG. 20 shows the effect of GDF9 and follicle size on mural granulosa cell DNA synthesis. Mural GC from peri antral, small antral and large antral follicles were cultured for 24h in the presence of 175 ng/ml of GDF9. At the end of the culture period 3H-thymidine incorporation was assessed. Bars represent mean cpm/12,500 cells+/– SEM from 8 replicate experiments.

Effect of GDF9 and Follicle Size on Mural Granulosa Cell DNA Synthesis:

FIG. 20 shows mural GC from small and large antral follicles were treated with an increasing dose of GDF9(0-350 ng/ml) for 24 h. At the end of the culture period $^3$H-thymidine incorporation was measured. Points represent mean cpm/12,500 cells+/−SEM from 7 replicate experiments.

Figure 21:
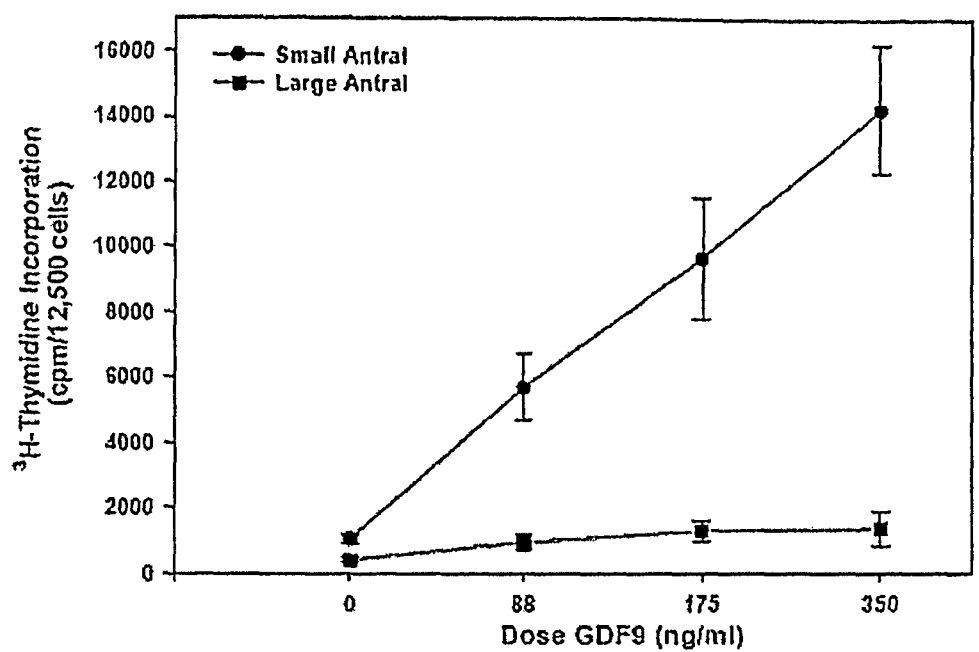
FIG. 21 shows the effect of GDF9 and follicle size on mural granulosa cell DNA synthesis. Mural GC from small and large antral follicles were treated with an increasing dose of GDF9 (0-350 ng/ml) for 24h. At the end of the culture period 3H-thymidine incorporation was measured. Points represent mean cpm/12,500 cells+/–SEM from 7replicate experiments.

Effect of GDF9 in Combination with FSH and/or IGF1 on Mural Granulosa Cell DNA Synthesis:

FIG. 21 shows the effect of GDF9 in combination with FSH and/or IGF-1 oil mural granulosa cell DNA synthesis. Mural GC from small (A) or large (B) antral follicles were cultured for 24 h with combinations of GDF9 (175 ng/ml), rhFSH (50 mIU/ml) and IGF-1 (25 ng/ml). Bars represent mean cpm/12,500 cells+/−SEM from 7 replicate experiments.

Figure 22A:
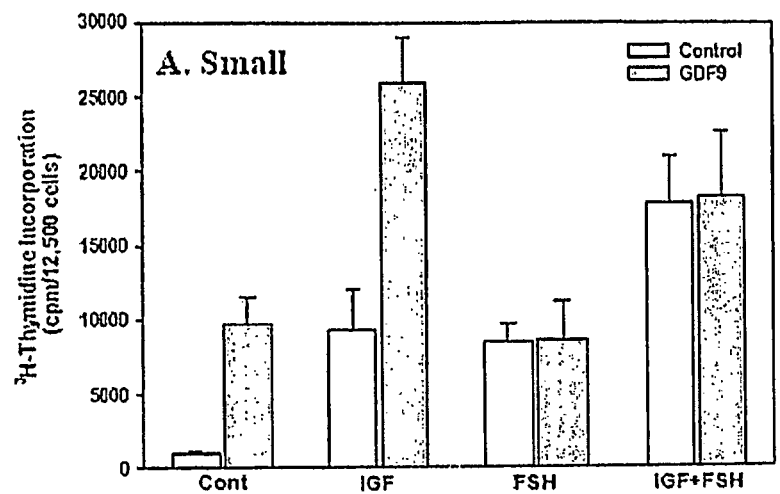
FIGS. 22A and 22B show the effect of GDF9 in combination with FSH and/or IGF-1 on mural granulosa cell DNA synthesis. Mural GC from small (A) or large (B) antral follicles were cultured for 24h with combinations of GDF9 (175 ng/ml), rhFSH (50 mIU/ml) and IGF-I (25 ng/ml). Bars represent mean cpm/12,500 cells+/– SEM from 7 replicate experiments.
Figure 22B:
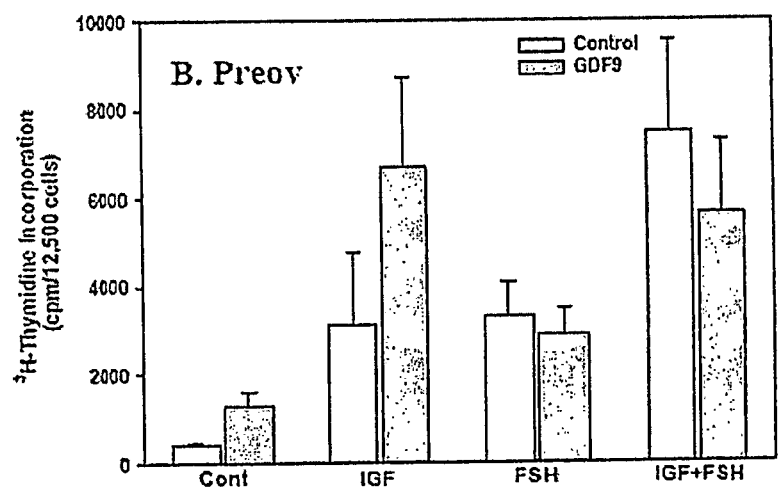
Figure 23A:
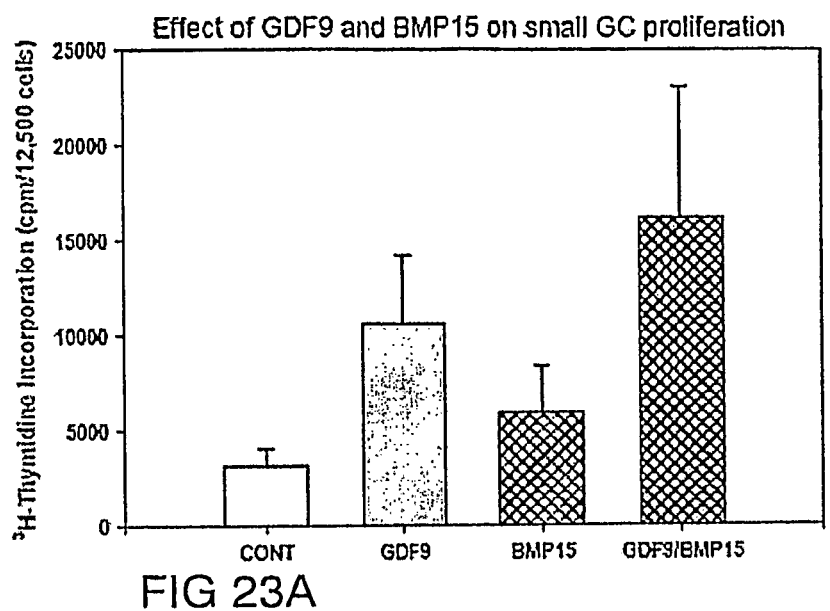
FIGS. 23A and 23B show the effect of GDF9+/– BMP 15 on mural granulosa cell DNA synthesis. Mural GC from small (A) or large (B) antral follicles were cultured with either GDF9 (175 ng/ml) or BMP 15 (10%) alone or a combination of the two. Bars represent means+/– SE of three replicate experiments.
Figure 23B:
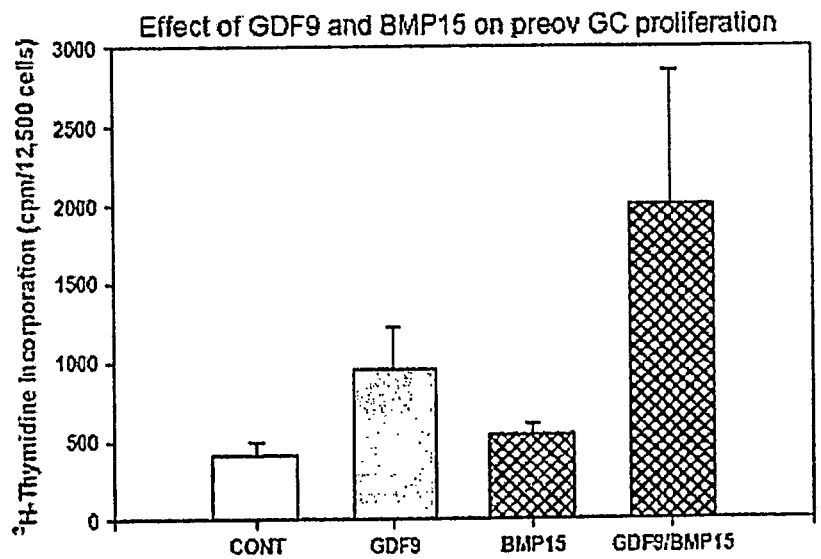

Effect of GDF9+/−BMP 15 on Mural Granulosa Cell DNA Synthesis:

FIG. 22 shows the effect of GDF9+/−BMP15 on mural granulosa cell DNA synthesis. Mural GC from small (A) or large (B) antral follicles were cultured with either GDF9 (175 ng/ml) or BMP15 (10%) alone or a combination of the 2. Bars represent means+/−SE of three replicate experiments.

Conclusions

This study characterizes the molecular basis by which the oocyte-secreted factor GDF9 stimulates primate granulosa cell proliferation. From early to late follicle development, marmoset CC and GC possess the molecular components required to respond to GDF9. Indeed, GDF9 stimulates GC DNA synthesis in all follicle sizes, but most notably in small follicles, in particular in synergism with IGF1. Marmoset GC become refractory to GDF9 as they differentiate prior to ovulation. GDF9 modulates marmoset GC proliferation by utilizing components of the TGF-β signalling system and inducing a TGF-β-like intracellular response.

EXAMPLE 23

Study IV —Oocyte-Secreted Factors Enhance Oocyte Developmental Competence

Materials and Methods:
Collection of Oocytes and Culture Conditions

Unless otherwise specified, all chemicals and reagents were purchased from Sigma (St Louis, Mo.). Bovine ovaries were collected from local abattoirs and transported to the laboratory in warm saline (30-35° C.). COCs were aspirated from antral follicles (3 to 5 mm diameter) using an 18-gauge needle and a 10-ml syringe containing ~2 ml aspiration medium (Hepes-buffered. Tissue Cultured Medium-199; TCM-199. ICN Biochemicals, Irvine, Calif., USA) supplemented with 50 μg/ml kanamycin, 0.5 mM sodium pyruvate, 50 μg/ml heparin and 4 mg/ml fatty acid-free bovine serum albumin (FAF-BSA; ICPbio Ltd, Aukland, NZ). Intact COCs with compact cumulus vestments>~5 cell layers and evenly pigmented cytoplasm were selected under a dissecting microscope and washed twice in Hepes-buffered TCM-199 and once in Hepes-buffered TCM-199 supplemented with 10% fetal calf serim (FCS) (Invitrogen, Carlsbad, Calif.). The basic medium for oocyte maturation was Bovine VitroMat (Cook Australia, Eight Mile Plains, Qld, Australia), a medium based on the ionic composition of bovine follicular fluid. All IVM treatments were supplemented with 0.1 IU/ml FSH (Puregon, Organon, Oss, Netherlands). Complexes were cultured in pre-equilibrated 300 Π l drops overlaid with mineral oil and incubated at 39° C. with 5% CO2 in humidified air for 24 hour.

Generation of Denuded Oocytes

Denuded oocytes (DO) were generated by removing CCs from COCs by vortexing for ~4 minutes in 2 ml Hepes-buffered TCM-199. Any remaining CCs were removed by repeated passage of the oocytes through a fine-bore fire-polished glass pipette in Hepes-buffered TCM-199.

Growth Factors & Antagonists

Recombinant mouse GDF9 and recombinant ovine BMP15 were produced and partially purified in-house as previously described using transfected 293 human embryonic kidney cell lines (293H) originally donated by O. Ritvos (University of Helsinki). Control conditioned medium (hereafter designated '293H') was produced from untransfected 293H cells and subjected to the same chromatography procedures as GDF9 and BMP15 conditioned media.

SB-431542, generously donated by GlaxoSmithKline (Stevenage, UK), acts as competitive ATP binding site kinase inhibitor, specifically antagonizing the activities of activin receptor-like kinases (ALKs) 4, 5 and 7, without effecting the activities of ALKs 1, 2, 3 or 6 or other cellular kinases. Consequently, SB-431542 potently antagonizes the ALK 4/5 ligands; TGF-β1, the activins and GDF9, without affecting BMP signalling (Inman et al., 2002; Gilchrist et al., 2006). We have recently demonstrated that SB-431542 completely antagonizes the growth-promoting actions of native OSFs and GDF9 on granulosa cells. Follistatin-288 was generously donated by S. Shimasaki (University of California San Diego, USA) and we have previously shown that this binding protein antagonizes the bioactivities of native OSFs and recombinant BMP15 in CCs.

In Vitro Fertilization and Embryo Culture.

In vitro production of embryos was undertaken using defined, serum-free media (Bovine Vitro series of media, Cook Australia). Frozen semen from a single bull of proven fertility was used in all experiments. Briefly, thawed semen was layered over a discontinuous (45%: 90%) Percoll gradient (Amersham Bioscience) and centrifuged (RT) for 20-25 mins at 700 g. The supernatant was removed and the sperm pellet was washed with 500 μl Bovine VitroWash (Cook Australia) and centrifuged for a further 5 minutes at 200 g. Spermatozoa were resuspended with IVF medium (Bovine Vitro-Fert, Cook Australia), then added to the fertilization media drops (Bovine VitroFert, supplemented with 0.01 mM heparin, 0.2 mM penicillamine and 0.1 mM hypotaurine) at a final concentration of 1×106 spermatozoa/ml. COCs were inseminated at a density of 10 μl of IVF medium per COC for 24 h, at 39° C. in 6% CO2 in humidified air.

CCs were removed by gentle pipetting 23-24 h post insemination and five presumptive zygotes were transferred into 20 μl drops of pre-equilibrated Cook Bovine VitroCleave medium (Cook Australia) and cultured under mineral oil at 38.5° C. in 7% O2, 6% CO2, balance N2, for five days (day 1 to day 5).

On Day 5, embryos were transferred in groups of 5-6 to 20 μl drops of pre-equilibrated Bovine VitroBlast (Cook Australia) at 38.5° C. overlaid with mineral oil and cultured to Day 8. Embryos were assessed for quality at Day 8 according to the definitions presented in the Manual of the International Embryo Transfer Society (Stringfellow, 1998) and were performed independently and blinded by an experienced bovine embryologist.

Differential Staining

Cell counts were performed using a modified version of the technique described by (Fouladi-Nashta et al., 2005). Briefly, expanded/hatched blastocysts were placed into acid Tyrode's solution to remove the zona, followed by a brief wash in 4 mg mL-1 poly-vinyl alcohol (PVA) in phosphate-buffered saline (PBS/PVA). Zona-free embryos were then incubated in 10 mM trinitrobenzene sulfonic acid (TNBS) in PBS/PVA at 4° C. for 10 ml. Following this, embryos were subsequently incubated with 0.1 mg mL-1 anti-dinitrophenol-BSA antibody (Molecular Probes, Eugene, Oreg., USA) at 37° C. for 10 min. Following complement-mediated lysis using guinea-pig complement, embryos were washed and incubated in 10 μg mL-1 propidium iodide for 20 min at 37° C. (to stain the trophectoderm), followed by 4 μg mL-1 bisbenzimide (Hoechst 33342; Sigma-Aldrich) in 100% ethanol at 4° C. overnight (to stain both the inner cell mass (ICM) and trophectoderm). Embryos were then whole mounted in a drop of 80% glycerol in PBS on microscope slides and coverslips were sealed with nail polish. Embryos were then examined under a fluorescence microscope (Olympus, Tokyo, Japan) at 400× equipped with an ultraviolet filter and a digital camera attached to determine total and compartment cell counts where inner cell mass (ICM) nuclei appeared blue and trophectoderm (TE) nuclei stained pink.

EXPERIMENT 1

Figure 24:
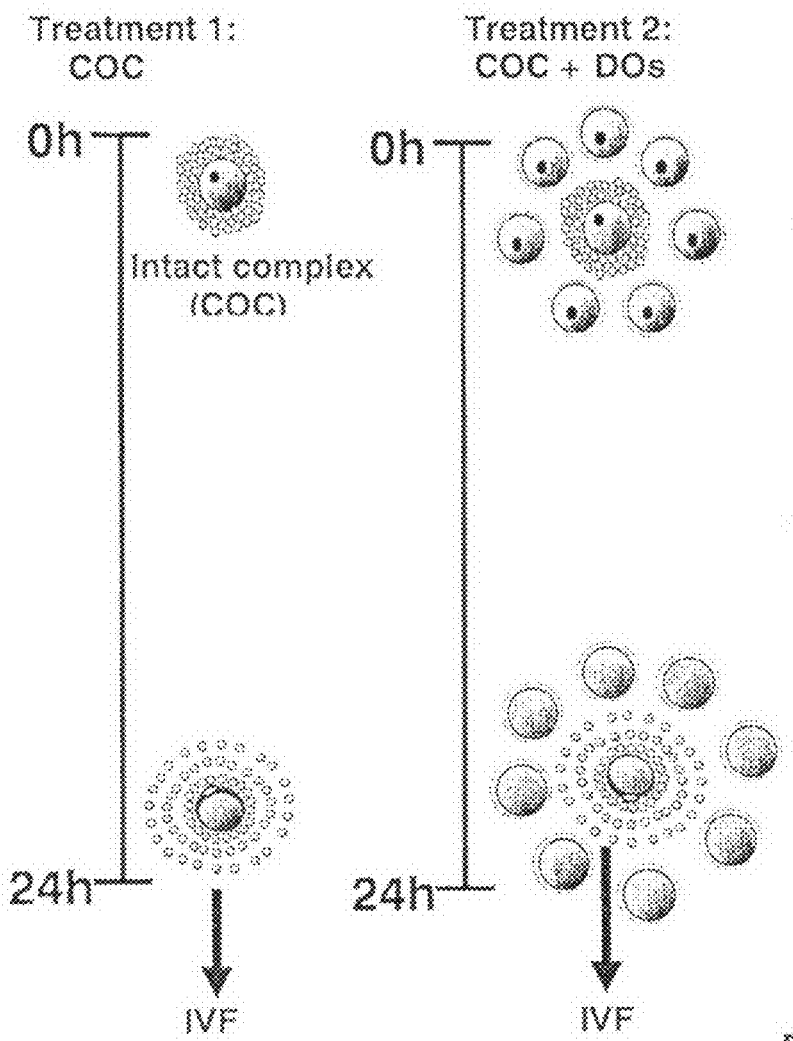
FIG. 24 shows a diagrammatic illustration of the experimental design to expose COCs to oocyte-secreted factors (OSFs) during IVM. COCs were cultured either alone or co-cultured with denuded oocytes (COC+DOs) at a concentration of 0.5 DO/μl for the duration of IVM. Oocytes were subsequently fertilized and embryo development was used to assess oocyte developmental competence.

Effect of Co-Culture of Intact COCs with DOs During IVM on Subsequent Developmental Competence To determine the effect of native OSFs on oocyte developmental competence, COCs were randomly allocated into 2 treatment groups during IVM; treatment (1), 30 COCs were cultured in a 300 μl drop for 24 hours, treatment (2), 30 COCs were co-cultured from 0 to 24 hours with 150 DOs in a 300 μl drop, after which the 30 complexes were removed and fertilized (FIG. 24). Treatment 2 yields a ratio of 1 COC to 5 DOs in a 10 μl drop, giving a concentration of 0.5 DO/μl which is within the range required to examine the influence of OSFs.

After IVM, all complexes were fertilized and the number and quality of blastocyst formation was assessed on day 8. Six replicate experiments were performed.

EXPERIMENT 2

Effect of BMP15 and/or GDF9 During IVM on Oocyte Developmental Competence

This experiment was conducted to determine if addition of exogenous recombinant OSFs, GDF9 and/or BMP15, during IVM improves subsequent oocyte developmental competence. COCs were cultured for 24 h in the base IVM medium described above, with the following additional treatments 1) none (control), 2) 175 ng/ml GDF9, 3) 10% v/v BMP15, 4) 10% v/v BMP15 and 175 ng/ml GDF-9, and 5) 10% v/v 293H. After IVM, all complexes were fertilized and blastocyst formation was assessed on day 8. Four replicates of these experiments were performed using 50 COCs per treatment group per replicate experiment.

Experiments 3 & 4

Effect of GDF9 or BMP15 Antagonists on Oocyte Developmental Competence

The aim of this experiment was two-fold; (1) to examine the effect of inhibiting the GDF9 or BMP15 secreted by the oocyte within an intact COC on subsequent development, and (2) to specifically neutralize the effects of the recombinant OSFs on COCs, as these preparations are not pure. COCs were either cultured alone, with 175 ng/ml GDF9 or 10% v/v 293H, either in the presence or absence of 4 μM SB-431542 (GDF9 antagonist). In a separate experiment, COCs were cultured alone, or with 10% v/v BMP15 or 10% v/v 293H, either in the presence or absence of 10 μg/ml of follistatin-288 during IVM. After IVM, all complexes were fertilized and blastocyst formation was assessed on day 8. Three replicates of these experiments were performed using 60 COC per treatment group per replicate experiment.

Statistical Analyses

All replicated proportional development data were arc-sine transformed prior to analysis. Statistical analyses were carried out by ANOVA using SigmaStat software (SPSS Inc, Chicago, Ill.), and significant differences between means were determined using Tukey-Kramer post-hoc test for comparison of multiple means. Differences were considered statistically significant at p<0.05.

Results:

EXPERIMENT 1

Effect of Co-Culture of Intact COCs with DOs During IVM on Subsequent Developmental Competence Exposure of intact COCs to native OSFs from DOs significantly increased (P<0.001) the proportion of oocytes that reached the blastocyst stage post-insemination (51%), compared with COCs cultured alone (39%). Furthermore, the cell numbers of the ensuing blastocysts was significantly (P<0.05) increased, with more total and trophectoderm cell numbers, compared to control COCs. However, cleavage of oocytes was not significantly affected by exposure to OSFs during IVM. (P>0.05).

EXPERIMENT 2

Effect of BMP15 and/or GDF9 During IVM on Oocyte Developmental Competence

Addition of BMP15 to maturing COCs dramatically enhanced (P<0.05) their development to the blastocyst stage, by 16% compared to control COCs or 30% compared to 293H-treated COCs. Conditioned medium from the parent 293H cell line adversely affected oocyte developmental potential, lowering blastocyst rates by 14% compared to control COCs (P<0.001). GDF9 also increased (P<0.05) blastocyst yield compared to 293H-treated COCs, but not compared to COCs cultured alone. There was no additive effect on blastocyst yield of GDF9 above that of BMP15 alone. Cleavage of oocytes was not significantly affected by the treatment groups, although rates were notably lower in those exposed to the 293H control conditioned medium.

Experiments 3 & 4

Effect of GDF9 or BMP15 Antagonists on Oocyte Developmental Competence

Figure 25A:
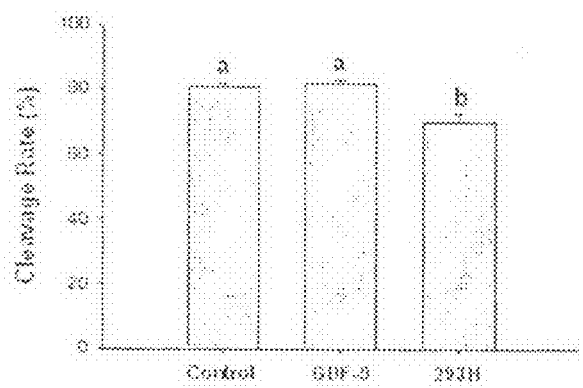
FIGS. 25A and 25B show the effect of treatment of intact COCs with GDF9 in the presence or absence of the GDF9 antagonist, SB-431542, during IVM on subsequent cleavage (A) and developmental competence (B). Following IVM, all complexes were fertilized and the cleavage rate was assessed on day 2 and blastocyst formation on day 8. 293H is control-conditioned medium from untransfected 293H cells. Bars represent percentages (mean±SEM) and bars or grouped bars within a graph with different labels a-d differ significantly ($p<0.05$). Cleavage rate was not affected by SB-431542 but was by 293H.
Figure 26A:
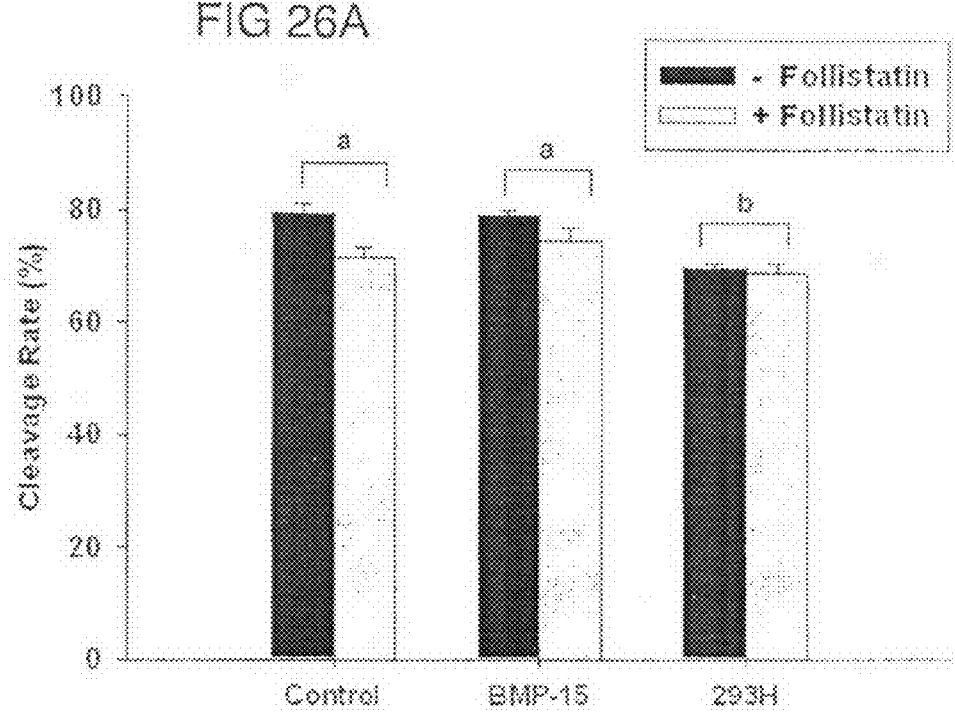
FIGS. 26A and 26B show the effect of treatment of intact COCs with BMP 15 in the presence or absence of follistatin during IVM on subsequent cleavage (A) and developmental competence (B). After IVM, all complexes were fertilized, cleavage rate was assessed on day 2 and blastocyst formation on day 8. 2931-1 is control-conditioned medium from untransfected 293H cells. Bars represent percentages (mean±SEM) and bars or grouped bars within a graph with different labels a-d differ significantly ($p<0.05$). Cleavage rate was adversely affected by follistatin and by 293H.

The adverse effect of adding 293H during IVM on cleavage rate observed in the previous experiment 2 was also observed in both of these experiments; the difference from control groups was now significant (2-way ANOVA, p<0.05; FIGS. 25A and 26A). The GDF9 antagonist, SB-431542, which is an ALK 4/5/7 inhibitor, had no influence of the cleavage rate of the oocyte (p>0.05; FIG. 25A). In contrast, treatment of COCs with follistatin, regardless of BMP15 treatment, significantly decreased cleavage rate of oocytes (follistatin, 71.8±1.3; control, 76.2±1.3; p=0.007; FIG. 26A). Consistent with experiment 2, treatment of COCs with GDF9 did not significantly alter cleavage rates compared to the control, nor did treatment with BMP15, independent of any effects of follistatin (FIGS. 25A and 26A).

Figure 2B:
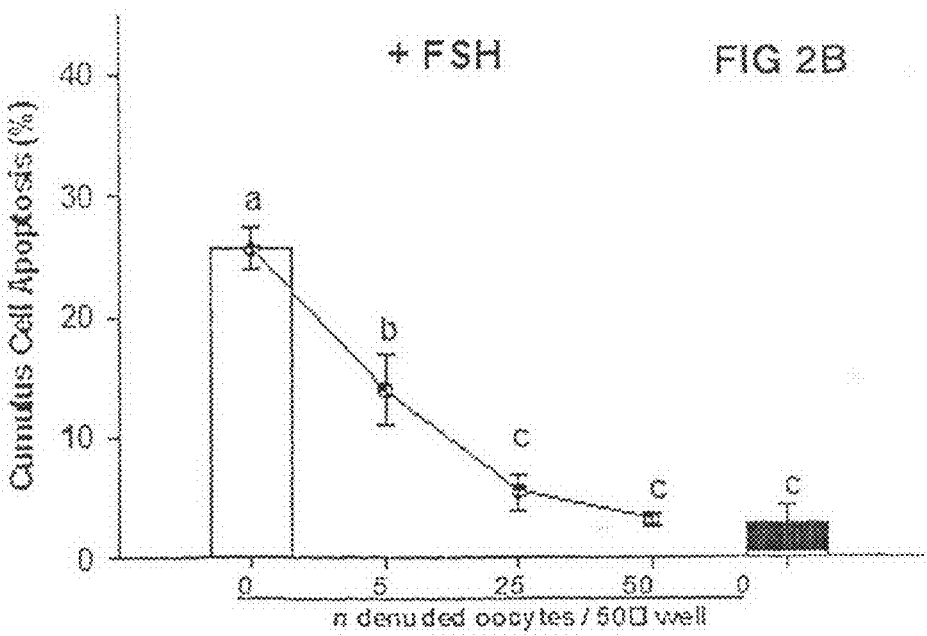
Figure 25B:
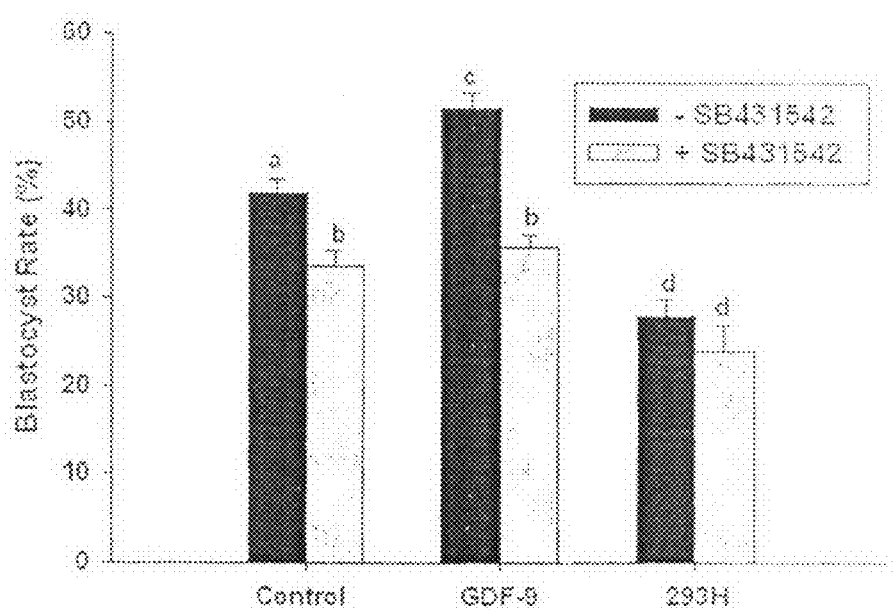
Figure 26B:
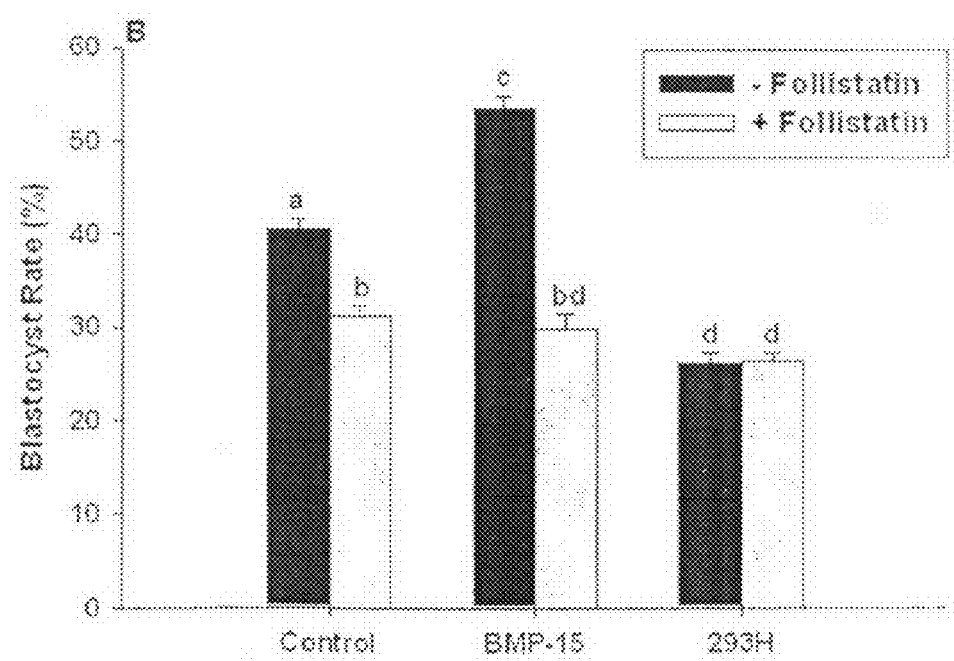
Figure 27:
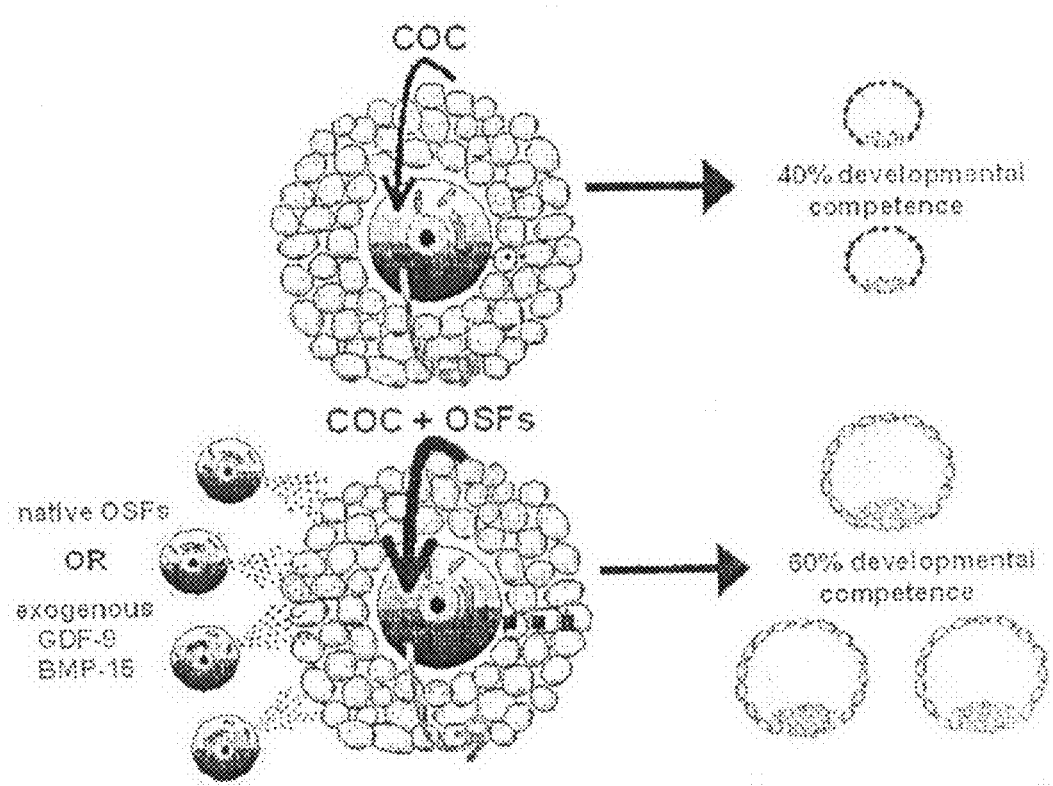
FIG. 27 shows a diagrammatic illustration of the hypothetical model derived from this study. Exposure of COCs during oocyte maturation to oocyte-secreted factors (OSFs), whether in their native form as an uncharacterized mix of growth factors secreted by the oocyte or as exogenous recombinant BMP15 or GDF9, substantially improves subsequent oocyte developmental competence (from ~40% to ~60%). OSFs are known to regulate a multitude of cumulus cell functions and this model proposes that these may include positive regulatory factors that pass back to the oocyte (bold arrows), improving subsequent development.

Treatment of control COCs with SB-431542 or follistatin significantly (P<0.05) decreased blastocyst development, compared to untreated COCs, suggesting that these antagonists were able to at least partially neutralize the effect of endogenous GDF9 or BMP15, respectively, that was secreted by the oocyte (FIGS. 2B & 3B). Consistent with experiment 2, exogenous GDF9 and BMP15 both increased blastocyst yields (P<0.05) in these experiments (FIGS. 25A and 26A), and these increases were ablated by the addition of their respective antagonists. Addition of SB-431542 or follistatin not only reduced blastocyst development to levels similar to untreated control COCs, but further depressed blastocyst rates to the levels of the control COCs treated with antagonists (FIGS. 25B & 26B). This suggests that SB-431542 and follistatin are neutralizing the effects of both exogenous and endogenous GDF9 or BMP15 on developmental competence of the oocyte. Blastocyst development rates from COCs matured with 293H were substantially reduced (P<0.05), regardless of whether SB-431542 or follistatin were added (FIGS. 25B & 26B).

EXAMPLE 24

Study V—Exogenous GDF9 During In Vitro Maturation of Oocytes Improves Subsequent Embryonic Development and Fetal Outcome The viability of an embryo is dependent on the developmental competence of the oocyte it is derived from. Recently, the existence and necessity of a bi-directional regulatory loop between oocytes and their somatic cells is becoming increasingly evident. The aim of this study was to assess the effects of the oocyte paracrine factor growth differentiation factor 9 (GDF9) added during mouse oocyte in vitro maturation (IVM) on subsequent embryo and fetal development.

COCs were aspirated from antral follicles of pre-pubertal (CBAxC57BL\6 hybrid) mice at 46 h post eCG and matured at 37° C. in 6% $CO_2$ 5% $O_2$ for 17 h in Waymouth's medium+ 5% FCS with or without 50 mIU/ml FSH/10 ng/ml EGF, recombinant mouse GDF9 (200 ng/ml) or the equivalent v/v control parent cell line 293H conditioned media. Oocytes (n=1106) were then fertilised and cultured to the blastocyst stage in G1.2/G2.2 medium at 37° C. in 6% $CO_2$ 5% $O_2$. Blastocysts were pooled and either transferred to pseudopregnant Swiss females or differentially stained. Pregnancy outcome was assessed on Day 15 of pregnancy.

The effects of GDF9 were dependent on the presence of FSH/EGF. With FSH/EGF, GDF9 increased cumulus expansion (3.1±0.1 cumulus expansion index vs 2.4±0.1; P<0.05). Although there was no significant effect of GDF9 on fertilisation, rate of development or blastocyst percentages (83% vs 75%). GDF9 significantly increased blastocyst total cell number (P=0.05), with greater differences in blastocyst inner cell mass (P=0.003) than trophectoderm cell numbers (P=0.07). Accordingly, implantation was not affected (83% vs 77%), but fetal development was almost doubled with addition of GDF9 (39% vs 21%; P=0.04).

This study demonstrates that, in the presence of FSH/EGF, exogenous GDF9 during IVM improves blastocyst quality and subsequent fetal viability. These findings highlight the importance of appropriate oocyte-somatic cell interactions, and also have significant implications for the development of IVM culture media as the impaired developmental competence of IVM oocytes may partly result from a GDF9 deficiency.

Finally, it will be appreciated that various modifications and variations of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in the art are intended to be within the scope of the present invention.

The invention claimed is:

1. A medium that supports culture of an oocyte, comprising:
    (a) a growth factor component comprising:
        (i) follicle stimulating hormone (FSH); and
        (ii) at least one of Growth Differentiation Factor 9 (GDF-9), Bone Morphogenetic Protein 15 (BMP-15) and Bone Morphogenetic Protein 6 (BMP-6); and optionally
    (b) at least one of the following:
        (i) one or more denuded oocytes;
        (ii) oocyte-conditioned medium;
        (iii) one or more oocyte secreted factors;
        (iv) an agent that increases the activity of a GDF-9-dependent signalling pathway in one or more of an oocyte, a cumulus cell associated with an oocyte, and an embryo;
        (v) an agent that increases the activity of a BMP-15-dependent signalling pathway in one or more of an oocyte, a cumulus cell associated with an oocyte, and an embryo; and (vi) an agent that increases the activity of a BMP-6-dependent signalling pathway in one or more of an oocyte, a cumulus cell associated with an oocyte, and an embryo.

2. A medium according to claim 1, wherein the medium further includes one or more of 40 mM to 400 mM NaCl, 0.1 mM to 20 mM KCl, and 0.1 mM to 40 mM glucose.

3. A medium according to claim 1, wherein the medium is a cumulus oocyte complex culture medium.

4. A medium according to claim 1, wherein the medium is an oocyte maturation medium.

5. A medium according to claim 1, wherein the medium is an in vitro fertilization medium.

6. A medium according to claim 1, wherein the medium is a medium for reducing atresia of a follicle.

7. A medium according to claim 1, wherein the medium is a freeze-thawing medium.

8. A method of increasing the developmental competence of an oocyte and/or an embryo produced from an oocyte, the method including exposing the oocyte to a medium according to claim 1.

9. A method of increasing oocyte maturation, the method including exposing an oocyte to a medium according to claim 1.

10. A method of increasing follicle maturation, the method including exposing a follicle to a medium according to claim 1.

11. A method of increasing developmental competence of an embryo, the method including exposing the embryo to a medium according to claim 1.

12. A method of assisted reproduction involving an oocyte, the method including exposing the oocyte to a medium according to claim 1.

13. A method according to claim 12, wherein the method of assisted of reproduction is in vitro fertilization.

14. A method of reducing atresia of a follicle, the method including exposing the follicle to a medium according to claim 1.

15. A method of freeze-thawing of one or more of an oocyte, a follicle, ovarian tissue, an ovary and an embryo, the method including exposing one or more of the oocyte, the follicle, the ovarian tissue, the ovary and the embryo to a medium according to claim 1 before freezing and/or after thawing.

16. A method of reducing apoptosis of a cumulus cell associated with an oocyte, the method including exposing the cumulus cell to a medium according to claim 1.

17. A combination product including:
(a) follicle stimulating hormone (FSH); and
(b) at least one of GDF-9 and BMP-15 and BMP-6; and (c) a medium that supports culture of a cumulus oocyte complex; and optionally;
(d) at least one of the following:
   (i) one or more oocyte secreted factors;
   (ii) oocyte conditioned medium;
   (iii) an agent that increases the activity of a GDF-9-dependent signalling pathway in one or more of an oocyte, a cumulus cell associated with an oocyte, and an embryo;
   (iv) an agent that increases the activity of a BMP-15-dependent signalling pathway in one or more of an oocyte, a cumulus cell associated with an oocyte, and an embryo; and
   (v) an agent that increases the activity of a BMP-6-dependent signalling pathway in one or more of an oocyte, a cumulus cell associated with an oocyte, and an embryo;
wherein components (a), (b) and (d) are provided in a form for addition to the medium that supports the culture of the cumulus oocyte complex.

18. A medium comprising:
(a) a growth factor component comprising:
   (i) follicle stimulating hormone (FSH), and at least one of epidermal growth factor (EGF), amphiregulin and epiregulin; and
   (ii) at least one of Growth Differentiation Factor 9 (GDF-9), Bone Morphogenetic Protein 15 (BMP-15) and Bone Morphogenetic Protein 6 (BMP-6); and optionally
(b) at least one of the following:
   (i) one or more denuded oocytes;
   (ii) oocyte-conditioned medium;
   (iii) one or more oocyte secreted factors;
   (iv) an agent that increases the activity of a GDF-9-dependent signalling pathway in one or more of an oocyte, a cumulus cell associated with an oocyte, and an embryo;
   (v) an agent that increases the activity of a BMP-15-dependent signalling pathway in one or more of an oocyte, a cumulus cell associated with an oocyte, and an embryo; and
   (vi) an agent that increases the activity of a BMP-6-dependent signalling pathway in one or more of an oocyte, a cumulus cell associated with an oocyte, and an embryo.

19. A combination product including:
(a) follicle stimulating hormone (FSH), and at least one of epidermal growth factor (EGF), amphiregulin and epiregulin;
(b) at least one of GDF-9, BMP-15 and BMP-6; and
(c) a medium that supports the culture of a cumulus oocyte complex; and optionally
(d) at least one of the following:
   (i) one or more oocyte secreted factors;
   (ii) oocyte conditioned medium;
   (iii) an agent that increases the activity of a GDF-9-dependent signalling pathway in one or more of an oocyte, a cumulus cell associated with an oocyte, and an embryo;
   (iv) an agent that increases the activity of a BMP-15-dependent signalling pathway in one or more of an oocyte, a cumulus cell associated with an oocyte, and an embryo; and
   (v) an agent that increases the activity of a BMP-6-dependent signalling pathway in one or more of an oocyte, a cumulus cell associated with an oocyte, and an embryo;
wherein components (a), (h) and (d) are provided in a form for addition to the medium that supports the culture of the cumulus oocyte complex.

* * * * *

UNITED STATES PATENT AND TRADEMARK OFFICE
CERTIFICATE OF CORRECTION

PATENT NO. : 8,530,235 B2  Page 1 of 1
APPLICATION NO. : 11/988949
DATED : September 10, 2013
INVENTOR(S) : Gilchrist et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 21 days.

Signed and Sealed this
Fifteenth Day of September, 2015

Michelle K. Lee
*Director of the United States Patent and Trademark Office*